United States Patent
Koo et al.

(10) Patent No.: US 9,566,247 B2
(45) Date of Patent: Feb. 14, 2017

(54) NANOPARTICLES FOR CONTROLLED RELEASE OF ANTI-BIOFILM AGENTS AND METHODS OF USE

(71) Applicants: Hyun Koo, Philadelphia, PA (US); Danielle Benoit, Rochester, NY (US); Marlise I. Klein, Rochester, NY (US); Megan L. Falsetta Wood, Rochester, NY (US)

(72) Inventors: Hyun Koo, Philadelphia, PA (US); Danielle Benoit, Rochester, NY (US); Marlise I. Klein, Rochester, NY (US); Megan L. Falsetta Wood, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/768,945

(22) PCT Filed: Feb. 25, 2014

(86) PCT No.: PCT/US2014/018211
§ 371 (c)(1),
(2) Date: Aug. 19, 2015

(87) PCT Pub. No.: WO2014/130994
PCT Pub. Date: Aug. 28, 2014

(65) Prior Publication Data
US 2015/0374634 A1    Dec. 31, 2015

Related U.S. Application Data

(60) Provisional application No. 61/768,929, filed on Feb. 25, 2013.

(51) Int. Cl.
*A61K 9/50*    (2006.01)
*A61K 31/045*    (2006.01)
(Continued)

(52) U.S. Cl.
CPC .......... *A61K 9/5026* (2013.01); *A61K 31/045* (2013.01); *A61K 31/352* (2013.01); *B82Y 5/00* (2013.01); *C08F 293/005* (2013.01); *C08L 53/00* (2013.01)

(58) Field of Classification Search
CPC .. A61K 31/045; A61K 31/352; A61K 9/5026; B82Y 5/00; C08F 293/005; C08L 53/00
See application file for complete search history.

(56) References Cited

U.S. PATENT DOCUMENTS 8,067,403 B2    11/2011    Whiteford et al.
8,188,068 B2    5/2012    Whiteford et al.
(Continued)

FOREIGN PATENT DOCUMENTS

WO    2005/030174    4/2005

OTHER PUBLICATIONS

Ambatipudi KS, Hagen FK, Delahunty CM, et al. Human common salivary protein 1 (CSP-1) promotes binding of *Streptococcus mutans* to experimental salivary pellicle and glucans formed on hydroxyapatite surface. *J Proteome Res.* 2010;9(12):6605-14.
(Continued)

*Primary Examiner* — Aradhana Sasan
(74) *Attorney, Agent, or Firm* — Riverside Law LLP

(57) ABSTRACT

The present invention relates to compositions and methods to treat and/or prevent biofilms and biofilm related diseases. The invention comprises a nanoparticle carrier (NPC) and at least one therapeutic agent therein. The NPC binds within biofilm and to surfaces at risk for biofilm formation and accumulation while providing local, sustained, enhanced and controlled delivery of the therapeutic agent, when triggered for release. In one embodiment, the NPC comprises pH-responsive elements that allows for specific delivery of the therapeutic agent when the local environment
(Continued)

dictates that the agent should be delivered precisely when it is most needed.

35 Claims, 20 Drawing Sheets

(51) Int. Cl.

| | | |
|---|---|---|
| *A61K 31/352* | (2006.01) | |
| *C08F 293/00* | (2006.01) | |
| *B82Y 5/00* | (2011.01) | |
| *C08L 53/00* | (2006.01) | |

(56) References Cited

U.S. PATENT DOCUMENTS

| 8,211,452 B2 | 7/2012 | Miksa et al. |
|---|---|---|
| 2007/0092575 A1 | 4/2007 | Balaban et al. |
| 2010/0021391 A1 | 1/2010 | Douglas et al. |
| 2011/0123636 A1 | 5/2011 | Stayton et al. |
| 2011/0171123 A1 | 7/2011 | Shirtliff et al. |
| 2012/0220981 A1 | 8/2012 | Soo et al. |
| 2012/0301424 A1 | 11/2012 | Cheng et al. |

OTHER PUBLICATIONS

Benoit DSW, Henry SM, Shubin AD, Hoffman AS, Stayton PS. pH-responsive polymeric sirna carriers sensitize multidrug resistant ovarian cancer cells to doxorubicin via knockdown of polo-like kinase 1. *Mol Pharm*. 2010;7(2):442-55.
Benoit DSW, Nuttelman CR, Collins SD, Anseth KS. Synthesis and characterization of a fluvastatin-releasing hydrogel delivery system to modulate hMSC differentiation and function for bone regeneration. *Biomaterials*. 2006;27(36):6102-6110.
Benoit et al., Multifunctional hydrogels that promote osteogenic hMSC differentiation through stimulation and sequestering of BMP2, 2007, *Adv Funct Mater*, 17(13): 2085-2093.
Benoit DSW, Srinivasan S, Shubin AD, Stayton PS. Synthesis of folate-functionalized RAFT polymers for targeted siRNA delivery. *Biomacromolecules*. 2011;12(7):2708-14.
Chen F, Liu X-M, Rice KC, et al. Tooth-binding micelles for dental caries prevention. *Antimicrob Agents Chemother*. 2009;53(11):4898-902.
Clawson et al., Synthesis and Characterization of Lipid-Polymer Hybrid Nanoparticles with pH-Triggered PEG Shedding, *Langmuir*, 2010, 27(17):10556- 10561.
Convertine AJ, Benoit DSW, Duvall CL, Hoffman AS, Stayton PS. Development of a novel endosomolytic diblock copolymer for siRNA delivery. *J Control Release*. 2009;133(3):221-9.
Convertine AJ, Diab C, Prieve M, et al. pH-Responsive Polymeric Micelle Carriers for siRNA Drugs. *Biomacromolecules*. 2010;11(11):2904-2911.
Falsetta et al., Novel Antibiofilm Chemotherapy Targets Exopolysaccharide Synthesis and Stress Tolerance in *Streptococcus mutans* to Modulate Virulence Expression In Vivo, 2012, *Antimicrob Agents Chemother*, 56(12): 6201-6211.
Fan J, Zeng F, Wu S, Wang X. Polymer micelle with pH-triggered hydrophobic-hydrophilic transition and de-cross-linking process in the core and its application for targeted anticancer drug delivery. *Biomacromolecules*. 2012;13(12):4126-37.
Gorbunoff MJ, Timasheff SN. The interaction of proteins with hydroxyapatite. *Anal Biochem*. 1984;136(2):440-445.
Jabra-Rizk MA, Meiller TF, James CE, Shirtliff ME. Effect of farnesol on *Staphylococcus aureus* biofilm formation and antimicrobial susceptibility.*Antimicrob Agents Chemother*. 2006;50(4):1463-9.
Kaneko M, Togashi N, Hamashima H, Hirohara M, Inoue Y. Effect of farnesol on mevalonate pathway of *Staphylococcus aureus*. *J Antibiot* (Tokyo). 2011;64(8):547-9.
Klein et al., *Streptococcus mutans* Protein Synthesis during Mixed-Species Biofilm Development by High-Throughput Quantitative Proteomics, 2012, PLoS One, 7(9): e45795.
Koo et al, Apigenin and *tt*-Farnesol with Fluoride on *S. mutans* Biofilm and Dental Caries, 2005, *J Dent Res*, 84(11): 1016-1020.
Koo H, Vacca Smith AM, Bowen WH, Rosalen PL, Cury JA, Park YK. Effects of Apis mellifera propolis on the activities of streptococcal glucosyltransferases in solution and adsorbed onto saliva-coated hydroxyapatite. *Caries Res*. 2000;34(5):418-26.
Koo H, Rosalen PL, Cury JA, Park YK, Bowen WH. Effects of Compounds Found in Propolis on *Streptococcus mutans* Growth and on Glucosyltransferase Activity. *Antimicrob Agents Chemother*. 2002;46(5):1302-1309.
Koo H, Hayacibara MF, Schobel BD, et al. Inhibition of *Streptococcus mutans* biofilm accumulation and polysaccharide production by apigenin and tt-farnesol. *J Antimicrob Chemother*. 2003;52(5):782-9.
Koo H, Xiao J, Klein MI, Jeon JG. Exopolysaccharides produced by *Streptococcus mutans* glucosyltransferases modulate the establishment of microcolonies within multispecies biofilms. *J Bacteriol*. 2010;192(12):3024-32.
Lendenmann U, Grogan J, Oppenheim FG. Saliva and Dental Pellicle—A Review. *Adv Dent Res*. 2000;14(1):22-28.
Manganiello MJ, Cheng C, Convertine AJ, Bryers JD, Stayton PS. Diblock copolymers with tunable pH transitions for gene delivery. *Biomaterials*. 2012;33(7):2301-9.
Rozen R, Bachrach G, Bronshteyn M, Gedalia I, Steinberg D. The role of fructans on dental biofilm formation by *Streptococcus sobrinus* , *Streptococcus mutans, Streptococcus gordonii* and *Actinomyces viscosus*. *FEMS Microbiol Lett*. 2001;195(2):205-210.
Tang Y, Liu SY, Armes SP, Billingham NC. Solubilization and controlled release of a hydrophobic drug using novel micelle-forming ABC triblock copolymers. *Biomacromolecules*. 2003;4(6):1636-45.
Van de Wetering, et al., A Mechanistic Study of the Hydrolytic Stability of Poly(2-(dimethylamino)ethyl methacrylate). 1998;300:8063-8068.
Van de Wetering P, Moret EE, Schuurmans-Nieuwenbroek NM, van Steenbergen MJ, Hennink WE. Structure-activity relationships of water-soluble cationic methacrylate/methacrylamide polymers for nonviral gene delivery. *Bioconjug Chem*. 1999;10(4):589-97.
Wang H, Rempel GL. pH-responsive polymer core-shell nanospheres for drug delivery. *J Polym Sci Part A Polym Chem*. 2013;51(20):4440-4450.
Weerkamp AH, Uyen HM, Busscher HJ. Effect of Zeta Potential and Surface Energy on Bacterial Adhesion to Uncoated and Saliva-coated Human Enamel and Dentin. *J Dent Res*. 1988;67(12):1483-1487.
Xiao J, Klein MI, Falsetta ML, et al. The exopolysaccharide matrix modulates the interaction between 3D architecture and virulence of a mixed-species oral biofilm. Mitchell AP, ed. *PLoS Pathog*. 2012;8(4):e1002623.
Supplementary EP Search Report dated Oct. 26, 2016 issued in corresponding EP ASN 14754022.

| | Polymers | | | | | | | | | Micelles | | |
|---|---|---|---|---|---|---|---|---|---|---|---|---|
| | Corona Blocks | | | | Core Blocks | Diblock Copolymers | | | | | | |
| Abbreviation | Composition | Mn | PDI | DP | Composition | Mn | PDI | DP | Size (d.nm) | Size PDI | ζ (mV) |
| NPC | p(DMAEMA) | 9.3 kDa | 1.3 | 100 | p(DMAEMA-co-BMA-co-PAA) | 21.9 kDa | 1.1 | 175 | 21±0.4 | 0.2±0.09 | +15.9±1.3 |
| C1 | p(DMAEMA) | 16.0 kDa | 1.01 | 100 | NA | NA | NA | NA | ND (soluble) | ND | ND |
| C2 | p(PEGMA) | 18.7 kDa | 1.08 | 100 | p(DMAEMA-co-BMA-co-PAA) | 29.0 kDa | 1.09 | 250 | 21±0.9 | 0.37±0.05 | -1.6±0.7 |
| C3 | p(DMAEMA) | 22.8 kDa | 1.08 | 150 | p(BMA) | 37.0 kDa | 1.01 | 250 | 38±2.8 | 0.21±0.02 | +17.2±1.7 |

Figure 7C

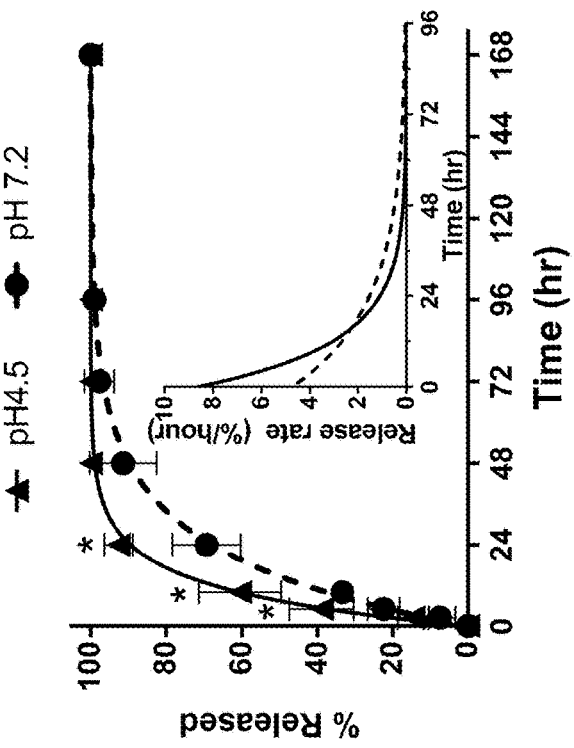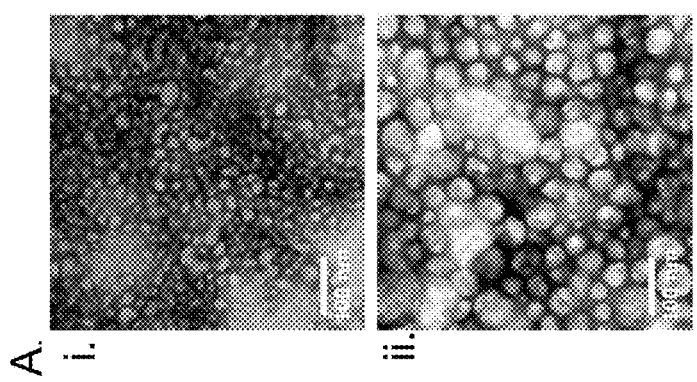
Figure 9A – Figure 9C

NANOPARTICLES FOR CONTROLLED RELEASE OF ANTI-BIOFILM AGENTS AND METHODS OF USE

CROSS-REFERENCE TO RELATED APPLICATIONS

This application is the U.S. national phase application filed under 35 U.S.C. §371 claiming benefit to International Patent Application No. PCT/US14/018211, filed on Feb. 25, 2014, which is entitled to priority under 35 U.S.C. §119 (e) to U.S. Provisional Application No. 61/768,929 filed on Feb. 25, 2013, the contents of which are incorporated herein by reference in their entirety.

BACKGROUND OF THE INVENTION

Many infectious diseases in humans are caused by virulent biofilms, including those occurring within the mouth (e.g., dental caries and periodontal diseases). For example, dental caries disease afflicts children and adults alike worldwide, and is a major reason for emergency room visits leading to absenteeism from work and school. The cost to treat the ravages of this disease exceeds $40 billion/yr in the US alone (Dye et al., 2007, Vital Health Stat, 1: 1-92).

The development of novel therapeutic approaches against biofilm-related diseases in the mouth is difficult due to (1) lack of retention of exogenously introduced agents via standard treatment regimen (topical application with brief exposures), (2) rapid clearance, and (3) the complexity of biofilm assembly. Topical agents must be retained or have prolonged effect without exhibiting broad-spectrum biocidal activity to prevent disruption of the complex oral (commensal) flora. At the same time, agents should not form complexes with salivary proteins that will lead to rapid clearance from the mouth.

The assembly of cariogenic biofilms is a dynamic process that is dependent on the development of a bacterial-derived EPS-rich matrix (Bowen et al., 2011, Caries Res, 45(1): 69-86). Within the complex oral microbiome, *Streptococcus mutans* is not always the most abundant organism. However, it can rapidly orchestrate the formation of cariogenic biofilms when sucrose becomes available. *S. mutans*-derived glucosyltransferases (Gtfs) are present in the pellicle and on bacterial surfaces, producing EPS in situ. EPS formed on surfaces promotes local accumulation of microbes on the teeth while forming a diffusion-limiting polymeric matrix that protects embedded bacteria. In parallel, sucrose and other sugars are fermented, creating acidic microenvironments (niches) across the biofilm and at the surface of attachment (Xiao et al., 2012, PLoS Pathog, 8(4): e1002623). These low-pH niches facilitate EPS production while cariogenic flora prospers within biofilms, ensuring biofilm accretion and localized acid-dissolution of the tooth enamel. Thus, nanoparticles can be engineered to carry existing and prospective agents at the site where biofilm formation actively occurs.

Current approaches for controlling/modulating virulent biofilm formation are limited. The development of novel therapeutic approaches in the mouth is difficult due to (1) lack of retention of exogenously introduced agents via standard treatment regimen (topical application with brief exposures), (2) rapid clearance from the mouth, and (3) the complexity of biofilm assembly. Topical agents must be retained or have prolonged effect without exhibiting broad-spectrum biocidal activity to prevent disruption of the complex oral (commensal) flora. Chlorhexidine is a broad-spectrum bactericidal agent that suppresses mutans streptococci levels in saliva, yet is far less effective against biofilms and is not suitable for daily preventive or therapeutic use. Fluoride, the mainstay for caries prevention, offers incomplete protection against caries and may not adequately address the infectious aspects of the disease (Ten Cate, 2012, J Dent Res, 91(9): 813-815). Recently, it has been demonstrated that that apigenin and farnesol effectively disrupt the development of cariogenic biofilm (Koo et al, 2005, J Dent Res, 84(11): 1016-1020; Falsetta et al., 2012, Antimicrob Agents Chemother, 56(12): 6201-6211). Apigenin inhibits EPS synthesis in situ while farnesol is a membrane-targeting agent that disrupts *S. mutans* acid tolerance at low pH values, all without bactericidal effect (Koo et al, 2005, J Dent Res, 84(11): 1016-1020). However, these agents have poor aqueous solubility and are not optimally retained in the mouth for sufficient duration to exert full therapeutic potential in vivo (Koo et al, 2005, J Dent Res, 84(11): 1016-1020).

Thus there is a need in the art for compositions and methods to provide effective retention of active agents while providing sustained and localized delivery of bioactives to the site where biofilm develops and accumulates. The present invention satisfies this unmet need.

SUMMARY OF THE INVENTION

The present invention includes a composition for preventing biofilm formation, preventing biofilm accumulation, and disrupting biofilm. The composition comprising at least one nanoparticle carrier (NPC) having a shell and a core, wherein the core comprises a therapeutically effective amount of at least one therapeutic agent.

In one embodiment, the NPC comprises at least one of dimethylaminoethylmethacrylate (DMAEMA), propylacrylic acid (PAA), butyl methacrylate (BMA). In one embodiment, the NPC comprises poly(dimethylaminoethyl methacrylate)-b-poly(dimethylaminoethyl methacrylate-co-propylacrylic acid-co-butyl methacrylate) (pDMAEMA-b-p (DMAEMA-co-PAA-co-BMA)).

In one embodiment, the composition comprises a pH-responsive element such that the NPC is disassembled when the NPC is in a locally acidic pH environment, thereby releasing the at least one therapeutic agent.

In one embodiment, the NPC binds to a biofilm. In one embodiment, the composition binds to multiple surfaces at risk for biofilm formation and accumulation.

In one embodiment, the at least one therapeutic agent comprises at least one agent selected from the group consisting of farnesol, apigenin, fluoride, chlorhexidine, and derivatives thereof.

In one embodiment, the at least one therapeutic agent is linked to the core via a degradable tether. In one embodiment, the length of the degradable tether controls the rate of release of the therapeutic agent.

In one embodiment, the NPC is incorporated into at least one of the group consisting of a liquid, foam, paste, gel, gum, membrane, dissolvable substrate, tablet, capsule, and lozenge.

The present invention includes a method for treating a biofilm. The method comprises administering to a surface having a biofilm a composition comprising at least one NPC and at least one therapeutic agent within the at least one NPC, wherein the at least one NPC binds selectively to the surface and is selectively triggered to release the at least one therapeutic agent, thereby providing local delivery of the therapeutic agent when the at least one therapeutic agent is released from the at least one NPC.

In one embodiment, the NPC comprises at least one of dimethylaminoethylmethacrylate (DMAEMA), propylacrylic acid (PAA), butyl methacrylate (BMA). In one embodiment, the at least one NPC comprises poly(dimethylaminoethyl methacrylate)-b-poly(dimethylaminoethyl methacrylate-co-propylacrylic acid-co-butyl methacrylate) (pDMAEMA-b-p(DMAEMA-co-PAA-co-BMA)).

In one embodiment, the at least one NPC is triggered to disassemble based upon a characteristic of the microenvironment of the surface, thereby releasing the at least one therapeutic agent. In one embodiment, the at least one NPC is triggered to disassemble when the at least one NPC is in locally acidic pH environment.

In one embodiment, the at least one therapeutic agent comprises at least one agent selected from the group consisting of farnesol, apigenin, fluoride, chlorhexidine, and derivatives thereof.

In one embodiment, the at least one NPC comprises a degradable tether linking the at least one therapeutic agent to a portion of the NPC, wherein the rate of release of the at least one therapeutic agent is dependent on the length of the degradable tether.

In one embodiment, the surface is in a subject. In one embodiment, the subject has a biofilm mediated condition. In one embodiment, the condition is selected from the group consisting of dental plaques, dental caries, gingivitis, periodontitis, urinary tract infections, catheter infections, middle-ear infections, and infections of implanted biomaterials. In one embodiment, the surface is a pellicle of the subject. In one embodiment, the subject is a mammal. In one embodiment, the mammal is selected from the group consisting of a human, a primate, a cow, a pig, a horse, a sheep, a cat, and a dog The present invention includes a method of treating an oral disease in a subject. The method comprises administering to a pellicle of the subject a composition comprising at least one NPC and at least one therapeutic agent within the at least one NPC, wherein the at least one NPC binds selectively to the surface and is selectively triggered to release the at least one therapeutic agent, thereby providing local delivery of the at least one therapeutic agent when the agent is released from the at least one NPC.

In one embodiment, the NPC comprises at least one of dimethylaminoethylmethacrylate (DMAEMA), propylacrylic acid (PAA), butyl methacrylate (BMA). In one embodiment, the at least one NPC comprises poly(dimethylaminoethyl methacrylate)-b-poly(dimethylaminoethyl methacrylate-co-propylacrylic acid-co-butyl methacrylate) (pDMAEMA-b-p(DMAEMA-co-PAA-co-BMA)).

In one embodiment, the at least one NPC is triggered to disassemble based upon a characteristic of the microenvironment of the surface, thereby releasing the at least one therapeutic agent. In one embodiment, the at least one NPC is triggered to disassemble when the at least one NPC is in locally acidic pH environment.

In one embodiment, the at least one therapeutic agent comprises at least one agent selected from the group consisting of farnesol, apigenin, fluoride, and chlorhexidine.

In one embodiment, the at least one NPC comprises a degradable tether linking the at least one therapeutic agent to a portion of the at least one NPC.

In one embodiment, the oral disease is selected from the group consisting of dental plaques, dental caries, gingivitis, periodontitis, denture stomatitis and oral candidiasis. In one embodiment, the subject is a mammal. In one embodiment, the mammal is selected from the group consisting of a human, a primate, a cow, a pig, a horse, a sheep, a cat, and a dog.

The present invention includes a method of preventing an oral disease in a subject. The method comprises administering to a pellicle of the subject a composition comprising at least one NPC and at least one therapeutic agent within the at least one NPC, wherein the at least one NPC binds selectively to the pellicle and is selectively triggered to release the at least one therapeutic agent, thereby providing local delivery of the at least one therapeutic agent when the agent is released from the at least one NPC.

In one embodiment, the NPC comprises at least one of dimethylaminoethylmethacrylate (DMAEMA), propylacrylic acid (PAA), butyl methacrylate (BMA). In one embodiment, the at least one NPC comprises poly(dimethylaminoethyl methacrylate)-b-poly(dimethylaminoethyl methacrylate-co-propylacrylic acid-co-butyl methacrylate) (pDMAEMA-b-p(DMAEMA-co-PAA-co-BMA)).

In one embodiment, the at least one NPC is triggered to disassemble based upon a characteristic of the microenvironment of the surface, thereby releasing the at least one therapeutic agent. In one embodiment, the at least one NPC is triggered to disassemble when the at least one NPC is in locally acidic pH environment.

In one embodiment, the at least one therapeutic agent comprises at least one agent selected from the group consisting of farnesol, apigenin, fluoride, and chlorhexidine.

In one embodiment, the at least one NPC comprises a degradable tether linking the at least one therapeutic agent to a portion of the at least one NPC.

In one embodiment, the oral disease is selected from the group consisting of dental plaques, dental caries, gingivitis, periodontitis, denture stomatitis and oral candidiasis. In one embodiment, the subject is a mammal. In one embodiment, the mammal is selected from the group consisting of a human, a primate, a cow, a pig, a horse, a sheep, a cat, and a dog.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A and FIG. 2B, are a set of images depicting the composition, structure, and function of pH-responsive NPC. FIG. 2A depicts NPC composition: poly(dimethylaminoethyl methacrylate)-b-poly(dimethylaminoethyl methacrylate-co-propylacrylic acid-co-butyl methacrylate) (pDMAEMA-b-p(DMAEMA-co-PAA-co-BMA)). FIG. 2B depicts the pH-dependent structure of NPC. The outer element (in black) is protonated at physiological pH, and was designed to have high avidity to the pellicle. The inner element (in blue) was designed to be nearly charge neutral at physiological pH but hydrophobic with inclusion of BMA. The inner element becomes more protonated at lower pH environments, disassembling the NPC and releasing the drug(s) from nanoparticle cores.

FIG. 3A through FIG. 3C, is a set of images demonstrating that NPC bind effectively to the salivary pellicle and EPS-matrix. FIG. 3A demonstrates that NPC binds to pellicle. FIG. 3B demonstrates that NPC binds to EPS formed in situ by surface-adsorbed GtfB. FIG. 3C demonstrates that NPC are incorporated into biofilm matrix. Representative images of a 22 h-old S. mutans biofilm formed on sHA disc surface.

FIG. 6A and FIG. 6B, are a set of exemplary timelines depicting the experimental design to evaluate the effect of NPC-delivered agents. FIG. 6A depicts an experimental design to study the effects on initial biofilm assembly, and on further accumulation of biofilms. FIG. 6B depicts an experimental design to study the effects on disassembly or build-up prevention of pre-formed biofilms.

FIG. 7, comprising FIG. 7A through FIG. 7D, depicts the structure and function of NPCs, and the properties of polymers used in the experiments. FIG. 7A: Depiction of the chemistry and self-assembly of diblock copolymers. Cationic and pH-responsive ~20 kDa diblock copolymers with equivalent $1^{st}$ to $2^{nd}$ block molecular weight and PDI of 1.1 were synthesized by 2-step RAFT polymerizations as indicated, and self-assembled into micelle-based NPC\) in aqueous solutions via sonication. FIG. 7B: Structures of control polymers utilized to isolate required physicochemical characteristics for binding to dental surfaces. FIG. 7C: Characterization of all polymers and micelle-base nanoparticles employed in binding experiments. Mn is number average molecular weight, PDI is the molecular weight polydispersity index, DP is degree of polymerization, size PDI is the polydispersity of micelle diameters, and $\zeta$ is micelle zeta-potentials. NA=not applicable (no micelle structure), and ND=not detectable. FIG. 7D: Proposed mode of action of pH-responsive NPC for prevention and/or treatment of biofilms.

FIG. 8, comprising FIG. 8A: Characterization of polymer binding to mimetic dental surfaces. Binding experiments were performed at 1 μM. The error bars represent SEM (n=3) and the asterisks denote significant differences at p<0.01. FIG. 8B: Confocal images of polymer binding at 85 μM (scale bars, 20 μm). FIG. 8C: Percent surface area covered by polymers. Nanoparticles with PEG coronas adsorbed to a much lower extent compared to nanoparticles with p(DMAEMA) coronas and to p(DMAEMA) alone. FIG. 8D: Equilibrium binding profile of NPC at increasing polymer concentrations. The solid and dotted lines represent Langmuir fits to the adsorption data. FIG. 8E: Fold increases in binding of NPC and p(DMAEMA) to hydroxyapatite (HA), as a function of pH. The binding of p(DMAEMA) and NPC to HA was similar, whereas in both conditions altered, adsorption increased as pH decreased ($R^2>0$) as assessed by Two-Tailed Student's T-tests (p<0.01). FIG. 8F: Fold increase in NPC binding as a function of zeta potential at a range of pH values. Binding and zeta potential were altered by varying the pH of NPC solutions, as indicated on the graph. The solid line denotes Pearson correlation and external and internal dotted lines denote confidence intervals of Pearson correlation at 95% confidence. FIG. 8G: Langmuir fit parameters that define binding capacity ($b_{max}$) and affinity ($K_a$). The Langmuir parameters were calculated based on data presented in FIG. 8D ($R^2>0.98$).

FIG. 9, comprising FIG. 9A through FIG. 9E, depicts the results of experiments investigating the drug loading, pH-triggered release, and anti-bacterial activity of farnesol-loaded NPC. FIG. 9A: Transmission electron microscopy (TEM) images that demonstrate an increase in NPC size upon loading; control (unloaded, i) and loaded at 17.5 wt % (ii). FIG. 9B: Farnesol release profiles at pH 7.2 and 4.5, including farnesol release rates (inset). Solid and dotted lines show fits ($R^2>0.98$) to first-order drug release and release rates determined by first derivative of the fits (inset). FIG. 9C: Kinetic parameters of release determined from fits to first order release. Initial release rate (FIG. 9B. inset, $r_0$), release rate constant ($k_{obs}$) and half-time of release ($t_{1/2}$) at pH 4.5 suggest 2-fold faster release at pH 4.5 as compared to pH 7.2. FIG. 9D: Antibacterial activity of loaded NPC at pH 7.2. FIG. 9E: Effect of low pH (4.5) on bacterial survival after treatment with loaded NPC. A ~3 log decrease in bacterial viability was observed after 1 h of exposure to loaded NPC. No further effect on bacterial survival was observed over time after transferring the bacteria from growth media to PBS at pH 7.2, whereas at pH 4.5 a decrease in viability over time was apparent in both treated and control groups. Error bars represent standard error (n=3) for release experiments and (n=4) for antibacterial activity experiments. Asterisks denote significant differences at p<0.01, as determined by two-way ANOVA followed by Tukey's test for multiple comparisons.

FIG. 10A through FIG. 10C, depicts the results of experiments demonstrating the anti-biofilm effects of farnesol delivery via NPC. FIG. 10A: Treatment regimen that was used to emulate the clinically relevant regimen of 2-3 treatments per day. A 50% reduction in the number of colony forming units per dry weight (FIG. 10B) and 2-fold increase in biofilm removal under shear stress (FIG. 10C), were achieved in biofilms treated with farnesol-loaded NPC (18.5 wt %) as compared to controls. Error bars represent standard error and asterisks denote significant difference as assessed by tow-way ANOVA followed by Tukey's test for multiple comparisons (n=4, p<0.01).

FIG. 13A and FIG. 13B, depicts the results of experiments investigating NPC loading at a range of drug concentrations. Loading capacities (FIG. 13A) and loading efficiencies (FIG. 13B) of NPC measured by farnesol emulsion turbidity (n=2), and confirmed by HPLC (n=1).

DETAILED DESCRIPTION

Figure 1:
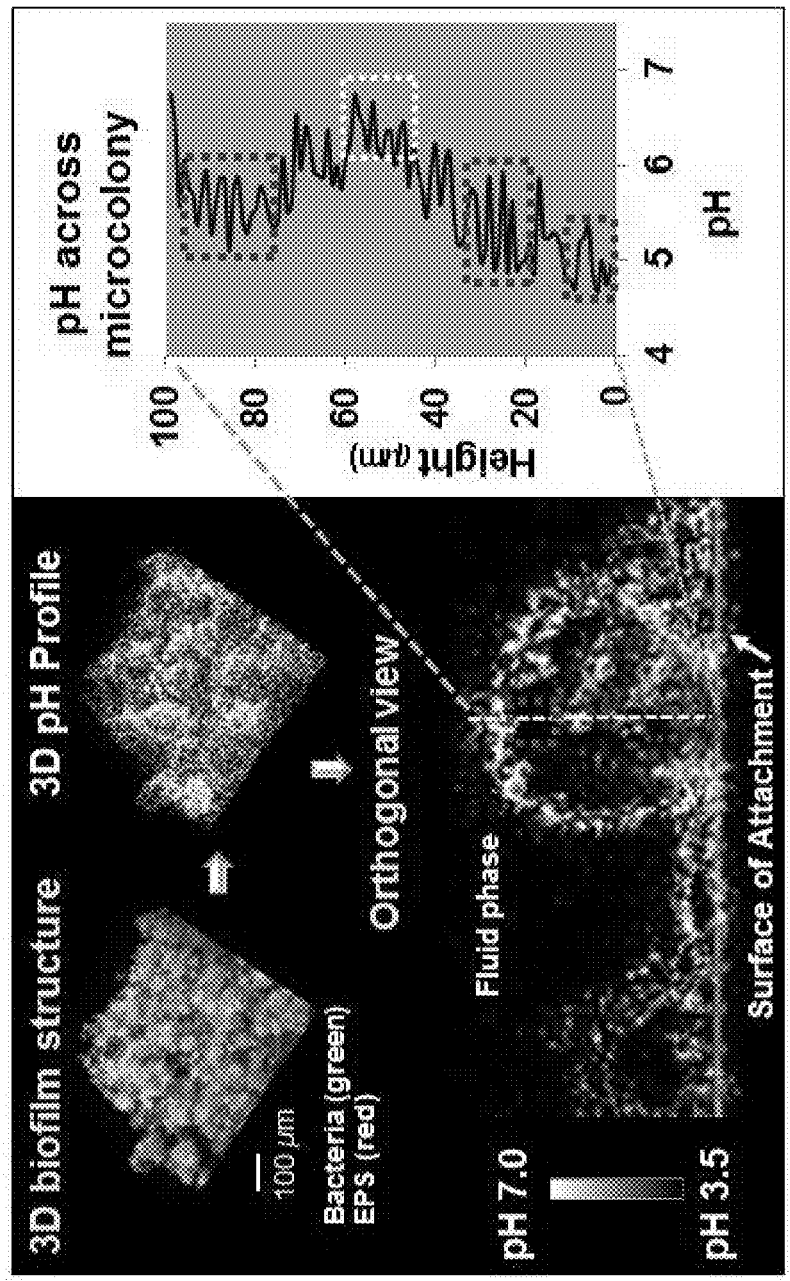
FIG. 1 is an image depicting the acidic niches within cariogenic biofilm. Dark areas indicate regions of low pH (dotted boxes), while white or light areas are indicative of regions of pH that are close to neutral. Thus, the biofilm microenvironment is highly acidic.

The present invention relates generally to compositions and methods to inhibit the formation of biofilms. In one embodiment, the invention is used to treat and/or prevent biofilms and infectious diseases caused by biofilms. In one embodiment, the invention is useful for treating and/or preventing biofilms in the mouth of a subject. The invention is therefore useful for treating and/or preventing a wide variety of oral diseases including, but not limited to, dental caries, gingivitis, periodontal diseases, as well as biofilm-associated mucosal infections, including for example, denture stomatitis and oral candidiasis. The present invention is not limited to the treatment or prevention of biofilms in medical settings, but also encompasses the treatment or prevention of biofilms in environmental, commercial, and industrial settings.

In one embodiment, the present invention provides a composition that inhibits the formation of biofilms. In one embodiment, the composition inhibits further accumulation of biofilm. In one embodiment, the composition promotes the disruption or disassembly of existing biofilms. In one embodiment, promoting the disruption or disassembly of existing biofilms allow for easier mechanical biofilm disruption. In one embodiment, the composition weakens an existing biofilm, allowing for easier mechanical biofilm disruption. In one embodiment, the composition inhibits the formation and further accumulation of biofilm.

In one embodiment, the composition comprises a nanoparticle carrier (NPC) and at least one therapeutic agent. The NPC is capable of binding to a biofilm and to sites at risk for biofilm formation and accumulation, thereby providing sustained drug delivery of the at least one therapeutic agent. Thus, the NPC provides targeted drug-delivery at the site of biofilm formation.

The present invention is partly based upon the discovery that the NPC is capable of binding avidly to at least 3 clinically relevant sites: 1) the pellicle, a salivary film that covers the teeth and mucosal surfaces, 2) extracellular polysaccharides (EPS) formed on pellicle, which enhances bacterial adhesion and local accumulation of harmful bacteria, (e.g. S. mutans), and 3) EPS-rich matrix within biofilms. Thus, the NPC acts as a homing device (for therapeutic agents) that attaches to 'at-risk' sites for biofilm formation and accumulation, as well as within biofilms.

Therefore, the NPC helps to retain the therapeutic agents locally, and, when triggered for release of the therapeutic agents, provides controlled, enhanced, and sustained drug delivery of the therapeutic agent directly on the sites where biofilm initiates and accumulates, thereby preventing biofilm formation. Furthermore, NPC also carries and retains the therapeutic agents within biofilms, thereby inhibiting further biofilm accumulation and promoting the disruption of existing biofilm. Thus, the NPC provides targeted drug-delivery that could inhibit both the initial assembly and further accumulation of the biofilms as well as promote disruption and disassembly of existing biofilm.

In one embodiment, the at least one therapeutic agent comprises an anti-biofilm agent. The therapeutic agent includes any naturally occurring, synthetic, inorganic, organic, peptide, enzyme, nucleic acid small molecule, and the like, which has at least some activity in treating and/or preventing biofilm. In certain embodiments, the therapeutic agent comprises apigenin, farnesol, derivatives thereof, and combinations thereof. In another embodiment, the at least one therapeutic agent comprises an anti-bacterial agent, including but not limited to chlorhexidine. In another embodiment, the at least one therapeutic agent comprises fluoride. It is demonstrated herein that the NPC can be loaded with therapeutically effective amounts of anti-biofilm therapeutic agents. The NPC also provides for controllable release of the loaded therapeutic agent.

In one embodiment, the NPC retains the at least one therapeutic agent until it is triggered to release the at least one therapeutic agent. This allows the at least one therapeutic agent to be released only when and where it is most needed, thereby avoiding wasting the agent.

In one embodiment, the NPC is pH-activated, in which the at least one therapeutic agent is released at a rate that is dependent on the pH of the local environment. In certain embodiments, the therapeutic agent is released when the NPC is within a local environment with a pH that deviates from the normal physiological pH range. For example, in one embodiment, the therapeutic agent is only released when the local pH becomes acidic. For example, in certain embodiments, the agent is not released or minimally released at neutral pH found in non-pathological (also termed physiological) conditions, but the rate of release is increased at acidic pH, precisely when release is needed. Thus, there is no waste and no risk of overexposure of the agents when they are not needed.

The present invention also provides a method for treating and/or preventing biofilms and diseases related to formation of biofilms. In one embodiment, the method comprises administering an effective amount of a composition comprising an NPC and at least one therapeutic agent to a subject.

In one embodiment, the method of the invention treats and/or prevents dental caries by reducing the amount of, or preventing the formation of, cariogenic biofilms on the pellicle-covered teeth of a subject. The method provides effective, sustained, and localized delivery of a therapeutic agent within biofilm and to sites at risk for biofilm formation and accumulation.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein the term "biofilm" refers to any three-dimensional, matrix-encased microbial community displaying multicellular characteristics. Accordingly, as used herein, the term biofilm includes surface-associated biofilms as well as biofilms in suspension, such as flocs and granules. Biofilms may comprise a single microbial species or may be mixed species complexes, and may include bacteria as well as fungi, algae, protozoa, or other microorganisms.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein with respect to the compositions of the invention, "biologically active" means that the compositions elicit a biological response in a mammal that can be monitored and characterized in comparison with an untreated mammal.

As used herein, the term "treating" means ameliorating the effects of, or delaying, halting or reversing the progress of a disease or disorder. The word encompasses reducing the severity of a symptom of a disease or disorder and/or the frequency of a symptom of a disease or disorder.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease. Disease and disorder are used interchangeably herein.

As used herein, the term "medical intervention" means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

As used herein, the terms "effective amount" or "therapeutically effective amount" or "pharmaceutically effective amount" of a composition are used interchangeably to refer to the amount of the composition that is sufficient to provide a beneficial effect to the subject to which the composition is administered. The term to "treat," as used herein, means reducing the frequency with which symptoms are experienced by a patient or subject or administering a composition to reduce the severity with which symptoms are experienced. An appropriate therapeutic amount in any individual case may be determined by one of ordinary skill in the art using routine experimentation.

By the term "specifically bind" or "specifically binds," as used herein, is meant that a first molecule (e.g., an antibody) preferentially binds to a second molecule (e.g., a particular antigenic epitope), but does not necessarily bind only to that second molecule.

As used herein, a "prophylactic" or "preventive" treatment is a treatment administered to a subject who does not exhibit signs of a disease or disorder or exhibits only early signs of the disease or disorder for the purpose of decreasing the risk of developing pathology associated with the disease or disorder.

As used herein, a "therapeutic" treatment is a treatment administered to a subject who exhibits signs of pathology of a disease or disorder for the purpose of diminishing or eliminating those signs.

As used herein, the term "pellicle" or "dental pellicle" refers to a thin protein film that forms on the surface enamel of a tooth. Different species of bacteria within the oral cavity may, in certain instances, form a biofilm on the pellicle which, in some instances, leads to dental caries and other oral diseases.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, a "pharmaceutically acceptable carrier" means a pharmaceutically acceptable material, composition or carrier, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. As used herein "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds can also be incorporated into the compositions.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "polymer" refers to a molecule composed of repeating structural units typically connected by covalent chemical bonds. The term "polymer" is also meant to include the terms copolymer and oligomers. In one embodiment, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "subject" refers to a human or another mammal (e.g., primate, dog, cat, goat, horse, pig, mouse, rat, rabbit, and the like) that can have a biofilm related condition or be at risk for developing a biofilm related condition, but may or may not have a biofilm related condition or be at risk for developing a biofilm related condition. In many embodiments of the present invention, the subject is a human being. In such embodiments, the subject is often referred to as an "individual" or a "patient." The terms "individual" and "patient" do not denote a particular age.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods to inhibit the formation of biofilms. In certain embodiments, the invention is used to treat and/or prevent biofilms and infectious diseases caused by biofilms. Biofilms are known to be involved in a variety of infections throughout the body. Conditions in which biofilms are implicated, and thus the present invention is useful in treating, include, but is not limited to, dental plaques, dental caries, gingivitis, urinary tract infections, catheter infections, middle-ear infections, and infections of implanted biomaterials (e.g. artificial joints, artificial valves, etc).

The present invention is not limited to the treatment or prevention of biofilms in the body or in medical settings. It is known in the art that biofilms can form on a variety of surfaces which can lead to diverse detrimental issues. For example, biofilm formation in kitchen or bathroom surfaces may present a host of sanitation issues. Further, biofilm formation on marine engineering systems or marine vehicles may lead to corrosion and biofouling. Therefore, the present invention encompasses the treatment or prevention of biofilms that may occur in environmental, commercial, industrial, or other settings.

In one embodiment, the present invention provides a composition that inhibits the formation of biofilms. In one embodiment, the composition inhibits the accumulation of biofilm. In one embodiment, the composition promotes the disruption or disassembly of exiting biofilm. In one embodiment, the composition comprises at least one nanoparticle carrier (NPC) and at least one therapeutic agent loaded in the at least one NPC. In one embodiment, the NPC provides localized and sustained drug delivery of the at least one therapeutic agent. The present invention is partly based upon the surprising discovery that NPC, comprised of polymer-based cationic micelles bind to all surfaces relevant to biofilm formation and development, including pellicle, exopolysaccharides (EPS) formed along the pellicle (targeting surfaces at risk), and to EPS-rich matrix within biofilms (targeting biofilm microenvironment). Thus, the NPC are specifically targeted to regions at risk for formation (saliva-coated surfaces, e.g. pellicle) and accumulation (EPS-coated surfaces) of a biofilm, as well as within biofilms (matrix). It was also discovered that the NPC is able to be loaded with therapeutically effective amounts of a therapeutic agent, and thus can be used to effectively deliver clinically relevant doses of a therapeutic agent to an area of need. Further, as NPC remains bound to such regions, the NPC acts as a homing device by retaining the therapeutic agent at those sites, allowing for sustained, controlled, and local drug-delivery, a feature sorely lacking in traditional therapy. Traditional therapeutic approaches based on topical applications have generally been defective, due to the lack of retention of the drug at these clinically relevant sites within the mouth. The composition of the present invention overcomes this limitation, as the therapeutic agent is retained at the treatment site well after application.

In one embodiment, the NPC retains the at least one therapeutic agent until it is triggered to release the at least one therapeutic agent. This allows the at least one therapeutic agent to be released only when and where it is most needed, thereby avoiding wasting the agent. For example, the NPC may be triggered to release the at least one therapeutic agent by a variety of factors in the microenvironment, including but not limited to, temperature, pH, biomolecule recognition, and the like.

In one embodiment, the NPC is pH-activated, in which the at least one therapeutic agent is released at a rate that is dependent on the pH of the local environment. In certain embodiments, the therapeutic agent is released when the NPC is within a local environment with a pH that deviates from the normal physiological pH range. For example, in one embodiment, the therapeutic agent is released when the local pH is acidic. The present invention is partly based upon the inclusion of pH-responsive elements within the NPC. As such, the composition of the invention provides a controllable release of therapeutic agent, depending on the pH of the local environment thereby making the therapeutic agent available precisely when it is most needed. For example, in certain conditions, the development of acidic niches within biofilms are essential in causing oral diseases (such as dental caries) because: 1) the niches favor the growth of caries-causing and acid-producing organisms, 2) the niches induce further biofilm accumulation, and 3) the local acidity causes acid-dissolution of the tooth. The agent within the NPC is minimally released at physiological pH (in non-diseased situation). Thus, in these pathological conditions, it is beneficial for the NPC to release the embedded therapeutic agent specifically if and when the local environment becomes acidic, when they are most needed. In certain embodiments, specific release in acidic local environment is beneficial as the therapeutic agent is most active in these conditions. For example, farnesol effects on bacteria are enhanced at low pH and the capacity of fluoride to re-mineralize tooth and to affect bacteria growth is dramatically enhanced at acidic pH. In one embodiment, the pH-dependent rate of drug-delivery is dependent upon the particular composition of the NPC. As such, the present invention encompasses a variety of NPC compositions that are tailored for specific release rates at specific pH. For example, in one embodiment the NPC of the invention comprises at least one degradable tether and/or at least one degradable bond, where the specific number of degradable tethers and bonds dictate the pH-dependent release rate from the NPC.

As the NPC remains bound to at risk regions for biofilm formation, the NPC acts as a homing device by retaining the bioactive agents, allowing, when triggered, sustained, controlled and local drug-delivery directly on the sites where biofilm initiates. NPC also carries and retains the bioactive agents within biofilms, thereby inhibiting further biofilm accumulation and promoting disruption or disassembly of existing biofilm. Furthermore, NPC provides a controllable release of therapeutic agent, depending on the pH of the local environment.

In one embodiment, the NPC comprises at least one therapeutic agent. The present invention is not limited to any particular therapeutic agent, but rather encompasses any suitable therapeutic agent that can be embedded within the NPC. Exemplary therapeutic agents include, but are not limited to, anti-viral agents, anti-bacterial agents, anti-biofilm agents, chemotherapeutic agents, anti-inflammatory agents, antiseptics, anesthetics, analgesics, pharmaceutical agents, small molecules, peptides, nucleic acids, and the like. In one embodiment, the therapeutic agent comprises an anti-biofilm agent, including but not limited to apegenin and derivatives thereof; flavonoids including flavones, flavonols, dihydroflavonols, flavonones, and derivatives thereof; farnesol and derivatives thereof; terpenoids including terpenes, terpinols, diterpenic acids, diterpenes, triterpenes, and derivatives therof; biofilm degrading enzymes including mutanase, dextranase, and amyloglucosidade-glucose oxidase; and EPS-synthesizing enzyme inhibitors including Rose Bengal, Perborate, meta-periodate, sorbitol, xylitol, 1-deoxynojirimycin, flavonoids, polyphenols, proanthocyanidins, tannins, and coumarins.

In another embodiment, the at least one therapeutic agent comprises an antibacterial agent, including but not limited to chlorhexidine and derivatives thereof, members of the bisbiguanide class of inhibitors, povidone iodine, hydrogen peroxide, doxycycline, minocycline, clindamycin, doxycycline, metronidazole, essential oil extracts (menthol, thymol, eucalyptol, methyl salicylate, metal salts (zinc, copper, stannous ions), phenols (triclosan), all quaternary ammonium compounds (cetylpyridinium chloride), surfactants (sodium lauryl sulphate, delmopinol), all natural molecules (phenols, phenolic acids, quinones, alkaloids, lectins, peptides, polypeptides, indole derivatives, flustramine derivatives, carolacton, halogenated furanones, oroidin analogues, agelasine, ageloxime D).

In another embodiment, the at least one therapeutic agent comprises fluoride. Fluoride can be included as any one of its formulations including, but not limited to sodium fluoride, monofluorophosphate and its derivatives, and stannous fluoride.

In one embodiment, the composition comprises a plurality of different NPCs, wherein each of the different NPCs comprise a different therapeutic agent. For example, in one embodiment, the composition comprises a first NPC, comprising an anti-biofilm agent, and a second NPC, comprising fluoride. In another embodiment, the composition comprises a first NPC, comprising an anti-biofilm agent, a second NPC, comprising a broad-spectrum antibiotic, and a third NPC, comprising fluoride. Each of the different NPCs can be configured for different drug delivery characteristics, thereby allowing different therapeutic agents to be delivered at different times, as necessitated by the particular disorder or treatment.

In certain embodiments, the composition of the invention is a solution, foam, paste, gel, gum, dissolvable substrate, tablet, lozenge, or the like, which an NPC of the invention can be incorporated into. For example, the composition may be of any form which allows its application onto a surface having a biofilm, or at risk for developing a biofilm. In dental applications, the composition may be of any form that allows its application to the pellicle or tooth of a subject.

The present invention also provides a method for treating and/or preventing biofilms and diseases related to formation of biofilms. In one embodiment, the method comprises administering an effective amount of a composition comprising an NPC and at least one therapeutic agent to a subject. As discussed elsewhere herein, the composition of the invention provides for local sustained delivery of the at least one therapeutic agent specifically within biofilm matrix, at a site of biofilm formation, at a site of biofilm accumulation, and/or at site at risk for biofilm formation and/or accumulation. Since the composition of the invention binds to biofilm and sites at risk for biofilm formation and accumulation, the method of the invention does not necessitate frequent application of the composition. Thus, in one embodiment, the method comprises a single application of an effective amount of a composition comprising NPC and at least one therapeutic agent.

In one embodiment, the present invention comprises a method to treat and prevent dental caries by reducing the amount of, preventing the formation of, or preventing the accumulation of cariogenic, biofilms along the pellicle of the tooth of a subject. The method provides effective, sustained, and localized delivery of a therapeutic agent within biofilm, to the site of biofilm formation and/or accumulation, or to the site at risk for biofilm formation and/or accumulation. In one embodiment, the method provides a pH-dependent release of the therapeutic agent from the NPC. The formation of cariogenic biofilms includes the development of acidic niches within the biofilm. Thus, in one embodiment, the method comprises delivery of the therapeutic agent from the NPC specifically if and when the local environment becomes acidic, precisely when the therapeutic agent is most needed.

In one embodiment, the therapeutic agent delivered by way of the method of the invention comprises, apegenin, farnesol, chlorhexidine, fluoride, and a combination thereof. However, the method is not limited to any particular agent. For example, the inventive method allows for inclusion of certain therapeutic agents that would not be able to be delivered using traditional means. In certain embodiments, the therapeutic agent or agents are embedded or encapsulated within NPCs. It is demonstrated herein that NPCs display the ability to be loaded with therapeutically effective amounts of a therapeutic agent. The localized and conditional release of therapeutic agent allows for the method to comprise delivery of harsh therapeutic agents, which would be harmful for the subject if not delivered at specific locations and conditions. For example, traditional application of broad-spectrum antibiotics to the mouth could be harmful for the subject, as the antibiotics would destroy all bacterial species within the oral cavity, some of which are actually beneficial to the health of the subject. However, localized and enhanced delivery when triggered, such as that achieved by the method of the invention, allows for delivery of the same agent because only the bacterial species associated with the pathology (e.g. biofilm, caries, etc) are targeted, while the beneficial species located elsewhere in the oral cavity are spared.

Composition

The present invention provides a composition comprising a nanoparticle carrier (NPC) to provide sustained and enhanced local drug delivery when triggered. The NPC is a polymer based micelle assembly which interacts with target surfaces. As discussed elsewhere herein, the NPC of the invention binds within biofilm and to regions at risk for biofilm formation and accumulation. In one embodiment, the NPC is pH-responsive, where an embedded therapeutic agent is delivered at rate that is dependent on the local pH. In a preferred embodiment, the NPC comprises dimethylaminoethylmethacrylate (DMAEMA), propyl acrylic acid (PAA), butyl methacrylate (BMA), or copolymers thereof. Exemplary compositions of the NPC are described in U.S. Patent Application Publication No. US2011/0123636, which is incorporated herein by reference.

In one embodiment, the composition comprises a NPC comprising at least one therapeutic agent. For example, in one embodiment, the NPC comprises at least one anti-biofilm agent.

In one embodiment, the at least one therapeutic agent is conjugated within the NPC via linkages and/or tethers. In one embodiment, the tethers are degradable, when triggered, which allows for the release of the therapeutic agent from the NPC into the targeted tissue. The length and number of tethers dictates the release rate of the therapeutic agent, as described in Benoit et al., 2007, Adv Funct Mater, 17(13): 2085-2093 and Benoit et al., 2006, Biomaterials, 27(36): 6102-6110, each of which are incorporated herein by reference.

In one embodiment, the composition comprises a plurality of different NPCs, wherein each of the different NPCs comprise a different therapeutic agent, thereby allowing for local and controlled delivery of a plurality of therapeutic agents.

NPC Structure

Provided in some embodiments herein is a NPC comprising a plurality of block copolymers. In certain embodiments, the NPC comprises a core and a shell.

In specific embodiments, the core block of the block copolymers described herein is a pH dependent hydrophobe. In certain embodiments, the shell block is hydrophilic. In specific embodiments, the shell block is hydrophilic at about a neutral pH.

In some embodiments, a block copolymer comprises (i) a plurality of hydrophobic monomeric residues, (ii) a plurality of anionic monomeric residues having a chargeable species, the chargeable species being anionic at physiological pH, and being substantially neutral or non-charged at an acidic pH and (iii) optionally a plurality of cationic monomeric residues. In some of such embodiments, the ratio of anionic:cationic species in a block copolymer ranges from about 4:1 to about 1:4 at physiological pH. In some of such embodiments, modification of the ratio of anionic to cationic species in a hydrophobic block of a block copolymer allows for modification of activity of a NPC described herein. In some of such embodiments, the ratio of anionic:cationic species in a hydrophobic block of a block copolymer described herein ranges from about 1:2 to about 3:1, or from about 1:1 to about 2:1 at physiological pH.

In certain embodiments, the block copolymers present in a NPC provided herein comprise a core section (e.g., core block) that comprises a plurality of hydrophobic groups. In more specific embodiments, the core section (e.g., core block) comprises a plurality of hydrophobic groups and a plurality of first chargeable species or groups. In still more specific embodiments, such first chargeable species or groups are negatively charged and/or are chargeable to a negatively charged species or group (e.g., at about a neutral pH, or a pH of about 7.4). In some specific embodiments, the core section (e.g., core block) comprises a plurality of hydrophobic groups, a plurality of first chargeable species or groups, and a plurality of second chargeable species or groups. In more specific embodiments, the first chargeable species or groups are negatively charged and/or are chargeable to a negatively charged species or group, and the second chargeable species or groups are positively charged and/or are chargeable to a positively charged species or group (e.g., at about a neutral pH, or a pH of about 7.4).

In certain embodiments, the shell of the NPC and/or the shell blocks of the block copolymers described herein also comprise a chargeable species or groups. In some embodiments, one or more of the block copolymers present in a NPC provided herein has a shell section that comprises a plurality of cationically chargeable species or groups. Depending on the concentration of electrolytes in a medium surrounding the NPC (e.g., on the pH), these cationically chargeable species are in either in a cationically charged, or in a non-charged state.

In certain embodiments, a NPC provided herein has a net cationic charge at a pH of about 5. In some embodiments, a NPC described herein has a net neutral charge at about a neutral pH. In certain embodiments, a NPC described herein has a net cationic charge at about neutral pH (e.g., at a pH of about 7.4). In some embodiments, a NPC described herein has a greater net cationic charge at pH of about 5 than at a pH of about 7. In further or alternative embodiments, a NPC provided herein has a nominal (or absolute value of) charge that is greater at pH of about 5 than at a pH of about 7.

In certain embodiments, provided herein is a NPC wherein the form of the NPC is a micelle, a pseudo-micelle, or a micelle-like structure over the pH range of about 6 and up, about 6.5 and up, about 7 and up, about 6 to about 14, or more; about 6 to about 10, or more; about 6 to about 9.5, or more; about 6 to about 9, or more; about 6 to about 8.5, or more; about 6 to about 8, or more; about 6.5 to about 14, or more; about 6.5 to about 10, or more; about 6.5 to about 9.5, or more; about 6.5 to about 9, or more; about 6.5 to about 8.5, or more; about 7 to about 14, or more; about 7 to about 10, or more; about 7 to about 9.5, or more; about 7 to about 9, or more; about 7 to about 8.5, or more; about 6.2 to about 7.5, or more; 6.2 to 7.5; or about 7.2 to about 7.4. In certain embodiments, at a pH of about 7, or below; about 6.8, or below; about 6.5, or below; about 6.2, or below; about 6, or below; about 5.8, or below; or about 5.7, or below, the NPC, micelle, pseudo-micelle, or micelle-like structure provided herein become substantially, or at least partially disrupted or disassociated. In specific embodiments, the form of the NPC over the pH range of about 6.2 to 7.5 is a micelle. It is to be understood that as used herein, the NPC has a form over at least the pH described and may also have the described form at a pH outside the pH range described.

In certain embodiments, the "block copolymers" described herein comprise a core section and a shell section. As discussed herein, the core section optionally is or comprises a core block and the shell section optionally comprises or is a shell block. In some embodiments, at least one of such blocks is a gradient polymer block. In further embodiments, the block copolymer utilized herein is optionally substituted with a gradient polymer (i.e., the polymer utilized in the NPC is a gradient polymer having a core section and a shell section).

In certain embodiments, the NPC of the invention comprises a diblock copolymer. For example, in one embodiment the NPC comprises a diblock polymer comprising p(DMAEMA)-b-p(DMAEMA-co-BMA-co-PAA). In one embodiment, the shell block comprises p(DMAEMA). In one embodiment, the core block comprises p(DMAEMAco-BMA-co-PAA) copolymer. In certain embodiments, the NPC is a nanoparticle. In specific embodiments, the NPC is a micelle. In yet further embodiments, the NPC is a nanoparticle or micelle with the size of approximately 10 nm to about 200 nm, about 10 nm to about 100 nm, or about 30-80 nm. Particle size can be determined in any manner, including, but not limited to, by gel permeation chromatography (GPC), dynamic light scattering (DLS), electron microscopy techniques (e.g., TEM), and other methods.

In certain embodiments, the shell and/or shell block is hydrophilic and/or charged (e.g., non-charged, cationic, polycationic, anionic, polyanionic, or zwitterionic). In certain embodiments, the shell and/or shell block is hydrophilic and neutral (non-charged). In specific embodiments, the shell and/or shell block comprises a net positive charge. In specific embodiments, the shell and/or shell block comprises a net negative charge. In specific embodiments, the shell and/or shell block comprises a net neutral charge. In some embodiments, the core and/or core block is hydrophobic and/or comprises hydrophobic groups, moieties, monomeric units, species, or the like. In specific embodiments, the hydrophobic core and/or core block comprise a plurality of hydrophobic groups, moieties, monomeric units, species, or the like and a plurality of chargeable species or monomeric units. In more specific embodiments, the plurality of chargeable monomeric units or species comprises a plurality of anionic chargeable monomeric units or species. In more specific embodiments, the plurality of chargeable monomeric units or species comprises a plurality of cationic chargeable monomeric units or species. In still more specific embodiments, the plurality of chargeable monomeric units or species comprises a plurality of cationic and a plurality of anionic chargeable monomeric units or species. In some embodiments, the block copolymers each have (1) a hydrophilic, charged block (e.g., anionic or polyanionic; or cationic or polycationic; or zwitterionic; or non-charged) forming the shell of the NPC, (2) a hydrophobic block, and (3) a plurality of anionic chargeable species. In some embodiments, the plurality of anionic chargeable species is present in the hydrophobic block. In certain embodiments, the hydrophobic core and/or core block optionally comprise spacer monomeric units which may or may not comprise hydrophobic groups, chargeable groups, or a combination thereof. In some embodiments, a polymer block forming or present in the core of the NPC (e.g., one or more core block of the copolymer) is chargeable (e.g., contains cationic and/or anionic species at a physiological pH). In some instances, the NPC (e.g., micelles) provided herein are formed from a plurality of block copolymers which self-associate. In certain instances, the self-association occurs through the interactions of the hydrophobic blocks of the block copolymers and the resulting NPC (e.g., micelles) are stabilized through hydrophobic interactions of the hydrophobic blocks present in the core of the NPC.

In some embodiments, the NPC (e.g., micelles) provided herein retain activity (e.g., the activity of the NPC to deliver a therapeutic agent) in mammalian tissue (e.g. serum, plasma, saliva, soft tissue, etc) for at least 2 hours, at least 4 hours, at least 6 hours, at least 8 hours, at least 12 hours, or at least 24 hours.

In various embodiments, block copolymers utilized in the NPC (e.g., micelles) described herein have or are selected to have an influence on a certain aspect or functionality of the NPC (e.g., micelles) provided herein, including but not limited to: (1) the biophysical properties of the NPC such as, by way of non-limiting example, solubility, aqueous solubility, stability, stability in an aqueous medium, hydrophilicity, lipophilicity, hydrophobicity, or the like; (2) the facilitation of the formulation of the NPC into an administrable form, or other purposes; (3) the ability of the NPC to target a specific or selected type of cell or biostructure (e.g., by carrying a targeting moiety); and/or (4) the ability to increase biocompatibility of the NPC. In some embodiments, a NPC provided herein is characterized by one or more of the following: (1) the NPC is formed by spontaneous self association of block copolymers to form organized assemblies (e.g., micelles) upon dilution from a water-miscible solvent (such as but not limited to ethanol) to aqueous solvents (for example phosphate-buffered saline, pH 7.4); (2) the NPC is stable to dilution (e.g., down to a polymer concentration of 100 µg/ml, 50 µg/ml, 10 µg/ml, 5 µg/ml or 1 µg/ml, which constitutes the critical stability concentration or the critical micelle concentration (CMC)); (3) the NPC is stable to high ionic strength of the surrounding media (e.g. 0.5M NaCl); and/or (4) the NPC has an increasing instability as the concentration of organic solvent increases, such organic solvents including, but not limited to dimethylformamide (DMF), dimethylsulfoxide (DMS), and dioxane. In some embodiments, a NPC provided herein is characterized by having at least two of the aforementioned properties. In some embodiments, a NPC provided herein is characterized by having at least three of the aforementioned properties. In some embodiments, a NPC provided herein is characterized by having all of the aforementioned properties.

In certain embodiments, NPC provided herein are further or alternatively characterized by other criteria: (1) the molecular weight of the individual blocks and their relative length ratios is decreased or increased in order to govern the size of the NPC formed and its relative stability and (2) the size of the polymer cationic block that forms the shell is varied in order to provide effective complex formation with and/or charge neutralization of an anionic therapeutic agent.

Moreover, in certain embodiments, NPC provided herein selectively uptake small hydrophobic molecules, such as hydrophobic small molecule compounds (e.g., hydrophobic small molecule drugs) into the hydrophobic core of the NPC. In certain embodiments, the NPC provided herein comprise a therapeutic agent conjugated by way of linkers and/or tethers to one or more components of the NPC.

Block Copolymers

In specific embodiments, the core block of the block copolymers provided herein comprise a plurality of first chargeable groups, species, or monomeric units and a plurality of second chargeable species, groups, or monomeric units. In certain instances, the first chargeable groups, species or monomeric units are negatively charged or chargeable to a negative species, group, or monomeric unit. In some instances, the second chargeable groups, species, or monomeric units are positively charged or chargeable to cationic species, groups, or monomeric units. In certain embodiments, as the pH of an aqueous medium comprising a NPC described herein decreases, the core block of the block copolymers and the core of the NPC become more protonated resulting in a disruption of the shape and/or size of the NPC.

In certain embodiments, the NPC provided herein comprise a plurality of membrane-destabilizing block copolymers which destabilize an endosomal membrane in a pH-dependent manner. In various embodiments, the membrane-destabilizing block copolymers destabilize a membrane when assembled in the NPC and/or when present independent of the NPC form (e.g., when the micellic assemblies are disassociated and/or destabilized). In some embodiments, at or near physiological pH, the polymers making up the NPC are minimally membrane-destabilizing, but upon exposure to decreased pH, the polymer is membrane-destabilizing. In certain instances, this transition to a membrane-destabilizing state occurs via the protonation of weakly acidic residues that are incorporated into the polymers, such protonation leading to an increase in the hydrophobicity of the polymers. In certain instances, the increased hydrophobicity of the polymer results in a conformational change of the NPC, making the NPC membrane-destabilizing (e.g., causing destabilization of the membrane). In some embodiments, the mechanism of membrane destabilization of the NPC provided herein does not rely on a purely proton-sponge membrane destabilizing mechanism of polycations such as PEI or other polycations. In some embodiments, the combination of two mechanisms of membrane disruption, (a) a polycation (such as DMAEMA) and (b) a hydrophobized polyanion (such as propylacrylic acid), acting together have an additive or synergistic effect on the potency of the membrane destabilization conferred by the polymer.

In some embodiments, polymer blocks are optionally selected from, by way of non-limiting example, polynucleotides, oligonucleotides, polyethyleneglycols, hydrophilic block, hydrophobic blocks, charged blocks, or the like.

In certain embodiments, NPCs described herein comprise block copolymers, wherein the block copolymers are non-peptidic and/or non-lipidic. In some embodiments, the backbone of the block copolymers forming the NPC is non-peptidic and/or non-lipidic. In certain embodiments, the backbone of the core block is non-peptidic and/or non-lipidic. In some embodiments, the shell block is non-peptidic and/or non-lipidic. As used herein, lipids are a diverse group of compounds broadly defined as hydrophobic or amphiphilic molecules that originate entirely or in part from two distinct types of biochemical subunits: ketoacyl and isoprene groups, e.g., fatty acids, glycerolipids, glycerophoispholipids, sphingolipids, saccharolipids, polyketides, sterol lipids, and prenol lipids.

In some embodiments, provided herein is a NPC comprising a plurality of block copolymers comprising a core section (e.g., core block) and a shell section (e.g., shell block) wherein the ratio of the number average molecular weight of the core section (e.g., core block) to the number average molecular weight of the shell section (e.g., shell block) is present in any suitable ratio. In specific embodiments, block copolymers wherein the ratio of the number average molecular weight of the core section (e.g., core block) to the number average molecular weight of the shell section (e.g., shell block) is present in a ratio of about 1:10 to about 5:1, about 1:1 to about 5:1, about 5:4 to about 5:1, about 1:2 to about 2:1, about 2:1, about 1.5:1, about 1.1:1, about 1.2:1, about 1.3:1, about 1.4:1, about 1.6:1, about 1.7:1, about 1.8:1, about 1.9:1, or about 2.1:1. In some embodiments, block copolymers wherein the ratio of the number average molecular weight of the core section (e.g., core block) to the number average molecular weight of the shell section (e.g., shell block) is present in a ratio of about 2 (or more) to 1; about 1.5 (or more) to 1; about 1.1 (or more) to 1; about 1.2 (or more) to 1; about 1.3 (or more) to 1; about 1.4 (or more) to 1; about 1.6 (or more) to 1; about 1.7 (or more) to 1; about 1.8 (or more) to 1; about 1.9 (or more) to 1; or about 2.1 (or more) to 1. In specific embodiments, the ratio of the number average molecular weight of the core block to the number average molecular weight of the shell block is about 2:1.

In specific embodiments, the NPC provided herein comprises at least one type of polymer (e.g., block copolymers and/or monoblock polymers, including monoblock copolymers) having a hydrophilic segment and a hydrophobic segment. In certain embodiments, the hydrophilic segment is a hydrophilic block and the hydrophobic segment is a hydrophobic block. In some embodiments, these polymers are non-peptidic. In other embodiments, the hydrophilic segment and the hydrophobic segment are different regions of a monoblock gradient copolymer. In various instances, a "polymeric segment" is a polymer section with a given physical property (e.g., a physical property of a block described herein, e.g., hydrophobicity, hydrophilicity, chargeability, etc.) or which comprises one or more blocks with similar physical properties (e.g., hydrophobicity, hydrophilicity, chargeability, etc.).

In certain embodiments, one or more or all of the polymers of a NPC described herein each have (1) an optionally charged hydrophilic segment (e.g., a shell block) forming at least a portion of the shell of the NPC; and (2) a substantially hydrophobic segment (e.g., a core block) forming at least a portion of the hydrophobic core of the NPC which is stabilized through hydrophobic interactions of the core-forming polymeric segments. In some embodiments the hydrophilic segment is neutral or non-charged. In some embodiments the hydrophilic segment is charged and cationic, or polycationic. In some embodiments the hydrophilic segment is charged and anionic, or polyanionic. In some embodiments the hydrophilic segment is charged and zwitterionic. In some cases, the hydrophilic segment may serve at least three functions: (1) to form the shell of the NPC, (2) to increase the aqueous dispersability of the NPC, and (3) to attach to (e.g., bind) one or more therapeutic targets. In some embodiments, core block of the block copolymers and/or core of the NPC also comprise chargeable or charged species (e.g., anionic and/or cationic species/monomeric units at a physiological pH) and are membrane-destabilizing (e.g., membrane destabilizing in a pH dependent manner). In some embodiments, the substantially hydrophobic block (e.g., core block) and/or the core of the NPC comprises one or more chargeable species (e.g., monomeric unit, moiety, group, or the like). In more specific embodiments, the substantially hydrophobic block and/or core of the NPC comprise a plurality of cationic species and a plurality of anionic species. In still more specific embodiments, the core block of the block copolymers and/or core of the NPC comprises a substantially similar number of cationic and anionic species (i.e., the hydrophobic block and/or core are substantially net neutral).

In certain embodiments, a NPC provided herein comprises a hydrophobic core block comprising a first and a second chargeable species. In some embodiments, the first chargeable species is as described herein and the second chargeable species is chargeable to a cationic species upon protonation. In specific embodiments, the first chargeable species is non-charged at an acidic pH (e.g., an endosomal pH, a pH below about 6.5, a pH below about 6.0, a pH below about 5.8, a pH below about 5.7, or the like). In specific embodiments, the pKa of the second chargeable species is about 6 to about 10, about 6.5 to about 9, about 6.5 to about 8, about 6.5 to about 7.5, or any other suitable pKa. In certain embodiments, at least one of the first chargeable species and at least one of the second chargeable species are present on a single monomeric unit. In some embodiments, the first chargeable species is found on a first chargeable monomeric unit and the second chargeable species is on a second chargeable monomeric unit. In certain embodiments, the first chargeable species is chargeable to an anionic species upon deprotonation, the second chargeable species is chargeable to a cationic species upon protonation, and the ratio of the anionic species to the cationic species is between about 1:10 and about 10:1, about 1:6 and about 6:1, about 1:4 and about 4:1, about 1:2 and about 2:1, about 1:2 and 3:2, or about 1:1 at about a neutral pH. In some embodiments, the ratio of the first chargeable monomeric unit to the second chargeable monomeric unit is about 1:10 and about 10:1, about 1:6 and about 6:1, about 1:4 and about 4:1, about 1:2 and about 2:1, about 1:2 and 3:2, or about 1:1.

The term "copolymer", as used herein, signifies that the polymer is the result of polymerization of two or more different monomers. A "monoblock polymer" or a "subunit polymer" of a NPC described herein is a synthetic product of a single polymerization step. The term monoblock polymer includes a copolymer (i.e. a product of polymerization of more than one type of monomers) and a homopolymer (i.e., a product of polymerization of a single type of monomers). A "block" copolymer refers to a structure comprising one or more sub-combination of constitutional or monomeric units, used interchangeably herein. Such constitutional or monomeric units comprise residues of polymerized monomers. In some embodiments, a block copolymer described herein comprises non-lipidic constitutional or monomeric units. In some embodiments, the block copolymer is a diblock copolymer. A diblock copolymer comprises two blocks; a schematic generalization of such a polymer is represented by the following: $[A_aB_bC_c \ldots ]_m—[X_xY_yZ_z \ldots ]_n$, wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight of each block in the diblock copolymer. As suggested by the schematic, in some instances, the number and the nature of each constitutional unit is separately controlled for each block. The schematic is not meant and should not be construed to infer any relationship whatsoever between the number of constitutional units or the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the non-limiting form: x-x-y-z-x-y-y-z-y-z-z-z . . . . A non-limiting, exemplary alternating random configuration may have the non-limiting form: x-y-x-z-y-x-y-z-y-x-z . . . , and an exemplary regular alternating configuration may have the non-limiting form: x-y-z-x-y-z-x-y-z . . . . An exemplary regular block configuration may have the following non-limiting configuration: . . . x-x-x-y-y-y-z-z-z-x-x-x . . . , while an exemplary random block configuration may have the non-limiting configuration: . . . x-x-x-z-z-x-x-y-y-y-z-z-z-x-x-z-z-z- . . . , In a gradient polymer, the content of one or more monomeric units increases or decreases in a gradient manner from the a end of the polymer to the w end. In none of the preceding generic examples is the particular juxtaposition of individual constitutional units or blocks or the number of constitutional units in a block or the number of blocks meant nor should they be construed as in any manner bearing on or limiting the actual structure of block copolymers forming the micellic assembly of this invention. In certain embodiments, provided herein is any subunit polymer or composition of subunit polymers described herein, regardless of whether or not such polymers are assembled into a micellic assembly.

As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers. In some embodiments, the block copolymers are dendrimer, star or graft copolymers.

In certain embodiments, block copolymers the NPC provided herein comprise ethylenically unsaturated monomers. The term "ethylenically unsaturated monomer" is defined herein as a compound having at least one carbon double or triple bond. The non-limiting examples of the ethylenically unsaturated monomers are: an alkyl (alkyl)acrylate, a methacrylate, an acrylate, an alkylacrylamide, a methacrylamide, an acrylamide, a styrene, an allylamine, an allylammonium, a diallylamine, a diallylammonium, an N-vinyl formamide, a vinyl ether, a vinyl sulfonate, an acrylic acid, a sulfobetaine, a carboxybetaine, a phosphobetaine, or maleic anhydride.

In various embodiments, any monomer suitable for providing the polymers of the NPC described herein is used. In some embodiments, monomers suitable for use in the preparation of the polymers of the NPC provided herein include, by way of non-limiting example, one or more of the following monomers: methyl methacrylate, ethyl acrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, oligoethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), p-vinylbenzenesulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysillpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-arylmaleimide, N-phenylmaleimide, N-alkylmaleimide, N-butylimaleimide, N-vinylpyrrolidone, N-vinylcarbazole, butadiene, isoprene, chloroprene, ethylene, propylene, 1,5-hexadienes, 1,4-hexadienes, 1,3-butadienes, 1,4-pentadienes, vinylalcohol, vinylamine, N-alkylvinylamine, allylamine, N-alkylallylamine, diallylamine, N-alkyldiallylamine, alkylenimine, acrylic acids, alkylacrylates, acrylamides, methacrylic acids, alkylmethacrylates, methacrylamides, N-alkylacrylamides, N-alkylmethacrylamides, N-isopropylacrylamide, vinylnaphthalene, vinyl pyridine, ethylvinylbenzene, aminostyrene, vinylpyridine, vinylimidazole, vinylbiphenyl, vinylanisole, vinylimidazolyl, vinylpyridinyl, vinylpolyethyleneglycol, dimethylaminomethylstyrene, trimethylammonium ethyl methacrylate, trimethylammonium ethyl acrylate, dimethylamino propylacrylamide, trimethylammonium ethylacrylate, trimethylanunonium ethyl methacrylate, trimethylammonium propyl acrylamide, dodecyl acrylate, octadecyl acrylate, or octadecyl methacrylate monomers, or combinations thereof.

In some embodiments, functionalized versions of these monomers are optionally used. A functionalized monomer, as used herein, is a monomer comprising a masked or non-masked functional group, e.g. a group to which other moieties can be attached following the polymerization. The non-limiting examples of such groups are primary amino groups, carboxyls, thiols, hydroxyls, azides, and cyano groups. Several suitable masking groups are available (see, e.g., T. W. Greene & P. G. M. Wuts, Protective Groups in Organic Synthesis (2nd edition) J. Wiley & Sons, 1991. P. J. Kocienski, Protecting Groups, Georg Thieme Verlag, 1994)

Polymers described here are prepared in any suitable manner. Suitable synthetic methods used to produce the polymers provided herein include, by way of non-limiting example, cationic, anionic and free radical polymerization. In some instances, when a cationic process is used, the monomer is treated with a catalyst to initiate the polymerization. Optionally, one or more monomers are used to form a copolymer. In some embodiments, such a catalyst is an initiator, including, e.g., protonic acids (Bronsted acid) or Lewis acids, in the case of using Lewis acid some promoter such as water or alcohols are also optionally used. In some embodiments, the catalyst is, by way of non-limiting example, hydrogen iodide, perchloric acid, sulfuric acid, phosphoric acid, hydrogen fluoride, chlorosulfonic acid, methansulfonic acid, trifluoromehtanesulfonic acid, aluminum trichloride, alkyl aluminum chlorides, boron trifluoride complexes, tin tetrachloride, antimony pentachloride, zinc chloride, titanium tetrachloride, phosphorous pentachloride, phosphorus oxychloride, or chromium oxychloride. In certain embodiments, polymer synthesis is performed neat or in any suitable solvent. Suitable solvents include, but are not limited to, pentane, hexane, dichloromethane, chloroform, or dimethyl formamide (DMF). In certain embodiments, the polymer synthesis is performed at any suitable reaction temperature, including, e.g., from about −50° C. to about 100° C., or from about 0° C. to about 70° C.

In certain embodiments, the polymers are prepared by the means of a free radical polymerization. When a free radical polymerization process is used, (i) the monomer, (ii) optionally, the co-monomer, and (iii) an optional source of free radicals are provided to trigger a free radical polymerization process. In some embodiments, the source of free radicals is optional because some monomers may self-initiate upon heating at high temperature. In certain instances, after forming the polymerization mixture, the mixture is subjected to polymerization conditions. Polymerization conditions are those conditions that cause at least one monomer to form at least one polymer, as discussed herein. Such conditions are optionally varied to any suitable level and include, by way of non-limiting example, temperature, pressure, atmosphere, ratios of starting components used in the polymerization mixture and reaction time. The polymerization is carried out in any suitable manner, including, e.g., in solution, dispersion, suspension, emulsion or bulk.

In some embodiments, initiators are present in the reaction mixture. Any suitable initiators is optionally utilized if useful in the polymerization processes described herein. Such initiators include, by way of non-limiting example, one or more of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, or azo compounds. In specific embodiments, benzoylperoxide (BPO) and/or AlBN are used as initiators.

In some embodiments, polymerization processes are carried out in a living mode, in any suitable manner, such as but not limited to Atom Transfer Radical Polymerization (ATRP), nitroxide-mediated living free radical polymerization (NMP), ring-opening polymerization (ROP), degenerative transfer (DT), or Reversible Addition Fragmentation Transfer (RAFT). Using conventional and/or living/controlled polymerizations methods, various polymer architectures can be produced, such as but not limited to block, graft, star and gradient copolymers, whereby the monomer units are either distributed statistically or in a gradient fashion across the chain or homopolymerized in block sequence or pendant grafts. In other embodiments, polymers are synthesized by Macromolecular design via reversible addition-fragmentation chain transfer of Xanthates (MADIX) (Direct Synthesis of Double Hydrophilic Statistical Di- and Triblock Copolymers Comprised of Acrylamide and Acrylic Acid Units via the MADIX Process", Daniel Taton, et al., Macromolecular Rapid Communications, 22, No. 18, 1497-1503 (2001).)

In certain embodiments, Reversible Addition-Fragmentation chain Transfer or RAFT is used in synthesizing ethylenic backbone polymers of this invention. RAFT is a living polymerization process. RAFT comprises a free radical degenerative chain transfer process. In some embodiments, RAFT procedures for preparing a polymer described herein employs thiocarbonylthio compounds such as, without limitation, dithioesters, dithiocarbamates, trithiocarbonates and xanthates to mediate polymerization by a reversible chain transfer mechanism. In certain instances, reaction of a polymeric radical with the C=S group of any of the preceding compounds leads to the formation of stabilized radical intermediates. Typically, these stabilized radical intermediates do not undergo the termination reactions typical of standard radical polymerization but, rather, reintroduce a radical capable of re-initiation or propagation with monomer, reforming the C=S bond in the process. In most instances, this cycle of addition to the C=S bond followed by fragmentation of the ensuing radical continues until all monomer has been consumed or the reaction is quenched. Generally, the low concentration of active radicals at any particular time limits normal termination reactions.

In some embodiments, polymers utilized in the NPC provided herein have a low polydispersity index (PDI) or differences in chain length. Polydispersity index (PDI) can be determined in any suitable manner, e.g., by dividing the weight average molecular weight of the polymer chains by their number average molecular weight. The number average molecule weight is sum of individual chain molecular weights divided by the number of chains. The weight average molecular weight is proportional to the square of the molecular weight divided by the number of molecules of that molecular weight. Since the weight average molecular weight is always greater than the number average molecular weight, polydispersity is always greater than or equal to one. As the numbers come closer and closer to being the same, i.e., as the polydispersity approaches a value of one, the polymer becomes closer to being monodisperse in which every chain has exactly the same number of constitutional units. Polydispersity values approaching one are achievable using radical living polymerization. Methods of determining polydispersity, such as, but not limited to, size exclusion chromatography, dynamic light scattering, matrix-assisted laser desorption/ionization chromatography and electrospray mass chromatography are well known in the art. In some embodiments, block copolymers (e.g., membrane destabilizing block copolymers) of the micellic assemblies (e.g., micelles) provided herein have a polydispersity index (PDI) of less than 2.0, or less than 1.8, or less than 1.6, or less than 1.5, or less than 1.4, or less than 1.3, or less than 1.2.

Polymerization processes described herein optionally occur in any suitable solvent or mixture thereof. Suitable solvents include water, alcohol (e.g., methanol, ethanol, n-propanol, isopropanol, butanol), tetrahydrofuran (THF) dimethyl sulfoxide (DMSO), dimethylformamide (DMF), acetone, acetonitrile, hexamethylphosphoramide, acetic acid, formic acid, hexane, cyclohexane, benzene, toluene, dioxane, methylene chloride, ether (e.g., diethyl ether), chloroform, and ethyl acetate. In one aspect, the solvent includes water, and mixtures of water and water-miscible organic solvents such as DMF.

In certain embodiments, poly(DMAEMA) and other polymeric entities used herein (e.g., copolymers or copolymer blocks of BMA, DMAEMA and PAA) are prepared in any suitable manner. In one embodiment, poly(DMAEMA) is prepared by polymerizing DMAEMA in the presence of the RAFT CTA, ECT, and a radical initiator. In some embodiments, a block, poly(DMAEMA) macroCTA is used to prepare a series of diblock copolymers where the second block contained BMA, DMAEMA and PAA. In other specific embodiments, the orientation of the blocks on the diblock polymer is reversed, such that upon self-assembly, the w end of the polymer is exposed on the hydrophilic segment of the NPC. In various embodiments, this is achieved in any suitable manner, including a number of ways synthetically. For example, in some embodiments, the synthesis of the block copolymers described herein begins with the preparation of the PAA/BMA/DMAEMA core-forming hydrophobic block, and the shell-forming hydrophilic, charged block is added in the second synthetic step by subjecting the resulting PAA/BMA/DMAEMA macroCTA to a second RAFT polymerization step. Alternate approaches include reducing the PAA/BMA/DMAEMA macroCTA to form a thiol end and then covalently attaching a pre-formed hydrophilic, charged polymer to the formed thiol. This synthetic approach provides a method for introduction of a reactive group on the w-end of the polymeric chain exposed to the surface of NPC thus providing alternate approaches to chemical conjugation to the NPC.

In some embodiments, block copolymers are synthesized by chemical conjugation of several polymer blocks that are prepared by separate polymerization processes.

In some instances, the block copolymers comprise monomers bearing reactive groups which can be used for post-polymerization introduction of additional functionalities via know in the art chemistries, for example, "click" chemistry (for example of "click" reactions, see Wu, P.; Fokin, V. V. Catalytic Azide-Alkyne Cycloaddition: Reactivity and Applications. *Aldrichim. Acta,* 2007, 40, 7-17).

Exemplary block polymers useful in the present invention are described in U.S. Patent Application Publication No. US2011/0123636, which is incorporated herein by reference.

Core

Provided in certain embodiments herein, the core of a NPC described herein comprises a plurality of pH dependent hydrophobes. In certain embodiments, the core of a NPC described herein is held together at least partially, substantially, or predominantly by hydrophobic interactions.

In some embodiments, the core of a NPC described herein comprises a plurality of first chargeable species. In specific embodiments, the first chargeable species are charged or chargeable to an anionic species. It is to be understood that none, some, or all of the first chargeable species within the core are charged.

In certain embodiments, the core block of a polymer described herein comprises a plurality of first chargeable species, and a plurality of second chargeable species. In some instances, the first chargeable species is charged or chargeable to an anionic species; and the second chargeable species is charged or chargeable to a cationic species. In some embodiments, the core of a NPC described herein comprises a plurality of first chargeable species; a plurality of second chargeable species; and a plurality of hydrophobic species.

In certain embodiments, where the core comprises a plurality of anionic chargeable species and a plurality of cationic chargeable species, the ratio of the number of the plurality of anionic chargeable species to the number of the plurality of cationic chargeable species is about 1:10 to about 10:1, about 1:8 to about 8:1, about 1:6 to about 6:1, about 1:4 to about 4:1, about 1:2 to about 2:1, about 3:2 to about 2:3, or is about 1:1.

In some embodiments, the core comprises a plurality of anionic chargeable species that are anionically charged and a plurality of cationically chargeable species that is cationically charged, wherein the ratio of the number of anionically charged species to the number of cationically charged species present in the core is about 1:10 to about 10:1, about 1:8 to about 8:1, about 1:6 to about 6:1, about 1:4 to about 4:1, about 1:2 to about 2:1, about 3:2 to about 2:3, or is about 1:1.

In some embodiments, the ratio, at about a neutral pH (e.g., at a pH of about 7.4), of the number of the plurality of anionic chargeable species to the number of the plurality of cationic chargeable species is about 1:10 to about 10:1, about 1:8 to about 8:1, about 1:6 to about 6:1, about 1:4 to about 4:1, about 1:2 to about 2:1, about 2:3 to about 3:2, about 1:1.1 to about 1.1:1, or is about 1:1. In some embodiments, the core comprises a plurality of anionic chargeable species that is anionically charged and a plurality of cationically chargeable species that is cationically charged, wherein the ratio, at about a neutral pH (e.g., at a pH of about 7.4), of the number of anionically charged species to the number of cationically charged species present in the core is about 1:10 to about 10:1, about 1:8 to about 8:1, about 1:6 to about 6:1, about 1:4 to about 4:1, about 1:2 to about 2:1, about 2:3 to about 3:2, about 1:1.1 to about 1.1:1, or is about 1:1. In specific embodiments, the ratio of positively charged species present in the core to negatively charged species in the core is about 1:4 to about 4:1 at about neutral pH. In more specific embodiments, the ratio of positively charged species present in the core to negatively charged species in the core is about 1:2 to about 2:1 at about neutral pH. In specific embodiments, the ratio of positively charged species present in the core to negatively charged species in the core is about 1:1.1 to about 1.1:1 at about neutral pH.

In specific embodiments, the first chargeable species is Bronsted acid. In certain instances, as used herein, a chargeable species includes species wherein addition or removal of a proton (e.g., in a pH dependent manner), provides a cationic or anionic, respectively, species, group, or monomeric unit.

In some embodiments, the first chargeable species present in the core are species that are at least 50%, at least 60%, at least 70%, at least 80%, at least 85%, or at least 95% negatively charged at about neutral pH (e.g., at a pH of about 7.4). In specific embodiments, these first chargeable species are charged by loss of a $H^+$, to an anionic species at about neutral pH. In further or alternative embodiments, the first chargeable species present in the core are species that are at least 20%, at least 30%, at least 40%, at least 50%, at least 60%, at least 70%, at least 80%, at least 85%, or at least 95% neutral or non-charged at a slightly acidic pH (e.g., a pH of about 6.5, or less; about 6.2, or less; about 6, or less; about 5.9, or less; about 5.8, or less; or about endosomal pH).

In some embodiments, the first chargeable species is, by way of non-limiting example, a carboxylic acid, anhydride, sulfonamide, sulfonic acid, sulfinic acid, sulfuric acid, phosphoric acid, phosphinic acid, boric acid, phosphorous acid, or the like.

In some embodiments, the second chargeable species present in the core are species that are at least 20%, at least 30%, at least 40%, at least 50%, at least 60%, at least 70%, at least 80%, at least 85%, or at least 95% positively charged at about neutral pH (e.g., at a pH of about 7.4). In specific embodiments, these second chargeable species are charged by addition of an $H^+$, to a cationic species. In further or alternative embodiments, the second chargeable species present in the core are species that are at least 20%, at least 30%, at least 40%, at least 50%, at least 60%, at least 70%, at least 80%, at least 85%, or at least 95% positively charged at a slightly acidic pH (e.g., a pH of about 6.5, or less; about 6.2, or less; about 6, or less; about 5.9, or less; about 5.8, or less; or about endosomal pH).

Shell

In some embodiments, the shell of a NPC described herein is hydrophilic. In specific embodiments, the shell of a NPC described herein comprises a plurality of chargeable species. In specific embodiments, the chargeable species is charged or chargeable to a cationic species. In other specific embodiments, the chargeable species is charged or chargeable to an anionic species. In other embodiments, the shell of the NPC is hydrophilic and non-charged (e.g., substantially non-charged). It is to be understood that such shell blocks include species wherein none, some, or all of the chargeable species are charged.

In specific embodiments, the shell of a NPC described herein is polycationic at about neutral pH (e.g., at a pH of about 7.4). In some embodiments, the chargeable species in the shell of a NPC are species, groups, or monomeric units that are at least 20%, at least 30%, at least 40%, at least 50%, at least 60%, at least 70%, at least 80%, at least 85%, or at least 95% positively charged at about neutral pH (e.g., at a pH of about 7.4). In specific embodiments, these chargeable species in the shell of a NPC are charged by addition of an $H^+$, to a cationic species (e.g., a Bronsted base). In further or alternative embodiments, the chargeable species in the shell of a NPC described herein are species that are at least 20%, at least 30%, at least 40%, at least 50%, at least 60%, at least 70%, at least 80%, at least 85%, or at least 95% positively charged at a slightly acidic pH (e.g., a pH of about 6.5, or less; about 6.2, or less; about 6, or less; about 5.9, or less; about 5.8, or less; or about endosomal pH).

In some embodiments, the shell of a NPC described herein is cationic at or near physiological pH (e.g., the pH of circulating human plasma). In some embodiments, the shell block is polycationic. In some embodiments, the shell comprises one or more therapeutic agents, wherein the therapeutic agents are polyanionic. In some embodiments, the plurality of therapeutic agents comprise a total of x anions, and the polycationic shell of a NPC described herein comprises about 0.6x, about 0.7x, about 0.8x, about 0.9x, about 1.0x, about 1.1xcations, or more.

In some embodiments, the shell of a NPC described herein is hydrophilic and non-charged. Hydrophilic, non-charged species useful herein include, by way of non-limiting example, polyethylene glycol (PEG), polyethylene oxide (PEO), or the like.

In certain embodiments, the shell of a NPC described herein comprises a plurality of different hydrophilic species (e.g., at least one non-charged hydrophilic species and at least one charged hydrophilic species).

Particle Size

In certain embodiments, the NPC provided herein is a nanoparticle having any suitable size. Size of the nanoparticles is adjusted to meet specific needs by adjusting the degree of polymerization of the core sections, shell sections, additional sections, or a combination thereof. In specific embodiments, a NPC provided herein has an average hydrodynamic diameter of about 10 nm to about 200 nm. In more specific embodiments, the NPC provided herein has an average hydrodynamic diameter of about 1 nm to about 500 nm, about 5 nm to about 250 nm, about 10 nm to about 200 nm, about 10 nm to about 100 nm, about 20 nm to about 100 nm, about 30 nm to about 80 nm, or the like in an aqueous medium. In still more specific embodiments, a NPC provided herein has an average hydrodynamic diameter of about 1 nm to about 500 nm, about 5 nm to about 250 nm, about 10 nm to about 200 nm, about 10 nm to about 100 nm, about 20 nm to about 100 nm, about 30 nm to about 80 nm, or the like in an aqueous medium with about a neutral pH (e.g., a pH of about 7.4). In some embodiments, a NPC provided herein has an average hydrodynamic diameter of about 1 nm to about 500 nm, about 5 nm to about 250 nm, about 10 nm to about 200 nm, about 10 nm to about 100 nm, about 20 nm to about 100 nm, about 30 nm to about 80 nm, or the like in human serum. In some embodiments, a NPC provided herein has an average hydrodynamic diameter of about 1 nm to about 500 nm, about 5 nm to about 250 nm, about 10 nm to about 200 nm, about 10 nm to about 100 nm, about 20 nm to about 100 nm, about 30 nm to about 80 nm, or the like in human saliva.

Assembly

In some embodiments, a NPC provided herein is self-assembled. In certain embodiments, the NPC is self-assembled or is capable of being self-assembled in an aqueous medium. In some embodiments, the NPC is self-assembled or is capable of being self-assembled in an aqueous medium having about neutral pH (e.g., having a pH of about 7.4). In some embodiments, the NPC is self-assembled or is capable of being self-assembled upon dilution of an organic solution of the block copolymers with an aqueous medium having about neutral pH (e.g., having a pH of about 7.4). In some embodiments, the NPC is self-assembled or is capable of being self-assembled in human serum. In some embodiments, the NPC is self-assembled or is capable of being self-assembled in human saliva. In some embodiments, a NPC provided herein is self-assembled.

In specific embodiments, a NPC provided herein self-assembles in an aqueous medium at least one pH value within about 6 to about 9, about 6 to about 8, about 6.5 to about 9, about 6.5 to about 8, about 6.5 to about 7.5, about 7 to about 9, or about 7 to about 8. It is to be understood that as used herein, the micellic assemblies self assemble at least the pH described herein, but may also self assemble at one or more pH values outside the pH range described.

In some embodiments, a NPC provided herein self-assembles at any suitable concentration. In certain embodiments, a NPC provided herein self-assembles (e.g., has a critical assembly concentration (CAC), or the minimum concentration at which a NPC forms) of about 2 µg/mL, about 5 µg/mL, about 8 µg/mL, about 10 µg/mL, about 20 µg/mL, about 25 µg/mL, about 30 µg/mL, about 40 µg/mL, about 50 µg/mL, about 60 µg/mL, about 70 µg/mL, about 80 µg/mL, about 90 µg/mL, about 100 µg/mL, or greater. In certain embodiments, a NPC provided herein self assembles at least one concentration between about 1 µg/mL and about 100 µg/mL.

In some embodiments, the NPC provided herein are prepared by spontaneous self-assembly of the polymers described herein. In certain embodiments, the polymers described herein assemble into the NPC provided herein upon (a) dilution of a solution of the polymer in water-miscible organic solvent into aqueous media; or (b) being dissolved directly in an aqueous solution. In some embodiments, the polymers described herein assemble into the NPC provided herein in the absence of therapeutic agent.

In some embodiments, the NPC are stable to dilution in an aqueous solution. In specific embodiments, the NPC are stable to dilution at physiologic pH (including the pH of blood or saliva of a human) with a critical stability concentration (e.g., a critical micelle concentration (CMC)) of approximately 50 to approximately 100 µg/mL, or approximately 10 to approximately 50 µg/mL, less than 10 µg/mL, less than 5 µg/mL, or less than 2 µg/mL. As used herein, "destabilization of a NPC" means that the polymeric chains forming a NPC at least partially disaggregate, structurally alter (e.g., expand in size and/or change shape), and/or may form amorphous supramolecular structures (e.g., non-micellic supramolecular structures). The terms critical stability concentration (CSC), critical micelle concentration (CMC), and critical assembly concentration (CAC) are used interchangeably herein.

Stability

In some embodiments, a NPC provided herein is stable in an aqueous medium. In certain embodiments, a NPC provided herein is stable in an aqueous medium at a selected pH, e.g., about physiological pH (e.g., the pH of blood or saliva of a human). In specific embodiments, a NPC provided herein is stable at about a neutral pH (e.g., at a pH of about 7.4) in an aqueous medium. In certain embodiments, a NPC provided herein is stable in mammalian serum, mammalian plasma, and/or mammalian saliva. It is to be understood that stability of the NPC is not limited to designated pH, but that it is stable at pH values that include, at a minimum, the designated pH. In specific embodiments, a NPC described herein is substantially less stable at an acidic pH than at a pH that is about neutral. In more specific embodiments, a NPC described herein is substantially less stable at a pH of about 5.8 than at a pH of about 7.4.

In specific embodiments, the NPC is stable at a concentration of about 10 µg/mL, or greater (e.g., at about a neutral pH). In some embodiments, the NPC is stable at a concentration of about 100 µg/mL, or greater (e.g., at about a neutral pH).

Shielding Hydrophilic Segment/Block

In certain embodiments, the NPC described herein comprise one or more shielding agents. In some embodiments, the polynucleotide carrier block/segment comprises a PEG substituted monomeric unit (e.g., the PEG is a side chain and does not comprise the backbone of the polynucleotide carrier block). In some instances, one or more of the polymers (e.g., block copolymers) utilized in the micellic assemblies described herein comprise polyethyleneglycol (PEG) chains or blocks with molecular weights of approximately from 1,000 to approximately 30,000. In some embodiments, PEG is conjugated to polymer ends groups, or to one or more pendant modifiable group present in a polymer of a NPC provided herein. In some embodiments, PEG residues are conjugated to modifiable groups within the hydrophilic segment or block (e.g., a shell block) of a polymer (e.g., block copolymer) of a NPC provided herein. In certain embodiments, a monomer comprising a PEG residue of 2-20 ethylene oxide units is co-polymerized to form the hydrophilic portion of the polymer forming a NPC provided herein.

In some instances a shielding agent enhances the stability of the therapeutic agent against enzymatic digestion. In some instances, a shielding agent reduces toxicity of NPC described herein. In some embodiments, a shielding agent comprises a plurality of neutral hydrophilic monomeric residues. In some instances, a shielding polymer is covalently coupled to a membrane destabilizing block copolymer through an end group of the polymer. In some embodiments, a shielding agent is a covalently coupled pendant moiety attached to one or more monomeric residues of the polymer. In some embodiments, a plurality of monomeric residues in a NPC described herein comprise pendant shielding species (e.g., a polyethylene glycol (PEG) oligomer (e.g., having 20 or less repeat units) or polymer (e.g, having more than 20 repeat units)) covalently coupled through a functional group to the polyethylene glycol oligomer or polymer. In some instances, a block copolymer comprises a polyethylene gylcol (PEG) oligomer or polymer covalently coupled to the alpha end or the omega end of the membrane destabilizing block of the copolymer.

Degradable Tethers

In certain embodiments, the NPC described herein comprise one or more linkages and/or tethers that attach one or more therapeutic agents to one or more polymers of the NPC. In certain embodiments, the linkages and/or tethers are degradable such that they are degraded when the shape or structure of the NPC is disrupted. In specific embodiments, the linkages and/or tethers are degradable such that they are degraded when the shape or structure of the NPC is disrupted due to the local pH. For example, in one embodiment, the linkages and/or tethers are degraded when the shape or structure of the NPC is disrupted due to the acidic environment. Degradation of the linkages and/or tethers releases the therapeutic agent from the NPC into the target tissue. In certain embodiments, the rate of degradation, and thereby the rate of release of the agent, is dependent upon the structure and length of the tether, and the pH of the local environment.

In one embodiment, the linkages and/or tethers comprise lactic acid (LA). The LA is hydrolytically degradable upon exposure to the environment (i.e. when the NPC is disassembled). In one embodiment, the tether of the NPC comprises 1-30 LA repeats. In another embodiment, the tether comprises 1-10 LA repeats. The tether is not limited to compositions comprising LA, but rather encompasses any hydrolytically degradable units, including, but not limited to, poly(lactide-co-glycolide) (PLG). In one embodiment, the rate of the release of the therapeutic agent is controlled by the number of LA repeats within the degradable tether. For example, in certain embodiments, the rate of release is increased as the number of repeats is increased. In other embodiments, the rate of release is increased as the number of repeats is decreased. Further description of degradable tethers are described in Benoit et al., 2007, Adv Funct Mater, 17(13): 2085-2093 and Benoit et al., 2006, Biomaterials, 27(36): 6102-6110, each of which are incorporated herein by reference.

Therapeutic Agents

Provided in certain embodiments herein is a NPC comprising at least one research reagent, at least one diagnostic agent, at least one therapeutic agent, or a combination thereof. In some embodiments, such therapeutic agents are present in the shell of the NPC, in the core of the NPC, on the surface of NPC, or a combination thereof.

In various embodiments, research reagents, diagnostic agents, and/or therapeutic agents are attached to the NPC or block copolymers thereof in any suitable manner. In specific embodiments, attachment is achieved through covalent bonds, non-covalent interactions, static interactions, hydrophobic interactions, or the like, or combinations thereof. In some embodiments, the research reagents, diagnostic agents, and/or therapeutic agents are attached to a shell block of block copolymers. In certain embodiments, the research reagents, diagnostic agents, or therapeutic agents form the shell block of a block copolymer. In some embodiments, the research reagents, diagnostic agents, or therapeutic agents are in the shell of the NPC. In some embodiments, the research reagents, diagnostic agents, and/or therapeutic agents are attached to a core block of block copolymers. In certain embodiments, the research reagents, diagnostic agents, or therapeutic agents form the core block of a block copolymer. In some embodiments, the research reagents, diagnostic agents, or therapeutic agents are in the core of the NPC.

In some embodiments, provided herein is a NPC comprising a first therapeutic agent in the shell of the NPC and a second therapeutic agent in the core of the NPC.

In certain embodiments, provided herein is a NPC comprising at least 1-5, 5-250, 5-1000, 250-1000, at least 2, at least 5, at least 10, at least 20, or at least 50 therapeutic agents. In some embodiments, provided herein is a composition comprising a plurality of NPC described herein, wherein the NPC therein comprise, on average, at least 1-5, 5-250, 5-1000, 250-1000, at least 2, at least 5, at least 10, at least 20, or at least 50 therapeutic agents.

In some embodiments, therapeutic agents, diagnostic agents, etc., are selected from, by way of non-limiting example, at least one nucleotide (e.g., a polynucleotide), at least one carbohydrate or at least one amino acid (e.g., a peptide). In specific embodiments, the therapeutic agent is a polynucleotide, an oligonucleotide, a gene expression modulator, a knockdown agent, an siRNA, an RNAi agent, a dicer substrate, an miRNA, an shRNA, an antisense oligonucleotide, or an aptamer. In other specific embodiments, the therapeutic agent is an aiRNA (Asymmetric RNA duplexes mediate RNA interference in mammalian cells. Xiangao Sun, Harry A Rogoff, Chiang J Li Nature Biotechnology 26, 1379-1382 (2008)). In certain embodiments, the therapeutic agent is a protein, peptide, dominant-negative protein, enzyme, antibody, or antibody fragment. In some embodiments, the therapeutic agent is a carbohydrate, or a small molecule.

In certain embodiments, one or more of the plurality of block copolymers is attached to a therapeutic agent. In some embodiments, one or more of the plurality of block copolymers is attached to a first therapeutic agent, and wherein one or more of the plurality of block copolymers is attached to a second therapeutic agent.

In some embodiments, a therapeutic agent is chemically conjugated to the NPC and/or to one or more polymer of the NPC by any suitable chemical conjugation technique. Therapeutic agents are optionally conjugated to an end of the polymer, or to a pendant side chain of the polymer. In some embodiments, NPC containing a therapeutic agent are formed by conjugation of the agent with an already formed NPC comprising a plurality of polymers (e.g., block copolymers). In other embodiments, NPC containing a therapeutic agent are formed by conjugation of the agent with a polymer and subsequently forming the NPC in any suitable manner, e.g., by self assembly of the resulting conjugates into a NPC comprising the agent. In various embodiments, such a NPC optionally further comprises unconjugated polymers (e.g., block copolymers) that are similar, identical, or different than those conjugated to the agent. The covalent bond between a polymer and a therapeutic agent of a NPC described herein is, optionally, non-cleavable, or cleavable. In certain embodiments, a precursor of one or more agent is attached to the NPC or to the polymeric units of NPC. In some embodiments, one or more agent is attached through a cleavable bond. In certain embodiments, the cleavable bonds utilized in the NPC described herein include, by way of non-limiting example, disulfide bonds (e.g., disulfide bonds that dissociate in the reducing environment of the cytoplasm). In some embodiments, covalent association between a NPC (including the components thereof) and a therapeutic agent is achieved through any suitable chemical conjugation method, including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In some embodiments, conjugation is also performed with pH-sensitive bonds and linkers, including, but not limited to, hydrazone and acetal linkages. Any other suitable conjugation method is optionally utilized as well, for example a large variety of conjugation chemistries are available (see, for example, Bioconjugation, Aslam and Dent, Eds, Macmillan, 1998 and chapters therein).

In some embodiments, any NPC described herein further comprises an additional polymer that is not attached to a therapeutic agent. In some embodiments, the additional polymer is a diluent polymer or a targeting moiety carrier polymer. In certain embodiments, any NPC provided herein further comprises an additional polymer that is attached to at least one second therapeutic agent (e.g., a second therapeutic agent). In certain embodiments, the at least one second therapeutic agent (e.g., second therapeutic agent) is different from the at least one therapeutic agent (e.g., a first therapeutic agent). In some embodiments, the core portion (e.g., core blocks) of all polymers present in the micellic assembly are similar or identical. In certain embodiments, one or more different polymer in the micellic assembly comprises similar or identical core portions (e.g., core blocks), but different non-core portions (e.g., shell blocks).

The NPC described herein comprises any suitable therapeutic agent that is deliverable to a target tissue to have an effect on the target tissue or on the subject. Exemplary therapeutic agents include, but are not limited to, antibiotics, antivirals, antimicrobials, anti-infective agents, anti-fungal agents, anti-biofilm agents, hormones, antibodies, small molecules, vitamins, minerals, polypeptides, enzymes, nucleic acids, chemotherapeutic agents, anti-inflammatory agents, immunomodulators, anesthetics, analgesics, and the like.

In certain embodiments, the NPC described herein comprises at least one anti-biofilm agent. It is described herein that NPC surprisingly binds to all relevant surfaces within biofilms and regions at risk for biofilm formation. As such, in certain embodiments, the NPC described herein is homed to sites with biofilms and regions at risk for biofilm formation and/or accumulation, and, when triggered for release, releases an anti-biofilm agent locally at those sites. Anti-biofilm agents include, but are not limited to, apigenin and derivatives thereof; flavonoids including flavones, flavonols, dihydroflavonols, flavonones, and derivatives thereof; farnesol and derivatives thereof; terpenoids including terpenes, terpinols, diterpenic acids, diterpenes, triterpenes, and derivatives therof; biofilm degrading enzymes including mutanase, dextranase, and amyloglucosidade-glucose oxidase; and EPS-synthesizing enzyme inhibitors including Rose Bengal, Perborate, meta-periodate, sorbitol, xylitol, 1-deoxynojirimycin, flavonoids, polyphenols, proanthocyanidins, tannins, and coumarins.

In certain embodiments, the NPC described herein comprises at least one antibacterial agent. In one embodiment, the antibacterial agent is a broad-spectrum antibacterial agent. Suitable antibacterial agents include, but are not limited to, chlorhexidine and derivatives thereof, members of the bisbiguanide class of inhibitors, povidone iodine, hydrogen peroxide, doxycycline, minocycline, clindamycin, doxycycline, metronidazole, essential oil extracts (menthol, thymol, eucalyptol, methyl salicylate, metal salts (zinc, copper, stannous ions), phenols (triclosan), all quaternary ammonium compounds (cetylpyridinium chloride), surfactants (sodium lauryl sulphate, delmopinol), all natural molecules (phenols, phenolic acids, quinones, alkaloids, lectins, peptides, polypeptides, indole derivatives, flustramine derivatives, carolacton, halogenated furanones, oroidin analogues, agelasine, ageloxime D).

In another embodiment, the NPC described herein comprises fluoride. Fluoride can be included as any one of its formulations including, but not limited to sodium fluoride, monofluorophosphate and its derivatives, and stannous fluoride.

In certain embodiments, the NPC of the invention comprises a therapeutically effective amount of at least one therapeutic agent. For example, in one embodiment, the core of the NPC is loaded with a therapeutically effective amount of at least one therapeutic agent. The relative amount or concentration of the therapeutic agent may be dependent upon the size of the NPC, type of therapeutic agent, condition to be treated or prevented, and the like. In one embodiment, the therapeutic agent is present at greater than about 0 wt %, or greater than about 5 wt %, or greater than about 10 wt %, or greater than about 15 wt %, or greater than about 20 wt %, or greater than about 30 wt %, or greater than about 50 wt %, or greater than about 75 wt %. For example, it is demonstrated herein that the NPC of the invention may loaded with an amount or concentration of a therapeutic agent that is much greater than its minimum effective concentration. Thus, the composition of the invention is able to retain therapeutically effective amounts of a therapeutic agent within the NPC.

In certain embodiments, the composition comprises a plurality of different NPCs, each carrying a different therapeutic agent, thereby providing combination therapy. For example, in one embodiment, the composition comprises a first NPC, comprising an anti-biofilm agent, and a second NPC, comprising fluoride. In another embodiment, the composition comprises a first NPC, comprising an anti-biofilm agent, a second NPC, comprising a broad-spectrum antibiotic, and a third NPC, comprising fluoride. Each therapeutic agent has different yet complementary mechanisms of action, all aimed at treating the pathology; anti-biofilm agent will prevent biofilm formation, antibacterial agent will kill the bad bacteria and fluoride will rebuild the mineral. In one embodiment, the different NPCs are mixed in different proportions to achieve maximum therapeutic effect. In one embodiment, each of the different NPCs can be configured for different drug delivery characteristics, thereby allowing different therapeutic agents to be delivered at different times, as necessitated by the particular disorder or treatment.

Pharmaceutical Compositions and Formulations

The invention also encompasses the use of pharmaceutical compositions of the invention or salts thereof to practice the methods of the invention. Such a pharmaceutical composition may consist of at least one compound, agent, NPC, or NPC conjugate of the invention or a salt thereof in a form suitable for administration to a subject, or the pharmaceutical composition may comprise at least one compound, agent, NPC, or NPC conjugate of the invention or a salt thereof, and one or more pharmaceutically acceptable carriers, one or more additional ingredients, or some combination of these. The compound, agent, NPC, or NPC conjugate of the invention may be present in the pharmaceutical composition in the form of a physiologically acceptable salt, such as in combination with a physiologically acceptable cation or anion, as is well known in the art.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound, agent, NPC, or NPC conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

In certain embodiments, the composition of the invention is incorporated into a pharmaceutical composition suitable for topical application along the teeth of a subject. For example, in one embodiment, the NPC described herein, is incorporated into a paste (i.e. toothpaste), mouthwash, gel, chewing gum, dissolvable strips, patches, foams, and the like. In another embodiment, the NPC described herein are incorporated into dental materials for restoration, such as resins and/or composites. In another embodiment, the NPC described herein are incorporated into dental materials for cavity prevention, such as dental varnishes and dental sealants.

In certain embodiments, the composition of the invention is coated upon implantable materials to prevent the formation and/or accumulation of biofilm on the implantable material. For example, in one embodiment, the NPC described herein is coated on implants including, but not limited to orthopedic implants (e.g. plates, screws, artificial joints, etc.), tissue engineered substrates, pacemakers, heart pumps, insulin pumps, breathing tubes, central line catheters, and indwelling catheters.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, chewing gum, varnishes, sealants, oral and teeth "dissolving strips", or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Dissolving strips are generally comprised of pullulan and may be impregnated with an effective amount of the NPC described herein. The dissolving strips dissolve over time within the oral cavity to apply the composition to surfaces within the oral cavity. The NPC therefore is released from the pullulan material and is thereby applied to relevant treatment sites.

Chewing gum can be any chewing gum composition, such as conventional compositions known in the art. In general, such compositions include a chewing gum base, to which may be added flavorants, sweeteners, colorants, and other ingredients known in the art. The chewing gum base is typically a natural or synthetic elastomer, such as rubber, chicle, lechi caspi, jelutong, polyisobutylene, an isobutylene-isoprene copolymer, a styrene-butadiene copolymer, or other suitable gum base known in the art. In certain embodiments, the NPC described herein is incorporated within suitable chewing gum compositions, such that the NPC is released to the oral cavity upon the chewing of the gum by the subject.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Vaginal Administration

A pharmaceutical composition of the invention may be prepared, packaged, or sold in a formulation suitable for vaginal administration. With respect to the vaginal or perivaginal administration of the compounds of the invention, dosage forms may include vaginal suppositories, creams, ointments, liquid formulations, pessaries, tampons, gels, pastes, foams or sprays. The suppository, solution, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

Buccal Administration

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Methods of Treatment

The present invention provides a method of treating and/or preventing biofilms and biofilm related infections comprising administering an effective amount of a composition comprising an NPC comprising at least one therapeutic agent. As described herein, the NPC described herein binds to sites within biofilms and to regions at risk for biofilm formation and accumulation. As such, the NPC described herein acts as a homing composition to provide sustained and local delivery of the therapeutic agent at target sites when the agent is needed. In certain embodiments, the NPC described herein is pH-responsive, where release of the therapeutic agent is influenced by the local pH. For example, in certain conditions, the development of acidic niches within biofilms are essential in causing oral diseases (such as dental caries) because: 1) the niches favor the growth of caries-causing and acid-producing organisms, 2) the niches induce further biofilm accumulation, and 3) the local acidity causes acid-dissolution of the tooth. Thus, in certain embodiments, the NPC of the invention comprises pH-responsive elements that induce the disassembly of the NPC micelle specifically in acidic conditions. This allows for delivery of the agent specifically in low pH conditions, when the agent is needed, while providing no or minimal delivery at physiological pH.

The method of the invention can be used to treat and/or prevent any type of biofilm or biofilm related infection. For example, it is demonstrated herein that administration of the composition of the invention inhibits the formation of biofilms, inhibits further accumulation of biofilm, promotes the disruption or disassembly of existing biofilms, and weakens an existing biofilm thereby allowing for easier mechanical biofilm disruption.

Exemplary conditions in which biofilms are implicated, and thus the conditions in which present method may be used to treat and/or prevent, include oral diseases including, but not limited to dental plaques, dental caries, gingivitis, periodontal diseases, as well as biofilm-associated mucosal infections, including for example, denture stomatitis and oral candidiasis. In certain embodiments, the present method may be used to treat and/or prevent exemplary diseases or disorders including, but not limited to, urinary tract infections, catheter infections, middle-ear infections, wounds, and infections of implanted biomaterials (e.g. artificial joints, artificial valves, etc).

In a specific embodiment, the method of the invention treats and/or prevents dental caries. Dental caries are generated by cariogenic biofilms formed on the pellicle. As described elsewhere herein, the NPC described herein binds to the pellicle as well as biofilms formed on the pellicle. Traditional methods of treating dental caries, based upon topical treatments, are defective in that active agents are not retained in the mouth for sufficient duration to exert its full therapeutic potential because of rapid clearance by saliva and ingestion.

The NPC described herein remains at the pellicle, or biofilm, thereby allowing for sustained and controlled delivery that prevents biofilm formation on "at-risk" surfaces and prevents further biofilm accumulation. Further, local delivery allows for the use of broad-spectrum active agents that would be inappropriate for use in traditional methods. Exposure of the entire oral cavity to broad-spectrum agents, which would occur with traditional delivery methods, would eliminate bacterial and microbial species indiscriminately, including those that are either harmless or beneficial to the health of the oral cavity. However, encased therapeutic agents and controlled and local delivery allows for use of these powerful agents without the risk of exposing the entire cavity to its effects.

The present invention is not limited to treating and/or preventing biofilms in a living body, but rather encompasses methods of treating and/or preventing biofilms on surfaces outside the body. For example, biofilms can form on surfaces in damp environments including bathrooms, kitchens, and certain industrial settings. In certain embodiments, the composition described herein is used in a method to treat and/or prevent biofilm formation or accumulation along surfaces in residential, commercial, and industrial settings. The method comprises administering an effective amount of an NPC comprising an anti-biofilm agent to the surface. In certain embodiments, the composition described herein is used in a method to treat and/or prevent biofilm formation on plants, trees, fruits, vegetables, and crops. The method comprises administering an effective amount of an NPC comprising an anti-biofilm agent a plant, tree, fruit, vegetable, or crop having a biofilm or at risk for formation a biofilm.

In certain embodiments, the method of the invention comprises administering an effective amount of a composition comprising an NPC and an encased therapeutic agent to a surface comprising a biofilm, and mechanically removing the biofilm. For example, it is described herein that the composition of the invention can weaken the biofilm structure or scaffold, which then allows for easier mechanical removal of the biofilm. For example, in certain embodiments, the method comprises administering the composition of the invention to a pellicle comprising a biofilm, and mechanically removing the biofilm, using for example a toothbrush or other tool.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician, dentist, or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound or conjugate of the invention, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

In one embodiment, the composition is administered by the subject to sites within their body. In another embodiment, the composition is administered by a health care professional (e.g. physician, dentist, dental hygienist, veterinarian, etc). For example, in one embodiment, dentists apply the NPC described herein directly on the teeth of a subject. In one embodiment, dentists apply the NPC described herein on sites at risk for biofilm formation and accumulation. In another embodiment, dentists apply the NPC described herein on sites where biofilm has already actively developed.

Controlled Release Formulations and Drug Delivery Systems

The present invention encompasses a composition and system for the controlled release of a therapeutic agent, when the therapeutic agent is triggered for release. For example, as described elsewhere herein, the NPC of the invention releases at least one therapeutic agent when and where the at least one therapeutic agent is needed. The triggering of release may be accomplished by a variety of factors within the microenvironment of the treatment or prevention site, including, but not limited to, temperature, pH, the presence or activity of a specific molecule or biomolecule, and the like.

In certain instances, controlled- or sustained-release formulations of a pharmaceutical composition of the invention may be made using conventional technology, using for example proteins equipped with pH sensitive domains or protease-cleavable fragments. In some cases, the dosage forms to be used can be provided as slow or controlled-release of one or more active ingredients therein using, for example, hydropropylmethyl cellulose, other polymer matrices, gels, permeable membranes, osmotic systems, multi-layer coatings, micro-particles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, lozenges, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In certain embodiments, the controlled-release formulation of the NPC described herein allows for release of a therapeutic agent precisely when the agent is most needed. In another embodiment, the controlled-release formulation of the NPC described herein allows for release of a therapeutic agent precisely in conditions in which the therapeutic agent is most active. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Controlled Release of Anti-Biofilm Agents Via pH-Activated Nanoparticle-Carriers Nanomaterials and nanoscale systems that actively respond to environmental stimuli can be employed as innovative delivery systems for drugs. Described herein is an exciting approach to retain and locally deliver antibiofilm agents. This approach uses versatile nanoparticle carriers (NPC) that binds to both the pellicle (at-risk site for biofilm formation) and EPS-rich matrix (within biofilm). This non-cytotoxic and non-bactericidal polymer-based nanocarrier also contains pH-responsive elements that facilitate the controlled release of therapeutic agents within acidic environments. Two proven antibiofilm agents (farnesol and apigenin) can be chemically linked to and released from NPC at low-pH values. Farnesol is a membrane-targeting antibacterial agent that is effective at acidic pH, while apigenin is an inhibitor of EPS synthesis. However, neither drug is optimally retained in the mouth. It is described herein that pH-activated nanoparticles enhance localization and provided controlled and sustained release of distinctive anti-biofilm agents in situ, where active biofilm assembly occurs, thereby enhancing drug efficacy against the onset of dental caries in vivo. Experiments described herein compared the effectiveness of the present drug-delivery approach (versus agents delivered without NPC) for biofilm control using an established mixed-species cariogenic biofilm model with a clinically relevant brief-exposure treatment regimen, Further, experiments are designed to examine whether NPC-delivered agents are more effective (versus agents delivered without NPC) in hindering dental caries disease onset in vivo. The present NPC-based drug delivery method is compared to current "gold standards" of caries prevention (fluoride) and antimicrobial therapy (chlorhexidine). The data presented herein demonstrates the potential for NPC to deliver therapeutic agents to specific local environments. This data demonstrates the ability to use NPC-based therapies to control oral biofilms, while also having relevance beyond the mouth, as biofilms are associated with most infectious diseases.

The materials and methods used in the experiments are now described.

Materials and Methods

The effectiveness of the NPC drug-delivery approach is evaluated versus agents delivered without NPC using both an in vitro mixed-species cariogenic biofilm and a rodent model of dental caries. A combination of effectiveness with protracted bioactivity (after brief topical exposure) in the presence of saliva is required to increase the likelihood of efficacy in vivo. Thus, a clinically relevant treatment regimen, based on daily topical applications of agents linked to NPC is used.

In Vitro

It is examined whether NPC-delivered agents (1) can disrupt initial biofilm assembly, (2) prevent further accumulation of biofilms, and (3) promote disassembly or prevent further buildup of pre-formed biofilms in the presence of saliva.

Preparation of Treatments

NPC-linked agents and free agents (not linked to NPC) are used for the following treatment/experimental groups: 1) NPC-apigenin, 2) NPC-farnesol, 3) NPC-apigenin+farnesol, 4) NPC only (NPC-control), 5) apigenin, 6) farnesol, 7) apigenin+farnesol, and 8) vehicle control. These agents are applied twice daily for 1 minute as conducted previously (Koo et al, 2005, J Dent Res, 84(11): 1016-1020; Falsetta et al., 2012, Antimicrob Agents Chemother, 56(12): 6201-6211). For optimization of drug-delivery, NPC linkers are systematically varied to enable tuning of the drug release rate, concentration, and longevity of drug release to provide the maximum therapeutic effect. The amount of drug incorporation and the length/chemistry of the degradable tether are changed to enhance apigenin and farnesol delivery/effectiveness.

Biofilm Formation

Figure 6:
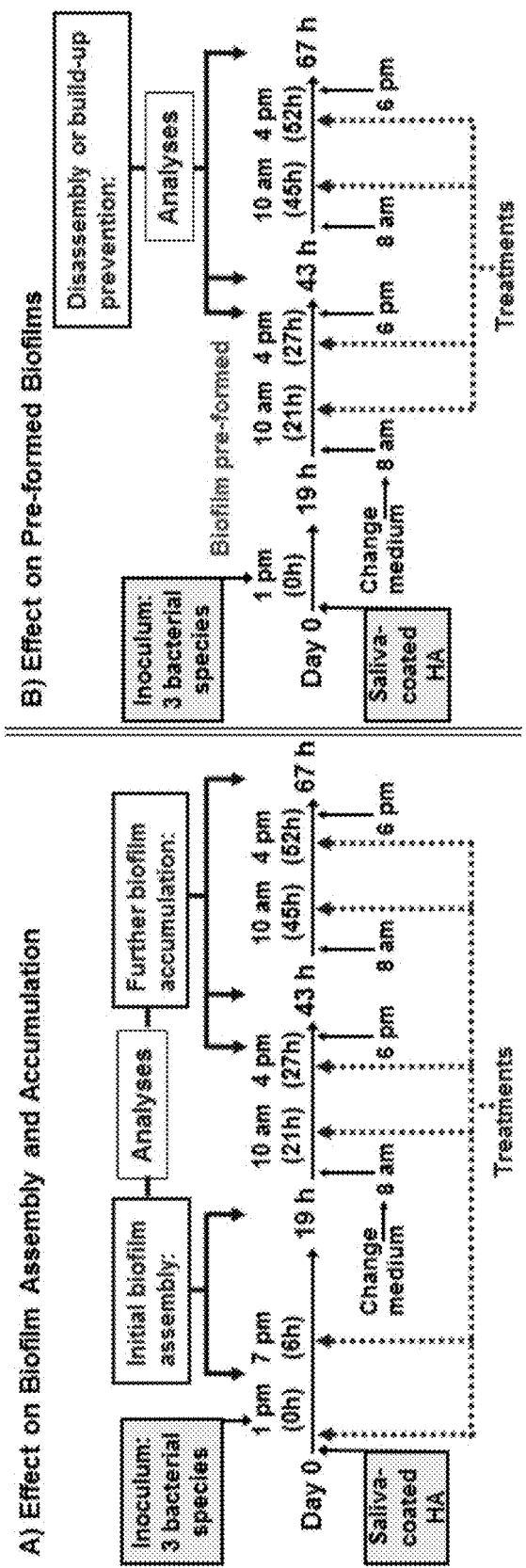
FIG. 6, comprising

Mixed-species biofilms on sHA discs are generated using an established in vitro model that mimics the dynamics of the ecological and biochemical changes associated with cariogenic biofilm development (Klein et al., 2012, PLoS One, 7(9): e45795, Xiao et al, 2012, PLoS Patholg, 8(4): e1002623). *S. mutans* UA159 (a proven cariogenic pathogen), *Actinomyces naeslundii* ATCC 12104 and *Streptococcus oralis* ATCC 35037 (early colonizers) are used. FIG. 6 depicts the experimental design, including time points for biofilm removal representing different stages of biofilm development (Xiao et al, 2012, PLoS Patholg, 8(4): e1002623). The following biofilm attributes are examined: 1) biomass, 2) structural organization, and 3) gene expression.

Biomass and 3D Biolfim Structure

The biomass and 3D spatial organization of the biofilms are analyzed using a combination of confocal fluorescence imaging and biochemical methods as detailed previously (Koo et al, 2005, J Dent Res, 84(11): 1016-1020; Xiao et al, 2012, PLoS Patholg, 8(4): e1002623). Briefly, EPS is labeled with Alexa Fluor 647 while the bacterial cells are labeled with Syto9 (Xiao et al, 2012, PLoS Patholg, 8(4): e1002623). The images are acquired using an Olympus FV1000 two-photon microscope with custom lasers and objectives, and analyzed with AMIRA (for 3D reconstruction), and COMSTAT-DUOSTAT (quantification of biofilm biomass, EPS and ratios). Standard biochemical and culturing methods are used to determine the dry-weight, protein/EPS content, and viable cells (colony forming units: CFU/dry-weight or CFU/protein) (Koo et al, 2005, J Dent Res, 84(11): 1016-1020).

Gene Expression

RT-qPCR is performed to monitor the expression of *S. mutans* genes gtfBCD (EPS synthesis) and atpD (acid-tolerance) genes, known to be directly affected by apigenin and farnesol (Falsetta, 2012, Antimicrob Agents Chemother, 56(12): 6201-6211). RNA is extracted from each of the treated biofilms and purified using protocols optimized for biofilms (Klein et al., 2012, PLoS One, 7(9): e45795, Xiao et al, 2012, PLoS Patholg, 8(4): e1002623). cDNA is synthesized and amplified using gene-specific primers following standardized procedures (Klein et al., 2012, PLoS One, 7(9): e45795, Xiao et al, 2012, PLoS Patholg, 8(4): e1002623). Northern Blot and RNAseq assays are also used to complement gene expression assays.

In Vivo

Animal Studies

Effective NPC-delivered agents, are evaluated using a rodent model of dental carries. Briefly, female Sprague-Dawley SPF rats are infected by mouth with *S. mutans*

UA159 (Koo et al., 2005, J Dent Res, 84(11): 1016-1020). The rats are randomly placed into experimental groups. Groups include the most-effective NPC-delivered agents and NPC-control. In addition, a clinically-proven anti-caries (fluoride; 250 ppm as NaF) and a broad-spectrum bactericidal (chlorhexidine; 0.12% v/v) agent are included as positive controls (and their vehicle control). Cariogenic plaque-biofilm formation are induced by feeding the animals Diet 2000 (contains 56% sucrose) and providing 5% (w/v) sucrose water to drink ad libitum for 5 weeks. Topical treatments are applied twice daily (including weekends) using camel brush. After the experimental period, the animals are killed by $CO_2$ asphyxiation.

Biochemical Assessment of Plaque

The jaws are aseptically dissected, and the plaque is removed and analyzed for (1) S. mutans and total cultivable flora counts using culturing (MSB agar and blood agar) and PCR-based methods, and (2) EPS content.

Caries Assessment

The teeth are subjected to dental caries scoring according to Larson's modification of Keyes' system.

Statistical Analyses

The in vitro data (from imaging, biochemical, and gene expression analysis) and the in vivo data (caries scores and microbial counts) are analyzed using JMP version 8.0 (SAS Institute Inc.) with the level of significance set at 0.05.

The results of the experiments are now described.

NPC Bind to the Pellicle and EPS-Matrix in the Presence of Saliva.

Figure 2:
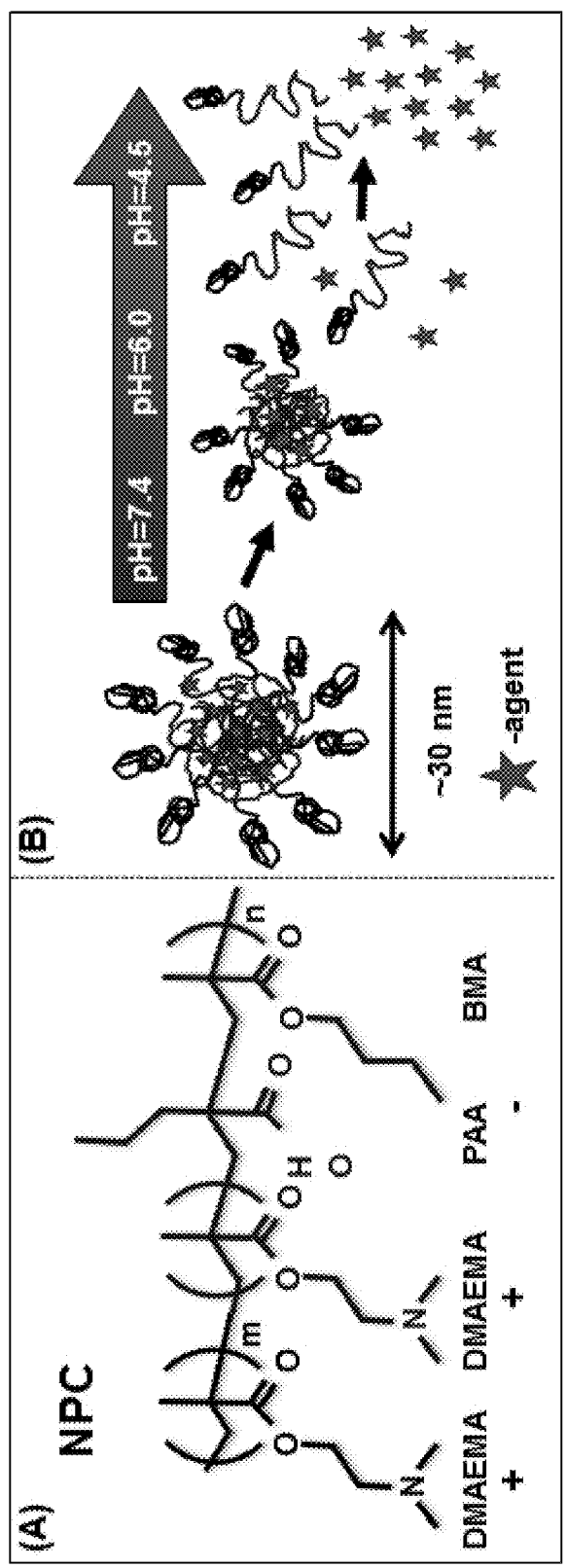
FIG. 2, comprising

Nanoparticle-carriers (NPC) are selected based on their chemical composition and functionality. They are comprised of polymer-based cationic micelles that electrostatically interact with specific surfaces and include pH-responsive elements. The NPC are highly effective in delivering a variety of drugs at acidic pH (Benoit et al, 2010, Mol Pharm, 7(2): 442-455), are not toxic to human cells and are non-bactericidal. FIG. 2 shows the overall structure of the NPC (including the pH-responsive and drug-delivery elements), as well as the overarching principles of pH-triggered NPC drug release. The NPC comprises poly(dimethylaminoethyl methacrylate)-b-poly(dimethylaminoethyl methacrylate-co-propylacrylic acid-co-butyl methacrylate) (pDMAEMA-b-p (DMAEMA-co-PAA-co-BMA)) (FIG. 2A). FIG. 2B depicts the pH-dependent structure of NPC. The outer element (in black) is protonated at physiological pH, and was designed to have high avidity to the pellicle. The inner element (in blue) was designed to be nearly charge neutral at physiological pH but hydrophobic with inclusion of BMA. The inner element becomes more protonated at lower pH environments, disassembling the NPC and releasing the drug(s) from nanoparticle cores.

It was initially tested whether selected NPC bind to pellicle-coated hydroxyapatite (HA) bead surfaces in the presence of saliva. The NPC was mixed with saliva prior to incubation with pellicle-coated HA beads. After NPC exposure (1 to 60 min), the beads were thoroughly washed in phosphate buffer to remove any unbound material, and analyzed via confocal imaging.

Figure 3:
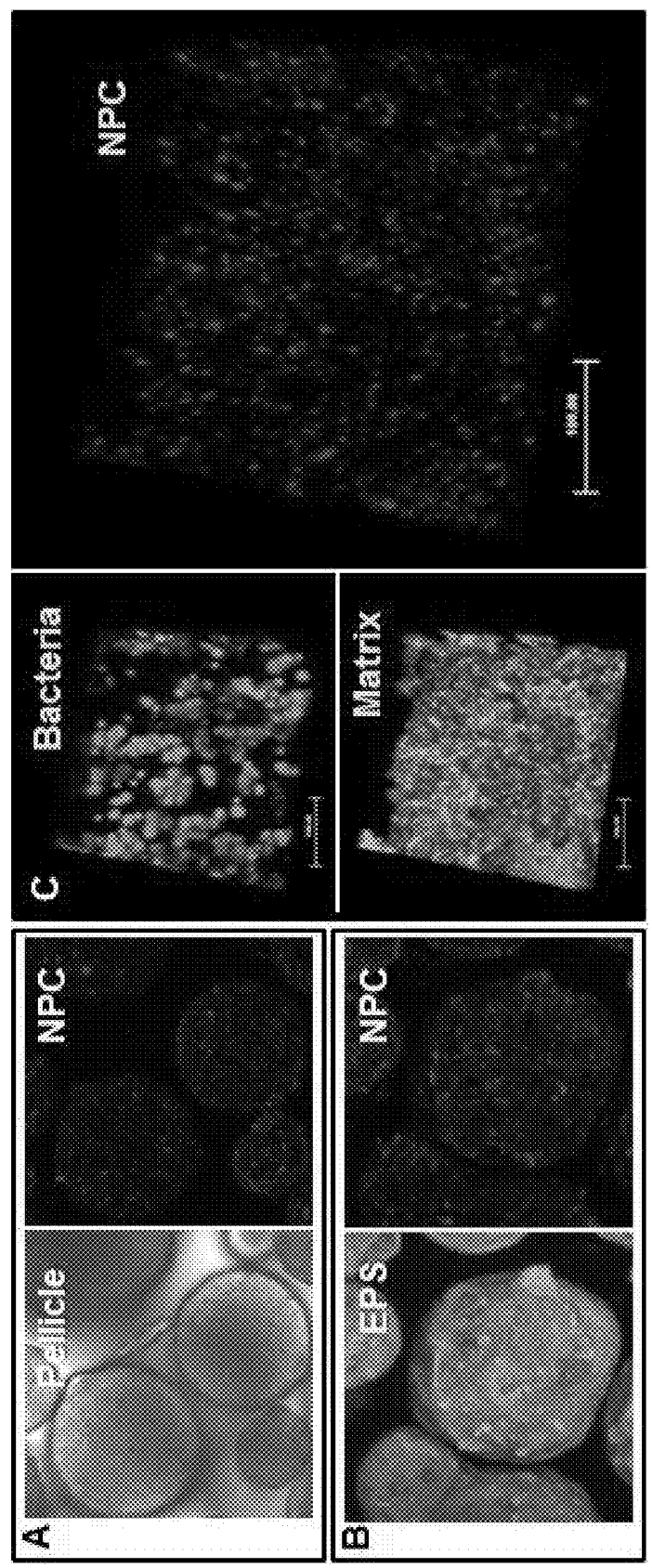
FIG. 3, comprising

The data show that the NPC bind avidly and uniformly to the pellicle, even in the presence of saliva (FIG. 3A). The binding appears to be tight as NPC remained bound even after vigorously washing the beads by vortexing the mixture The retention of NPC on pellicle is highly relevant because: 1) biofilms formed on pellicle-coated surfaces (at-risk sites), and 2) most of the currently available therapeutic agents are not retentive in the mouth after topical, brief application. Next, it was tested whether the NPC bind to EPS formed on the pellicle-coated HA surface and/or to the EPS-rich biofilm matrix. S. mutans GtfB immobilized on the pellicle-coated HA was incubated with sucrose to form EPS in situ. Then, it was examined whether NPC would bind to EPS (labeled in blue) formed on the pellicle-coated HA in the presence of saliva (as described above). The NPC did effectively bind to surface-formed EPS, as clearly shown in FIG. 3B. This observation is also clinically important because EPS on surface acts as binding sites for pathogenic organisms, such as Streptococcus mutans (a proven cariogenic organism), promoting accumulation of harmful bacterial on the surface. The NPC without the binding motif (see structure in FIG. 2A) did not adhere to the pellicle or to EPS. Thus, the nanocarriers are devoid of non-specific binding.

Subsequently, the ability of NPC to bind to the biofilm matrix was evaluated. Biofilms were exposed to NPC during their development. Following NPC treatment, the biofilms were washed to remove any unbound material. 3D biofilm reconstruction shows that NPC (in red) are thoroughly distributed across the biofilm and are associated with the EPS-rich matrix (FIG. 3C). This shows that NPCs are retained within biofilms. Furthermore, NPC are devoid of any antibacterial activity against S. mutans.

Antibiofilm Agents can be Chemically Linked and Released from NPC Over Time and as a Function of Decreasing pH.

NPC have been synthesized that are inclusive of drug-releasable tethers as performed previously (Benoit et al, 2006, Biomaterials, 27(36): 6102-6110). The released drugs do not have any difference in structure or activity compared to their unaltered counterparts. These copolymers include farnesol-, apigenin-, or both farnesol- and apigenin-releasable tethers.

Figure 4:
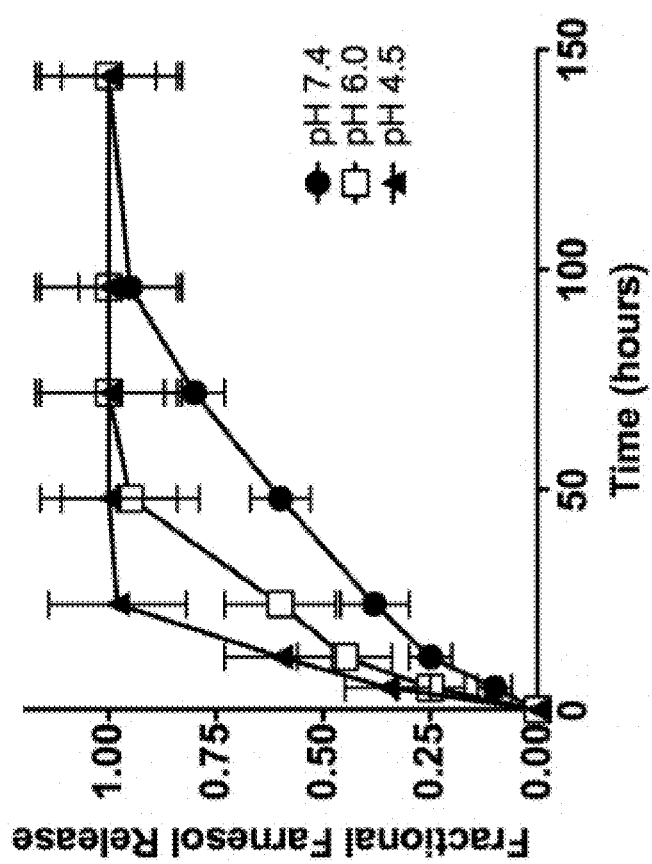
FIG. 4 is a graph depicting the results of experiments demonstrating the controlled release of farnesol from NPC over time and as a function of pH. Fractional release is shown for one degradable tether length with 6 degradable bonds, error bars are standard deviation (n=5).

As shown in FIG. 4, there was a sustained delivery of farnesol from polymers up to 6 days for one degradable tether length; the overall dose is controlled by the tethered drug concentration, whereas the release rate is controlled by the environmental pH (lower pH results in more rapid release) and the chemistry and length of the degradable tethers (Benoit et al, 2006, Biomaterials, 27(36): 6102-6110). The initial experimental condition delivered a 10-20× molar concentration of farnesol (up to 100 µM; which is well above the minimum inhibitory concentration) from the NPC compared to the dose of the NPC alone, owing to multivalent tethering. The drug-delivery system can further be optimized for maximum release of farnesol and apigenin over time at the low pH values (pH 4-5) usually attained at the surface of attachment and within cariogenic biofilms. At the same time, it can be tweaked so the agents are minimally released at physiological neutral pH.

Figure 5:
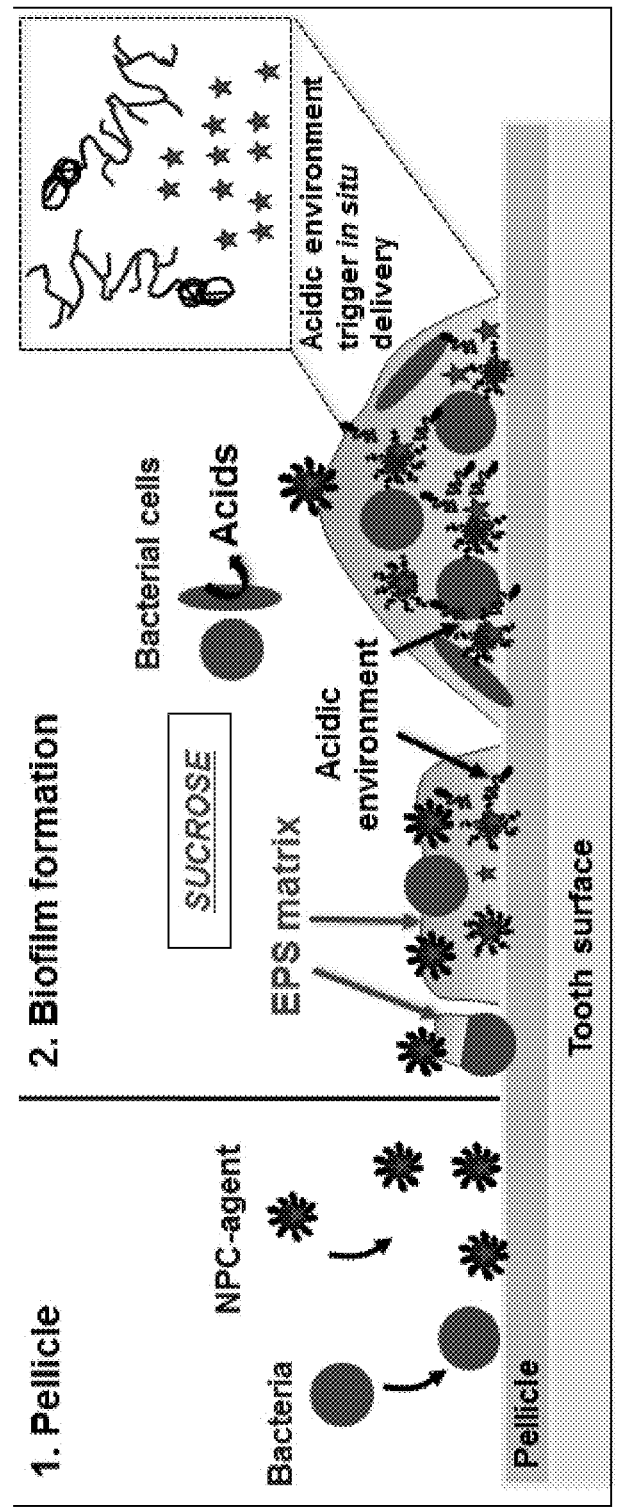
FIG. 5 is an illustration depicting a proposed model for sustained and controlled in situ drug-release via NPC.

Collectively, the data presented herein show a highly innovative and feasible technology that could be an ideal antibiofilm agent carrier (see FIG. 5). It incorporates a "homing device" that facilitates sustained and controlled drug-release when the local pH becomes acidic (precisely when the agents can be most effective). In comparison to agents not linked to NPC, NPC-delivered drugs are more effective in disrupting biofilm assembly and the accumulation. Without wishing to be bound by any particular theory, NPC-delivered drugs may possibly elicit disassembly. Further, NPC-delivery may enhance the repression of S. mutans virulence genes within mixed-species biofilms.

In Vivo Model of Dental Caries

NPC-delivered agents are more effective in disrupting cariogenic biofilm formation and the onset of cavitation in vivo (vs. agents delivered without NPC). Furthermore, NPC-delivered agents are comparable (or possibly superior) to fluoride and chlorhexidine in reducing bacterial colonization (biofilm formation) and the incidence and severity of carious lesions. The data supports the effectiveness and usefulness of pH-activated NPC for the local delivery of therapeutic agents in a clinical setting.

The data presented herein provides the foundation for the development of this technology. In other embodiments, fluoride is incorporated in the delivery system, allowing simultaneous release of antibiofilm and anticaries agents in situ. In addition, in other embodiments, other drugs are linked to NPC, such as anti-inflammatory and anesthetics, for local delivery within acidic environments commonly found in sites undergoing an active inflammation process (e.g. periodontitis). Clearly, the present technology can be used to prevent/treat other human diseases or even industry issues caused by biofilms. The low-cost and flexibility of NPC chemistry allows the development of a variety of products to provide benefits to consumers. It is anticipated that the NPC-linked agents could be included in products for daily oral health maintenance (e.g. mouthrinse/tooth paste) or in-office treatment (e.g. gels for topical application, varnish or restorative materials).

Example 2 pH-Activated Nanoparticle for Targeted, Controlled Release of Anti-Biofilm Agents in Dental Applications The experiments presented herein were conducted to explore the activity of diblock copolymers comprising poly (2-dimethylamino)ethyl methacrylate, butyl methacrylate (BMA), and 2-propylacrylic acid (PAA) (pDMAEMA-b-p (DMAEMA-co-BMA-co-PAA)) and the ability of such polymers to target the dental surface and entrap and deliver the anti-biofilm drug, farnesol. Cationic NPCs as well as several control polymers and micelles were synthesized and analyzed for their ability to target dental surfaces through electrostatic interactions. These NPCs were also analyzed for their ability to load farnesol and to respond to low pH consistent with biofilm microenvironments to enhance carrier binding and trigger farnesol release through micelle core disruption. Finally, the antibacterial and antibiofilm efficacy of NPC-mediated delivery of farnesol was examined.

It is shown herein that diblocks self-assemble into ~21 nm positively-charged nanoparticles and exhibit adsorption affinities to mimetic dental surfaces of ~215 L*mmol$^{-1}$ due to electrostatic interactions of the cationic nanoparticle coronas, which exhibit ~15.9 mV zeta potentials, with negatively charged dental surfaces. Moreover, due to their hydrophobic cores, these NPCs load farnesol at up to ~27 wt %. Farnesol is released in a pH-dependent manner with $t_{1/2}$=7.3 and 14.7 h for release at pH 4.5 and 7.2, respectively, as the nanoparticles exhibit pH-responsive behaviors that result in core destabilization at acidic pH microenvironments that mimic dental biofilms. Finally, nanoparticle antibacterial and antibiofilm activities were assessed. *S. mutants* viability decreased by 3 logs after treatment with farnesol loaded nanoparticles. Additionally, a 50% decrease in *S. mutants* biofilm colony forming units was observed after a clinically-relevant nanoparticle treatment regimen was utilized. Thus, NPCs have great potential to deliver antibiofilm drugs by increasing drug efficacy through targeted and localized drug delivery and rapid, triggered release due to low pH consistent with dental biofilm micro environments.

The materials and methods used in these experiments are now described.

Materials

Chemicals and materials were supplied by Sigma-Aldrich unless otherwise specified. Ethylsulfanylthiocarbonyl sulfanylvpentanoic acid (ECT) and propylacrylic acid (PAA) were synthesized as described previously (Benoit et al., 2011, Biomacromolecules, 12(7):2708-14; Murthy et al., 1999, J Control Release, 61(1):137-43). 2,2-azobisisobutyronitrile (AIBN) was recrystallized from methanol. Dimethylaminoethyl methacrylate (DMAEMA) and butyl methacrylate (BMA) were distilled prior to use, and poly (ethylene glycol) monomethylether methacrylate was filtered over basic alumina to remove inhibitor.

Polymer Synthesis

Polymers were synthesized by reversible-addition fragmentation chain transfer (RAFT) polymerizations that provide precise control over polymer molecular weights and polydispersity indices ($M_w/M_n$, PDI<1.3). Specifically the following polymers were synthesized: p(DMAEMA)-b-p (DMAEMA-co-BMA-co-PAA), p(DMAEMA), p(DMAEMA)-p(BMA), and p(PEGMA)-b-p(DMAEMA-co-BMA-co-PAA). RAFT polymerizations were performed in the presence of monomers, 2,2-azobisisobutyronitrile (AIBN) as the initiator, and ECT as chain transfer agent (CTA). The specific reaction conditions for each polymer are detailed below.

Synthesis of Poly(Dimethylaminoethyl Methacrylate), p(DMAEMA)

Three grams (3 g) of dimethylformamide (DMF) (40 wt % monomer) and 2 g of distilled DMAEMA was introduced into reaction vessels. The initial monomer to CTA ratio ($[M]_0:[CTA]_0$) was such that the $M_n$ was 16.0 kDa for p(DMAEMA) that was used as a control, 9.1 kDa for p(DMAEMA) that was used as macroCTA for synthesis of block copolymers with p(DMAEMA-co-BMA-co-PAA), and 22.8 kDa for synthesis of block copolymers with p(BMA) (FIG. 7C). CTA to initiator ratios ($[CTA]_0:[I]_0$) were 10:1. Reactions were purged with nitrogen using for 40 min using a Schlenk line prior to transfer to an oil bath at 60° C. for polymerization (t=6 h). The resulting polymers (p(DMAEMA)) were isolated by precipitation in 30:70 diethyl ether:pentane and centrifugation. p(DMAEMA) polymers was redissolved in acetone and precipitated in pentane three times and dried overnight in vacuo.

Synthesis of Poly(Poly(Ethylene Glycol) Monomethylether Methacrylate), p(PEGMA), macroCTA Two grams (2 g) of dehibited poly(ethylene glycol) monomethylether methacrylate (360 g/mole) was combined with 3 g DMF and CTA, at initial monomer to CTA ratio ($[M]_0: [CTA]_0$) of 150. The solution was purged with nitrogen for 40 minutes and reacted for 6 hours at 60° C. CTA to initiator ratios ($[CTA]_0:[I]_0$) were 10:1. The resulting p(PEGMA) macroCTA was isolated by precipitation in 30:70 diethyl ether/pentane and centrifugation. p(PEGMA) polymers were redissolved in acetone and subsequently precipitated in pentane three times and dried overnight in vacuo.

Synthesis of p(DMAEMA)-b-p(DMAEMA-Co-BMA-Co-PAA) Block Copolymers

Diblock copolymers of p(DMAEMA)-b-p(DMAEMA-co-BMA-co-PAA) were synthesized using 9.1 kDa p(DMAEMA) macroCTA. The desired stoichiometric quantities of DMAEMA, PAA, and BMA (25:25:50%, respectively) were added to the p(DMAEMA) macroCTA dissolved in DMF (25 wt % monomers, $[M]_0:[CTA]_0$=250:1). CTA to initiator ratios ($[CTA]_0:[I]_0$) were 10:1 with AIBN as the initiator. Following the addition of AIBN, the solutions were purged with nitrogen for 40 minutes and allowed to react at 60° C. for 24 hr. The resulting diblock copolymers were isolated by precipitation in 30:70 diethyl ether/pentane and centrifugation. The polymers were then redissolved in acetone and precipitated in pentane three times and dried overnight in vacuo.

Synthesis of p(PEGMA)-b-p(DMAEMA-Co-BMA-Co-PAA) Block Copolymers

Diblock copolymers of p(PEGMA)-b-p(DMAEMA-co-BMA-co-PAA) were synthesized using 18.7 kDa p(PEGMA) macroCTA. The desired stoichiometric quantities of DMAEMA, PAA, and BMA (25:25:50%, respectively) were added to the p(PEGMA) macroCTA dissolved in DMF (25 wt % monomers) ([M]$_0$:[CTA]$_0$, 250:1). CTA to initiator ratios ([CTA]$_0$:[I]$_0$) were 10:1 with AIBN as the initiator. Following the addition of AIBN, the solutions were purged with nitrogen for 40 minutes and allowed to react at 60° C. for 24 hr. The resulting diblock copolymers were isolated by precipitation in 30:70 diethyl ether/pentane and centrifugation. The polymers were then redissolved in acetone and precipitated in pentane three times and dried overnight in vacuo.

Synthesis of p(DMAEMA)-b-p(BMA) Block Copolymers

Diblock copolymers of p(DMAEMA)-b-p(BMA) were synthesized using 22.8 kDa p(DMAEMA) macroCTA. The desired stoichiometric quantities of BMA were added to the p(DMAEMA) macroCTA dissolved in DMF (25 wt % monomers) ([M]$_0$:[CTA]$_0$, 250:1). CTA to initiator ratios ([CTA]$_0$:[I]$_0$) were 10:1 with AIBN as the initiator. Following the addition of AIBN, the solutions were purged with nitrogen for 40 minutes and allowed to react at 60° C. for 24 hr. The resulting diblock copolymers were isolated by precipitation in 30:70 diethyl ether/pentane and centrifugation. The polymers were then redissolved in acetone and precipitated in pentane three times and dried overnight in vacuo.

Polymer Labeling

All polymers were labeled with Texas Red® Sulfonyl Chloride (Thermo Scientific, US) through incubation of 0.25 wt % polymer with $2*10^{-4}$ wt % Texas Red® in triethylamine (TEA) and dimethylformamide (DMF) solution (1% v/v). Labeled polymers were purified using dialysis against distilled, deionized water (ddH$_2$O) using 3500 kDa MWCO membranes (Spectra/Por®, Spectrum Labs, Rancho Dominguez, Calif.). Dialysis water was changed twice a day for 5 days and polymers were collected via lyophilization.

Characterization of Polymers

Molecular Weight Determination and Confirmation of Polymer Compositions

Absolute molecular weights and polydispersities (Mw/Mn, PDI) of all polymers were determined by gel permeation chromatography (GPC, 1200 Series (Shimadzu Technologies, Santa Clara, Calif.) equipped with a miniDAWN TREOS, multi-angle light scattering (MALS) instrument (Wyatt Technologies, Santa Barbara, Calif.) and a refractive index detector (Shimadzu Technologies, Santa Clara, Calif.); columns: guard, TSK Gel Super H-H; gel separation, TSK Gel HM-N, Tosoh Bioscience, Montgomeryville, Pa.)). HPLC-grade DMF containing 0.05 M LiBr at 60° C. was used as the mobile phase at a flow rate of 0.35 mL/min. Absolute molecular weights were determined using reported dn/dc values for p(DMAEMA) (0.06 ml/g) (Gallow et al., 2012, Polymer (Guildf), 53(5):1131-7; Kryuchkov et al., 2011, Macromolecules, 44(13):5209-17; Vesterinen et al., 2011, eXPRESS Polym Lett, 5(9):754-65) and PEG (0.13 ml/g) (Liu et al., 2012, Langmuir, 28(8):3831-9). Block copolymers that included pH-responsive blocks ((p(DMAEMA-co-BMA-co-PAA)) were analyzed via $^1$H NMR spectroscopy (Bruker Avance 400) to confirm second block composition, as previously described (Convertine et al., 2009, J Control Release, 133(3):221-9).

Formation and Characterization of NPC

Sized, polydispersity indeces (PDI) and zeta potentials of nanoparticles of p(DMAEMA)-b-p(DMAEMA-co-BMA-co-PAA), p(PEGMA)-b-p(DMAEMA-co-BMA-co-PAA), and p(DMAEMA)-b-p(BMA) were measured using Zetasizer (Malvern Instruments, UK). The measurements were performed at 0.2 mg/ml and 2.7 mg/ml for size measurements. Zeta potentials were measured at 0.2 mg/ml and pH 7.2, except for p(DMAEMA)-b-p(DMAEMA-co-BMA-co-PAA), which zeta potentials were measured at a range of pH (3.4-10.5), to correlate surface charges of particles to binding of dental surfaces.

Critical Micelle Concentrations (CMC) of NPC

Figure 11:
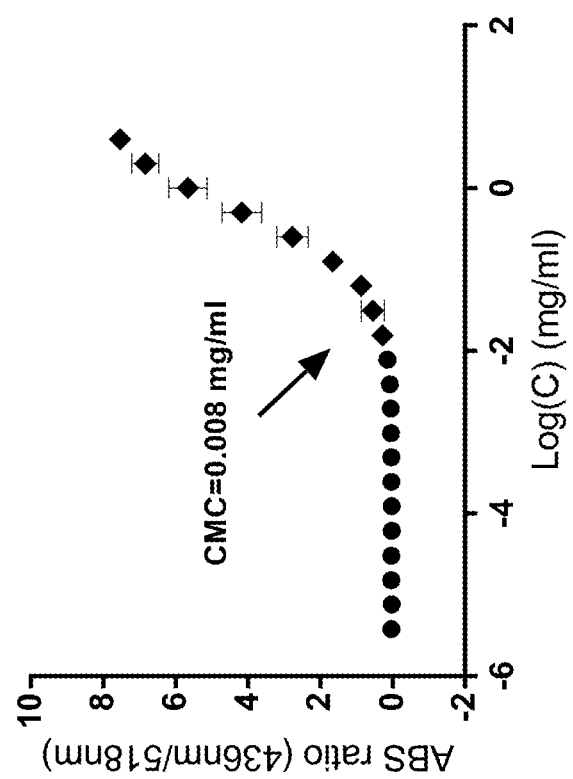
FIG. 11 depicts the results of experiments demonstrating the critical micelle concentration (CMC) of NPC. A range of NPC concentrations was incubated with PRODAN® and the ratio of fluorescent emissions in hydrophobic phase/hydrophilic phases was plotted versus log(micelle concentration). CMC was determined as a concentration at which the emission ratio begins to increase with polymer concentration. The error bars represent standard error of measurements (n=3).

CMC of micelle-based NPCs composed of p(DMAEMA)-b-p(DMAEMA-co-BMA-co-PAA) was approximated using solvatochromic shifts in fluorescence emission of PRODAN® (Molecular Probes, Eugene, Oreg.) (Adhikary et al., 2009, J Phys Chem B, 113(35):11999-2004; Rodriguez et al., 2010, J Biomed Opt, 13(1):014025). Briefly, PRODAN® dissolved in methanol was aliquoted into black 96-well plates. After drying overnight, micelle solutions at a range of concentrations (0-2 mg/ml) were added and incubated overnight to achieve final PRODAN® concentrations of $5.45*10^{-4}$ mg/ml. PRODAN® emission was measured at two wavelengths (Ex/Em$_1$: 360 nm/436 nm and Ex/Em$_2$: 360 nm/518 nm) that corresponds to emission of PRODAN® in hydrophobic and hydrophilic phases, respectively. The ratio of emissions (hydrophobic phase/hydrophilic phase, Em$_1$/Em$_2$) was plotted versus of log (micelle concentration), and CMC was determined as a concentration at which the emission ratio begins to increase with polymer concentration (FIG. 11).

Adsorption of Polymers onto Dental Mimetic Surfaces

Preparation of Mimetic Dental Surfaces

Figure 12:
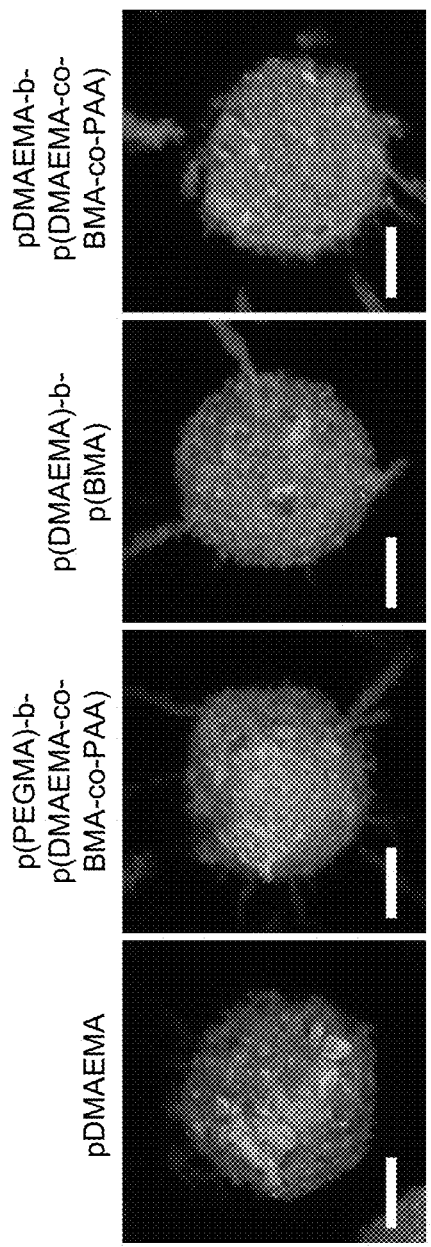
FIG. 12 depicts the results of experiments confirming the formation of gsHA. Confocal images of glucan assembly on sHA surfaces (scale bars, 20 μm) used for binding experiments. gsHA surfaces were formed by incubation of sHA beads with purified glucosyltransferase B (GtfB) enzyme and sucrose in presence of Alexa Fluor® 647 labeled dextran (Ex/Em: 647 nm/668 nm) as described elsewhere.

Three materials that emulate dental surfaces were used to assess the adsorption of polymers: uncoated hydroxyapatite (HA), hydroxyapatite coated with saliva (sHA), and hydroxyapatite coated with glucans (gsHA), which is a critical component of the matrix of cariogenic biofilms. Hydroxyapatite (CHT™, BioRad) beads were washed twice with buffer (50 mM KCl, 1 mM KPO$_4$, 1 mM CaCl$_2$, 1 mM MgCl$_2$, 0.1 mM PMSF and 0.02% NaN$_3$, in dd-H$_2$O, pH 6.5). Washed HA beads were incubated with human saliva to obtain saliva coated-hydroxyapatite (sHA). gsHA surfaces were produced by incubating sHA beads with purified Glucosyltransferase B (GtfB) enzyme and sucrose for glucan formation on the sHA surfaces in the presence of Alexa Fluor® 647 labeled dextran (Ex/Em: 647 nm/668 nm) (Life Technologies) as described elsewhere (Schilling et al., 1992, Infect Immun, 60(1):284-95). The formation of glucan layers was confirmed (FIG. 12) by confocal laser scanning microscopy (FV1000 Olympus, USA) (Klein et al., 2009, Appl Environ Microbiol, 75(3):837-41).

Assessment of Polymer Binding

Quantitative assessment of polymer adsorption to dental surfaces was performed in triplicate by incubation of 1 μM of Texas Red®-labeled polymers with dental surfaces for 1 hour at 37° C. The amount of adsorbed polymer was analyzed based on the difference in Texas Red® signal (Ex/Em: 550 nm/617 nm) before and after adsorption, as measured by an Infinite N200 PRO microplate reader (Tecan, Switzerland). Results were confirmed by confocal laser scanning microscopy imaging of HA, sHA, and gsHA surfaces that were incubated with 85 μM polymer solutions for 1 hour at 37° C. Confocal images were analyzed for surface area coverage by polymers using ImageJ software (v. 1.47). In brief, the images were transformed to 8 Bit and built-in thresholds ("Moments") were applied to standardize the images. 5 independent areas on each standardized image were selected for analysis. Binding of NPC and p(DMAEMA) to hydroxyapatite (HA) at a range of pH (3.4-10.5) was also quantified to examine how protonation of the p(DMAEMA) tertiary amine residues affect adsorption.

Adsorption Equilibrium Curves

Adsorption of NPC to HA, sHA, and gsHA was further analyzed at concentrations of 0-15 µM, and Langmuir equilibrium curves were fit to adsorption equilibrium data by GraphPad Prism software (v.6.03). From the fits, adsorption affinity constants ($K_a$[L*mmol$^{-1}$]) and maximal amounts of adsorbed NPC to the various mimetics of dental surfaces ($X_{max}$ [mmole/m$^2$]) were calculated. NPC adsorption was expressed relative to a surface area of hydroxyapatite beads which was calculated according to the average radius and density of the beads as provided by the manufacturer (80 nm and 0.63 g/ml, respectively).

Loading and Release of Antibiofilm Agent, Farnesol, from Polymer Micelles

Drug Loading

Figure 13:
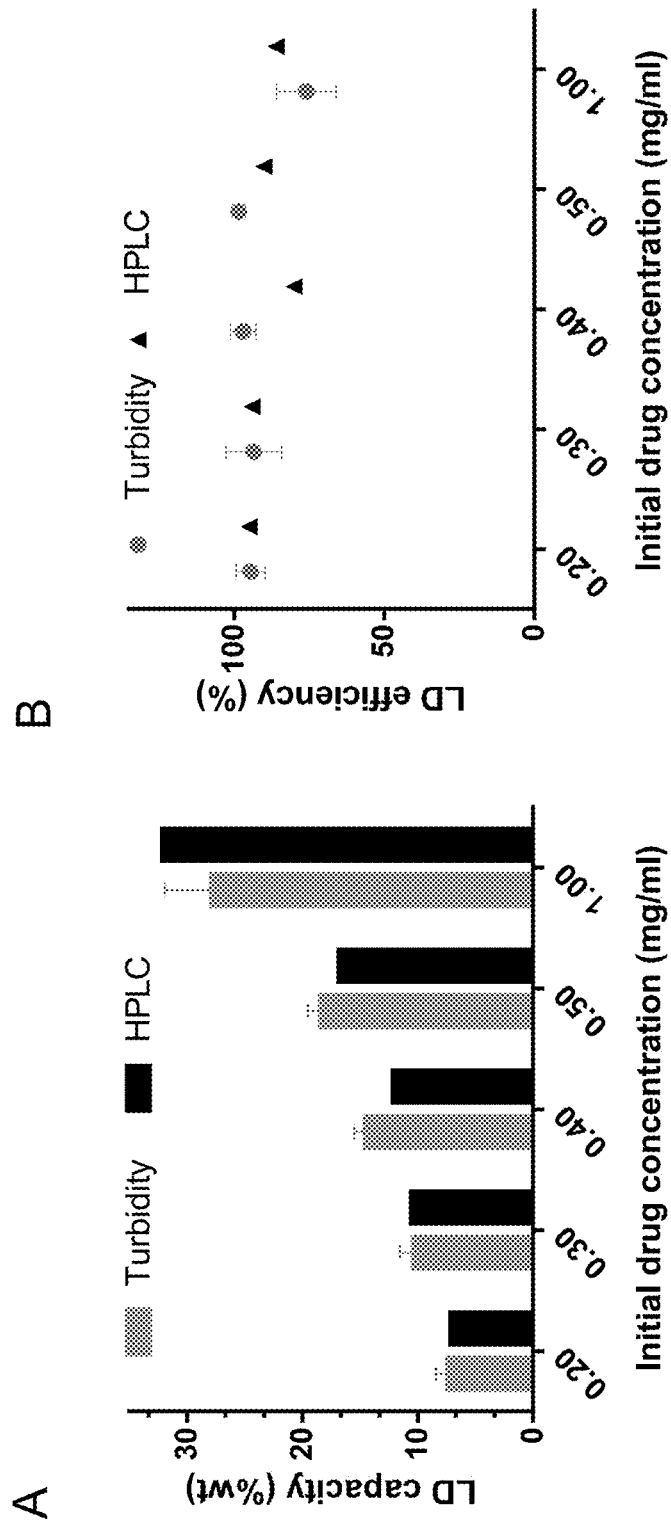
FIG. 13, comprising

Micelles were loaded with farnesol by sonication similar to Tang et al. (Tang et al., 2003, Biomacromolecules, 4(6): 1636-45). Briefly, farnesol emulsions at a range of concentrations (0.2-1.5 mg/ml) were prepared by sonication with an ultrasonic homogenizer (Sonic Raptor 250, Omni International, Kennesaw, Ga.) in ddH$_2$O at 40% power. Emulsions were then mixed with 2.7 mg/ml of p(DMAEMA)-b-p(DMAEMA-co-BMA-co-PAA) micelles in glass scintillation vials. These solutions were placed in a bath sonicator (50 HT, VWR) for 5 minutes. Based on calibration curves, the change in absorption of farnesol emulsions at 700 nm (as a measure of turbidity) was correlated to the amount of drug loaded. According to the amount of farnesol loaded, loading capacities $$\left(100 * \left(\frac{Wt_{loaded}}{Wt_{micelle}}\right)\right)$$

and efficiencies $$\left(100 * \left(\frac{Wt_{loaded}}{Wt_0}\right)\right)$$

were calculated. Where $Wt_{loaded}$ is the amount of loaded drug, $Wt_{micelle}$ is the amount of micelle, and $Wt_0$ is the initial amount of farnesol in emulsion. To confirm this method of calculating loading capacities and efficiencies high pressure liquid chromatography was used (HPLC). Briefly, NPC loaded with farnesol were concentrated with 3 kDa centrifugal filters units (Amicon Ultra® 0.5 ml, Millipore, USA), and washed two additional times by centrifugation with PBS. The amount of farnesol in retentate was measured to determine loading capacity using HPLC (Shimadzu Technologies, Santa Clara, Calif.) with a C18 column (Kromasil® Eternity, 4.6 mm×50 mm, Supelco, Bellefonte, Pa.), at flow rate of 0.5 ml/min, with a gradient of 10% to 90% of MeOH:H$_2$O over 20 minutes, and detection by UV absorbance (210 nm). HPLC analysis agreed with the simplified method for analysis of drug loading as the two data sets were found to be statistically equivalent (p<0.01), based on two-tailed Kolmogorov-Simonov test (FIG. 13).

Nanoparticle sizes both before and after farnesol loading were examined using transmission electron microscopy. Briefly, micelles were loaded with farnesol at loading capacities of 0 wt %, 18.4 wt %, and 27 wt %, transferred to carbon coated nickel grids, and dried for 2-5 minutes in the presence of 2% (w/v) phosphotungstic acid as a contrast agent. The images of free and loaded NPC were taken at magnifications of 200000× using a Hitachi 7650 transmission electron microscope (Hitachi, Schaumburg, Ill.), attached to 11 megapixel Erlangshen digital camera system (Gatan, Pleasanton, Calif.).

Drug Release

Farnesol release from loaded micelles was quantified using dialysis. Briefly, farnesol loading was performed at a priori identified optimized loading efficacy (17.5 wt %) in PBS. Drug-loaded micelles were placed in PBS at pH 4.5 or pH 7.2, and dialyzed at 37° C. through 6-8 kDa dialysis membranes (Spectra/Por®, Spectrum Labs, Rancho Dominguez, Calif.), with daily changes of medium. Farnesol was quantified at day: 0, 1, 2, 3, 4 and 7 by HPLC as previously detailed. At no time point was the concentration of free farnesol higher than its estimated solubility limit of 1.7 mg/L (US EPA; Estimation Program Interface (EPI) Suite V.3.12). Fits of the release data were performed assuming first order release kinetics using GraphPad Prism® Software (v.6.03). According the fits, release rate constants, $k_r$, and release half-times, $t_{1/2}$, were calculated according to the first order release equation (% Release=100*(1−e$^{-k_{obs}*t}$). Where % Release is the % of drug released at time t, and $k_{obs}$ is the observed kinetic constant of drug release which was be converted to release half-time according to the following relationship:

$$t_{1/2} = \frac{\ln(2)}{K_{obs}}.$$

Once the fit parameters were determined, first derivatives of the fit equations $$\left(\text{Release rate} = \frac{d(\% \text{ Released})}{dt} = 100 * k_{obs} * e^{-K_{obs}*t}\right)$$

were calculated to assess farnesol release rate over time.

Antimicrobial and Antibiofilm Activities and Nanoparticle Mediated Farnesol Release

*Streptococcus mutans* UA159 (ATCC 700610; serotype c, as a model cariogenic organism) was used to assess the effect of nanoparticle-mediated release of farnesol on cell viability and biofilm formation. *S. mutans* UA159 cells were grown to mid-exponential phase in ultrafiltered (10 kDa membranes) tryptone-yeast extract broth (UFTYE, pH 7.0) containing 1% (w/v) glucose (at 37° C.; 5% CO$_2$), and harvested by centrifugation (5,500×g, 10 min, 4° C.). The cells were then washed three times with 0.89% NaCl and collected via centrifugation (5,500×g, 10 min, 4° C.). Cell suspensions were sonicated using a Branson Sonifier 450 (four 10-second pulses with 5-second intervals at 20 W; Branson Ultrasonics Co., Conn., USA) to obtain single-celled suspensions as verified by light microscopy. The optical density (600 nm) of cell preparations were adjusted to 0.5±0.05 which corresponds to 1.5×10$^9$ *S. mutans* colony forming units/ml (CFU/ml).

Cell suspensions (1 ml each) were centrifuged, and the cell pellet was resuspended with 1 ml of treatment solution in 1×PBS, pH 7.0 [NPC-control (1.47 mg/ml NPC), NPC-farnesol (1.47 mg/ml NPC, loaded with 0.3 mg/ml farnesol), or PBS control (1×PBS, pH 7.0)]. The cells were incubated with treatments on a shaker for 1 h at 37° C. After incubation, 0.1 ml aliquots of each suspension were diluted 10-fold, and 0.1 ml was plated onto blood agar plates. The remaining 0.9 ml of each cell suspension was washed three times with 1×PBS, pH 7.0 to remove remaining drug or polymer. On the third wash, 2 aliquots of 0.45 ml were prepared and centrifuged. One cell pellet of each condition was resuspended with 0.45 ml of 1×PBS, pH 7.0, and 0.1 ml of suspension was serially diluted and plated. The other cell pellet of each condition was resuspended with 0.45 ml of 1×PBS, pH 4.0. Both suspensions were incubated for 2 and 4 h to analyze the effect of pH on NPC treatment. At each time point, aliquots of each suspension were diluted for 10-fold plating on blood agar plates. The plates were incubated for 48 h (37° C., 5% $CO_2$) prior to counting of CFU with (info regarding CFU counter).

Five treatment solutions were used to treat biofilms: free NPC (1.47 mg/ml NPC, in 1×PBS, pH 7.0), NPC-farnesol (1.47 mg/ml NPC, loaded with 0.3 mg/ml farnesol, in 1×PBS, pH 7.0), free-farnesol (0.3 mg/ml farnesol, in 1×PBS, pH 7.0, 15% ethanol (EtOH)); vehicle control for free-farnesol (1×PBS, pH 7.0, 15% EtOH), and PBS (1×PBS, pH 7.0). 15% v/v ethanol was used as a vehicle to solubilize free farnesol, which is insoluble at effective concentrations in aqueous media and has previously been shown to have no effect on *S. mutants* biofilm development (Koo et al., 2003, J Antimicrob Chemother, 52(5):782-9). Biofilms of *S. mutans* UA159 were formed on saliva coated hydroxyapatite (sHA) surfaces (12.7 mm in diameter, 1 mm in thickness, Clarkson Chromatography Products Inc., South Williamsport, Pa.) as detailed elsewhere (Koo et al., 2010, J Bacteriol, 192(12):3024-32). The HA discs were placed vertically using a custom-made holder and grown in UFTYE (pH 7.0) with 1% sucrose at 37° C. and 5% $CO_2$. Disks were pretreated with the above-described solutions for 10 min, washed twice with sterile saline, and transferred back to culture media. The first treatment was applied directly after salivary pellicle formation (sHA) then treated disks were transferred to culture media containing *S. mutans* ($10^5$ CFU/ml). Biofilms were allowed to form on the discs without interruption for 6 hours at which point a second treatment was applied. The next day, biofilms were treated every 6 hours for a total of 3 treatments and the culture media was changed twice. After 48 hours, the amount of colony forming units (CFU) per dry-weight of biofilms was assessed. Briefly, the biofilms were removed and homogenized, then plated onto blood agar plates, and after incubation at 37° C., 5% $CO_2$, the CFUs were counted as described previously (Koo et al., 2003, J Antimicrob Chemother, 52(5):782-9).

Statistical Analysis

Significance among groups was assessed by Two-Way AVOVA followed by Tukey's tests for multiple comparisons at p-values of $P<0.01$. Alternatively, a significance of Pearson correlations ($r^2>0$) that show trends in binding versus pH and zeta potentials, as compared to no correlation ($r^2=0$), were assessed by two-tailed t-tests at p-values of $p<0.01$. Goodness of fits to first-order release kinetics, and Langmuir adsorption equilibrium was assessed by adjusted $R^2>0.98$ for all fits and D'Agostino & Pearson omnibus (K2) normality tests on residuals at p-values of $P<0.05$.

The results of the experiments are now described.

Polymer Structure and Function

Figures 7A, 7B:
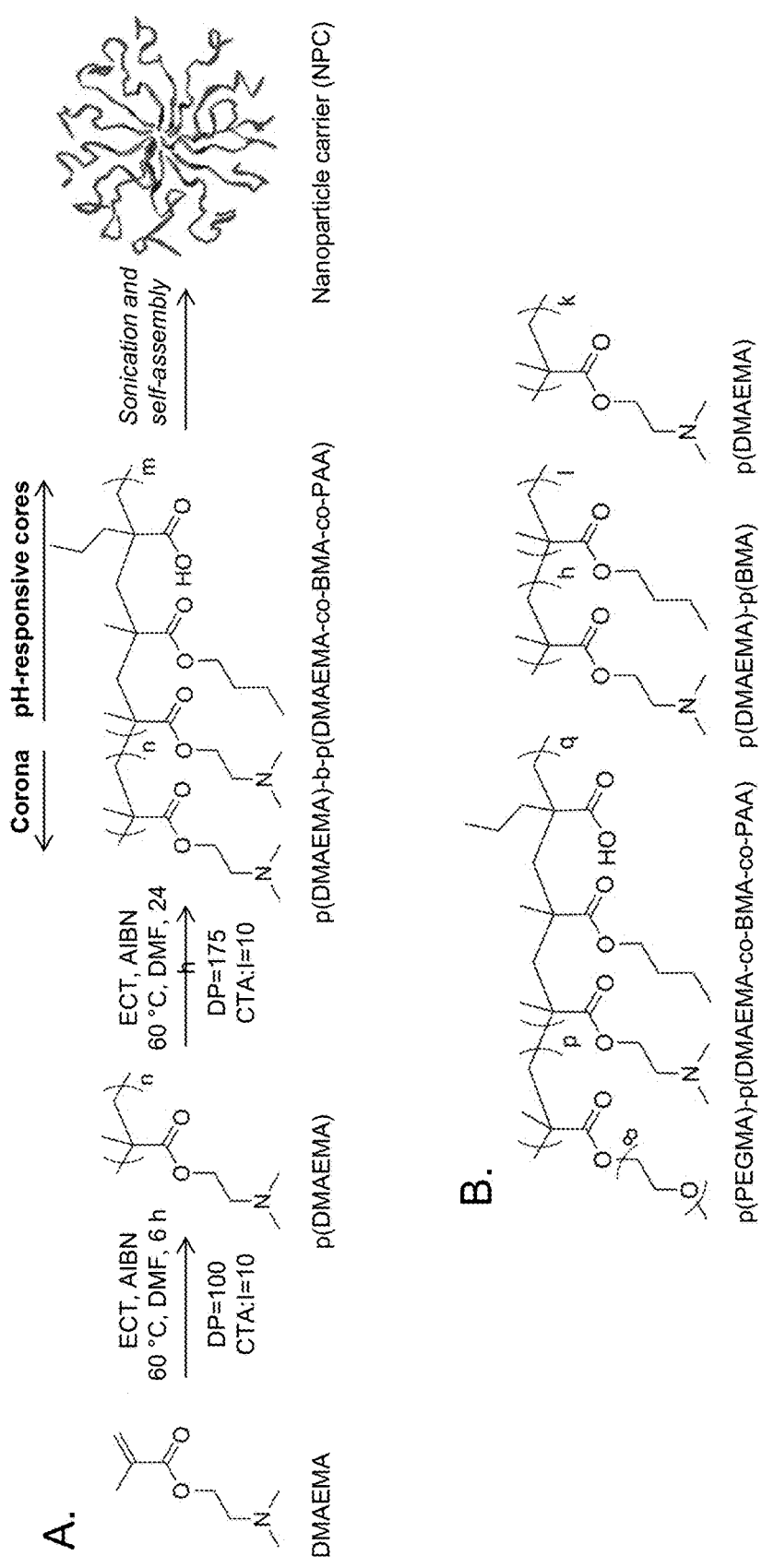
Figure 7D:
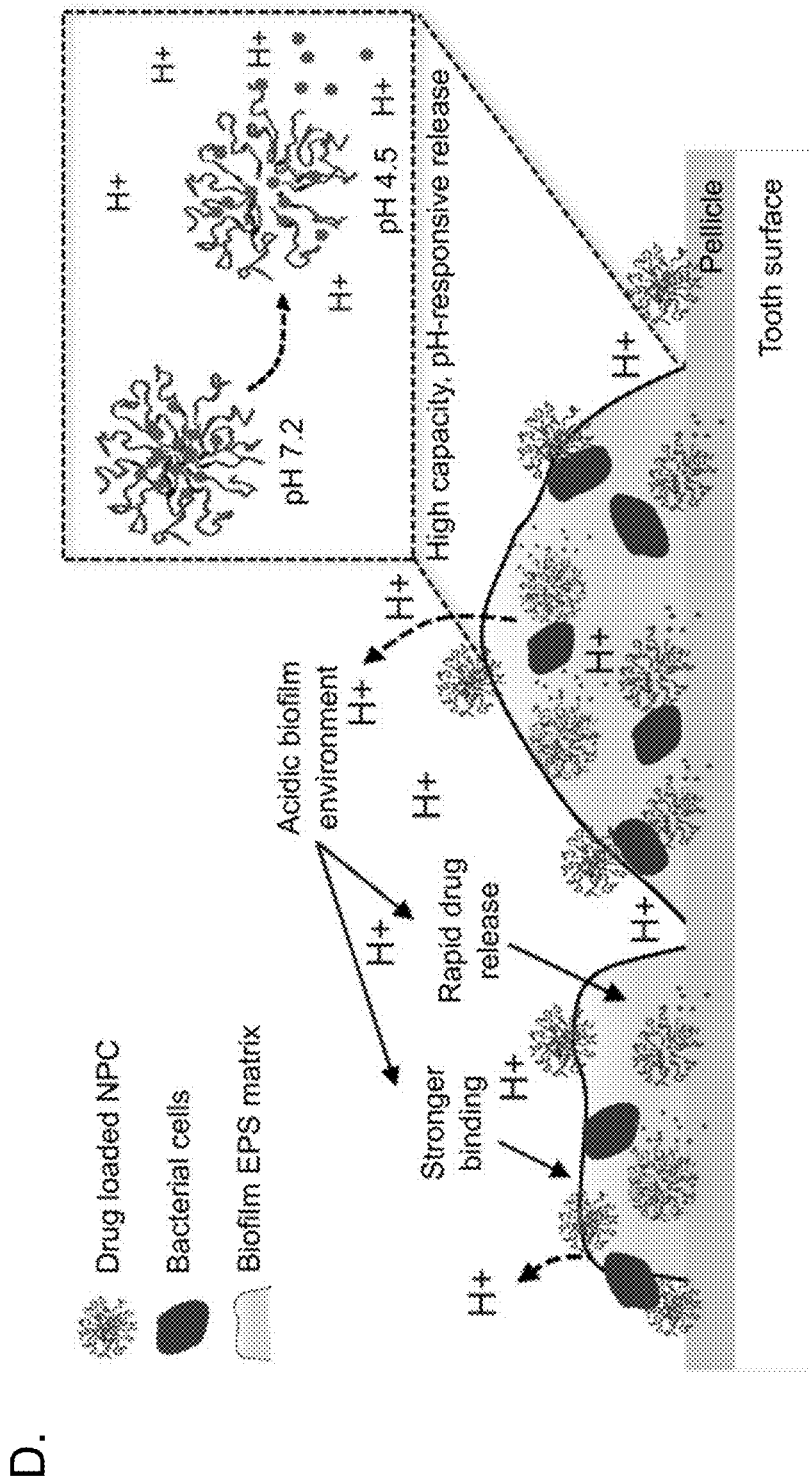

All polymers used in this work were formed via RAFT polymerization, which provides precise control over polymer molecular weights and polydispersity indices ($M_w/M_n$, PDI<1.3). The structure, composition, and physical properties of pH-responsive p(DMAEMA)-b-p(DMAEMA-co-BMA-co-PAA) that form micelle-based nanoparticle carriers (NPCs), and of polymers used as controls for adsorption to mimetic dental surfaces are detailed in FIG. 7A-FIG. 7C. p(DMAEMA)-b-p(DMAEMA-co-BMA-co-PAA) diblocks were synthesized in a two-step RAFT polymerization at equivalent $1^{st}$ to $2^{nd}$ block ratios (FIG. 7A). First, positively charged 9.5 kDa p(DMAEMA) blocks were synthesized (PDI=1.3) (FIG. 7A and FIG. 7C). From this p(DMAEMA) macroCTA, second blocks of pH-responsive p(DMAEMA-co-BMA-co-PAA) were added (Benoit et al., 2011, Biomacromolecules, 12(7):2708-14; Convertine et al., 2009, J Control Release, 133(3):221-9) (FIG. 7A) so that an overall molecular weight of NPC polymer was 17.8 kDa (PDI=1.1) (FIG. 7C). Control diblocks that form micelle-based nanoparticles were synthesized similarly (FIG. 7B). p(PEGMA)-b-p(DMAEMA-co-BMA-co-PAA) polymers, (C2), were synthesized with 18.7 kDa (PDI=1.08) and 29.0 kDa (PDI=1.09) first blocks and overall $M_n$ respectively (FIG. 7C), whereas p(DMAEMA)-b-p(BMA) polymers, (C3), were synthesized with 22.8 kDa (PDI=1.08) coronas and 37 kDa (PDI=1.01) overall $M_n$ (FIG. 7C).

p(DMAEMA)-b-p(DMAEMA-co-BMA-co-PAA) diblocks self-assemble into ~21 nm, monodisperse micelles (PDI=0.2) with low critical micelle concentrations (CMC) (0.008 mg/ml, FIG. 11). The CMC measured for the micelle-based nanoparticle carriers (NPC) was comparable to reported values (0.002 mg/ml) for diblocks with similar polymer compositions (Convertine et al., 2010, Biomacromolecules, 11(11):2904-11). p(DMAEMA) is 50% protonated at physiologic pH owing to tertiary amines residues (pKa ~7.5) (Van de Wetering et al., 1999, Bioconjug Chem, 10(4):589-97; van de Wetering et al., 1998, Macromolecules, 31(23):8063-8). NPC coronas assemble due to interaction of p(DMAEMA) with aqueous media, which results in positive zeta potentials ($\zeta=+15.9$ mV) of NPC (FIG. 7C), whereas NPC cores assemble as a result of hydrophobic interactions among BMA residues of p(DMAEMA-co-BMA-co-PAA) blocks (Benoit et al., 2011, Biomacromolecules, 12(7):2708-14; Convertine et al., 2009, J Control Release, 133(3):221-9; Manganiello et al., 2012, Biomaterials, 33(7):2301-9; Convertine et al., 2010, Biomacromolecules, 11(11):2904-11).

Control polymers including p(DMAEMA) (C1), and diblocks of p(PEGMA)-b-p(DMAEMA-co-BMA-co-PAA) (C2) and p(DMAEMA)-b-p(BMA) (C3), were used to demonstrate the role of p(DMAEMA) coronas and nanoparticle structure in binding to dental surfaces (FIG. 7B). Thus, nanoparticles with either neutral or positive zeta potentials were used (FIG. 7C). For example, 21 nm (diameter PDI=0.37) nanoparticles with p(PEGMA) coronas and pH-responsive cores (C2) have slightly negative zeta potential ($\zeta=-1.6$ mV) (FIG. 7C). Alternatively, 38 nm micelles (diameter PDI=0.21) with p(DMAEMA) coronas and p(BMA) cores (C3) that lack pH-responsive PAA and DMAEMA residues, have similar zeta potentials $\zeta=+17.2$ mV) to NPC (FIG. 7C). 16.0 kDa p(DMAEMA) (PDI=1.01), was used as a positive control for charge-mediated binding at pH 7.2 when p(DMAEMA) amine residues are protonated, and as a negative control at pH 10.5, when the amine residues are deprotonated. p(DMAEMA)

alone did not form nanoparticles, therefore diameters, PDI and zeta potentials for p(DMAEMA) were not measurable.

Nanoparticle Adsorption to Distinct Dental Surfaces Mimetics

Adsorption to surfaces depends on several factors; overall charge, density of charged residues, molecular weight, tertiary molecular conformation, pH and ionic strength (Gorbunoff et al., 1984, Anal Biochem, 136(2):440-5; Bhat et al., 2004, Macromol Rapid Commun, 25(1):270-4; Sakai et al., 2007, J Colloid Interface Sci, 314(2):381-8). Thus, three mimetic dental surfaces were used to assess polymer binding (FIG. 8): uncoated hydroxyapatite (HA) that mimics tooth mineral or dental enamel, hydroxyapatite coated with saliva (sHA), that mimics dental pellicle (Weerkamp et al., 1988, J Dent Res, 67(12):1483-7; Koo et al., 2002, Antimicrob Agents Chemother, 46(5):1302-9; Lendenmann et al., 2000, Adv Dent Res, 14(1):22-8; Ambatipudi et al., 2010, J Proteome Res, 9(12):6605-14; Koo et al., 2000, Caries Res, 34(5):418-26), and hydroxyapatite coated with salivary pellicle and glucans (gsHA), which mimics initial stages of EPS secretion during biofilm formation (Koo et al., 2010, J Bacteriol, 192(12):3024-32; Ambatipudi et al., 2010, J Proteome Res, 9(12):6605-14; Rozen et al., 2001, FEMS Microbiol Lett, 195(2):205-10).

Figures 8A, 8B:
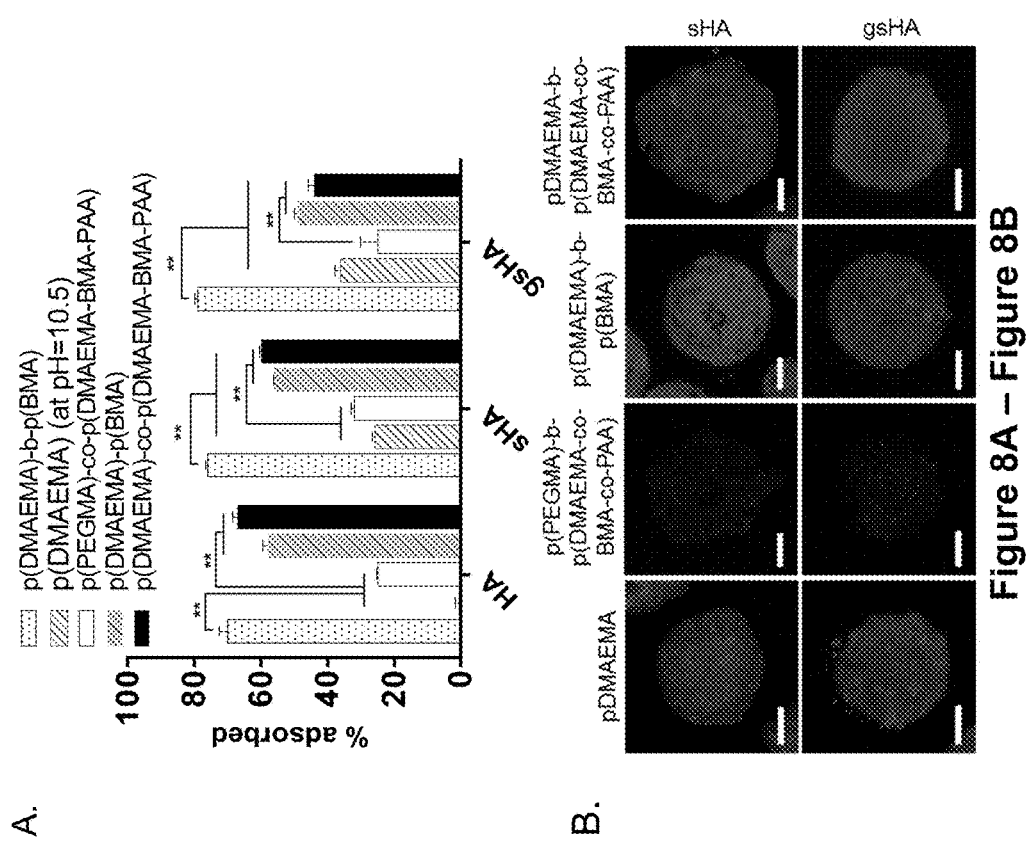
FIG. 8A through FIG. 8G, depicts the results of experiments demonstrating the characterization of binding to mimetic dental surfaces.

As shown in FIG. 8A, 67%, 60%, and 44% of NPC bound to HA, sHA and gsHA respectively, as compared to 70%, 76% and 79% of p(DMAEMA) at pH 7.2 (FIG. 8A). This data indicates that tertiary amine residues of p(DMAEMA) coronas, as they are 50% protonated at physiologic pH (Van de Wetering et al., 1999, Bioconjug Chem, 10(4):589-97; van de Wetering et al., 1998, Macromolecules, 31(23):8063-8), are responsible for binding to dental mimetic surfaces. While not wishing to be bound by any particular theory, the decrease in binding of NPC to sHA and gsHA as compared to protonated p(DMAEMA) (at pH 7.2) could relate to screening of the HA surface by addition of saliva (sHA) and glucans (gsHA). These additional surface components had no effect on the binding of p(DMAEMA) though, possibly due to alternative interactions such as H-bonding or assembly of p(DMAEMA) with pellicle proteins or negatively charged glucans. As compared to p(DMAEMA) at pH 7.2, deprotonated p(DMAEMA) (at pH 10.5) did not bind to HA (0.5%) and bound much less prominently to sHA (25.9%) and gsHA (36.2%) (FIG. 8A). Binding of deprotonated p(DMAEMA) (at pH 10.5) to sHA and gsHA also supports alternative binding mechanisms (e.g., H-bonding, hydrophobic interactions, or assembly with pellicle proteins or glucans).

Next, NPC binding was compared to polymers that similarly form nanoparticles (C2 and C3) (FIG. 8A, FIG. 7B, and FIG. 7C). These included nanoparticles formed from block copolymers of p(DMAEMA)-b-p(BMA) and (p(PEGMA)-b-(DMAEMA-co-BMA-PAA)) (FIG. 7B-FIG. 7C). p(DMAEMA)-p(BMA) were utilized to confirm the role of p(DMAEMA) coronas and not pH-responsive nanoparticle cores in binding. p(DMAEMA)-b-p(BMA) polymers bound similarly to NPC for all dental mimetic surfaces (HA (58%), sHA (56%), gsHA (49%)) (FIG. 8A). Adsorption of NPC relative to polymers with p(PEGMA) coronas and pH-responsive p(DMAEMA-co-BMA-co-PAA) cores was assessed to confirm that nanoparticles with neutral, hydrophilic coronas (unlike p(DMAEMA)) will not bind. p(PEGMA)-b-p(DMAEMA-co-BMA-co-PAA) nanoparticles bound to dental mimetic surfaces albeit at about half the level of NPC (25%, 32%, 25%) (FIG. 8A).

Figures 8C, 8D:
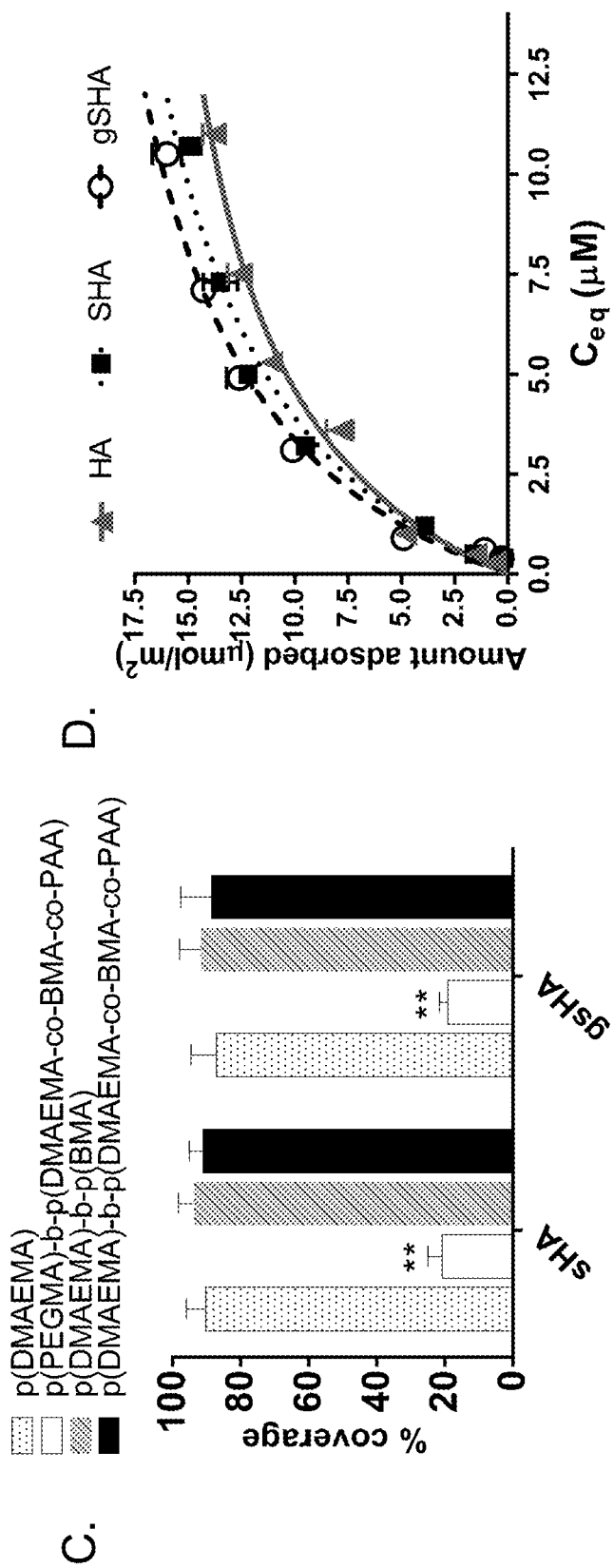

Binding of polymers to mimetic dental surfaces was confirmed by confocal imaging (FIG. 8B). Similar to the quantitative data, confocal images show that binding of NPC, p(DMAEMA)-b-p(BMA), and p(DMAEMA) was greater than binding of nanoparticles with p(PEGMA) coronas on both sHA and gsHA surfaces. Similarly, the following % polymer coverage of sHA and gsHA was observed: 21% and 19% by p(PEGMA)-b-p(DMAEMA-co-BMA-co-PAA) as compared to 90% and 87% by p(DMAEMA), 94% and 92% by p(DMAEMA)-b-p(BMA) and 91% and 89% by NPC as shown in FIG. 8C.

Figures 8E, 8F, 8G:
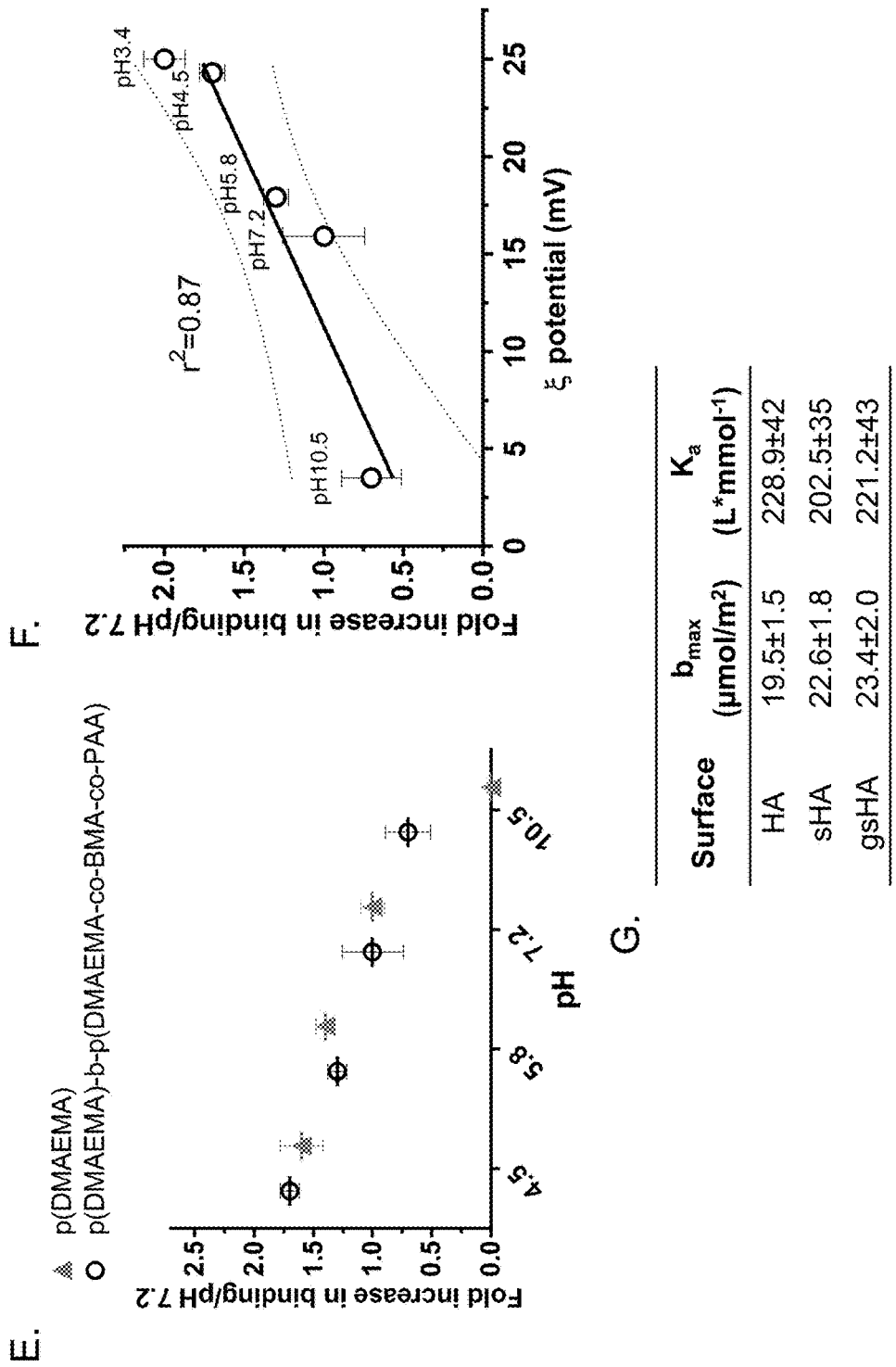
Figure 14:
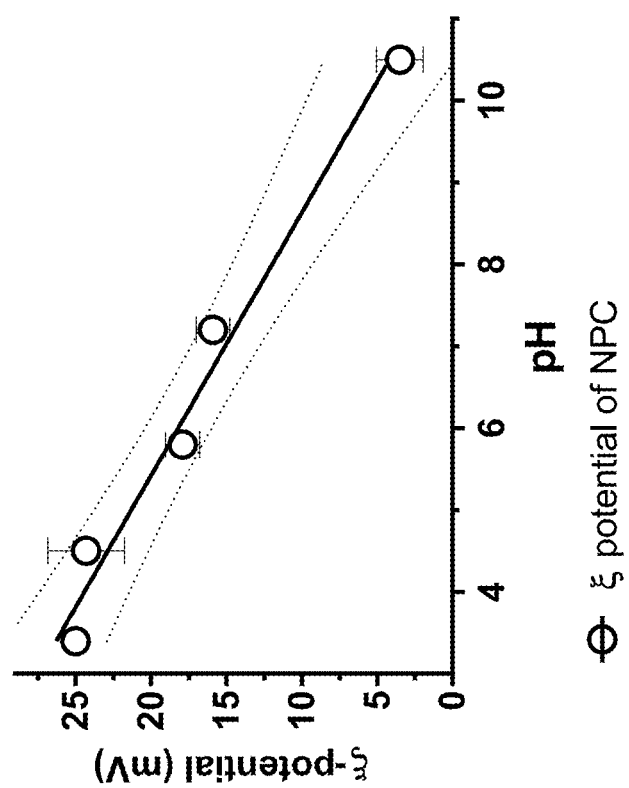
FIG. 14 depicts the results of experiments demonstrating that NPC surface charge decreases with increasing pH. NPC zeta potentials were measured by DLS at a range of pH (3.4-10.5) in PBS. The error bars represent standard deviation (n=5). The solid line denotes Pearson correlation, external and internal dotted lines denote confidence intervals of Pearson correlation at 95% confidence
Figure 15:
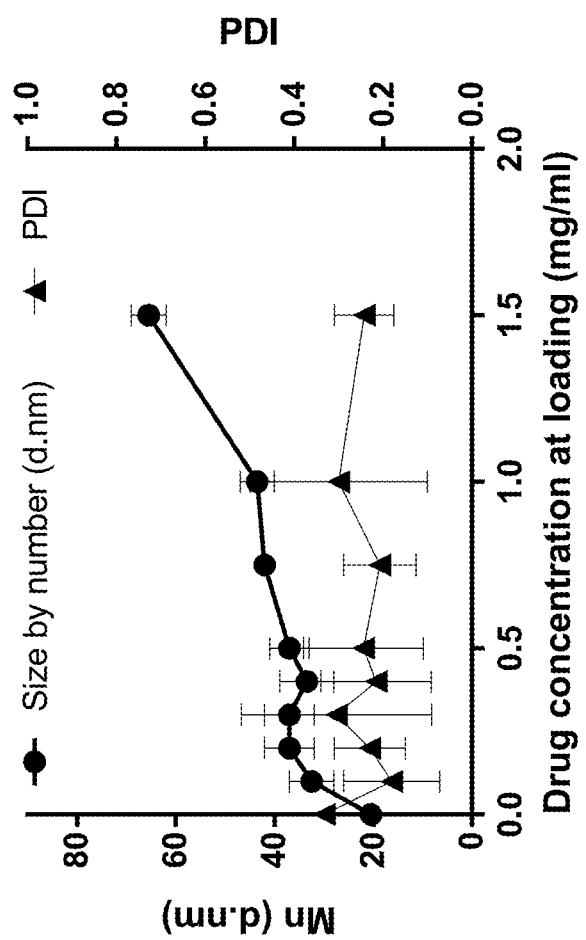
FIG. 15, depicts the results of experiments demonstrating the observation of an increase in NPC size upon loading. NPC sizes were examined by dynamic light scattering (DLS) upon loading at a range of drug concentrations (0.2-1.5 mg/ml). Measurements were performed on two independent polymer batches in triplicates (n=2).

As they exhibited the greatest adsorption and have inherent pH-responsive behavior (Benoit et al., 2011, Biomacromolecules, 12(7):2708-14; Convertine et al., 2009, J Control Release, 133(3):221-9), more sophisticated adsorption experiments were performed using micelle-based nanoparticle carriers (NPCs) composed of p(DMAEMA)-b-p(DMAEMA-co-BMA-co-PAA) (FIG. 8D). According to Langmuir fits to adsorption data (FIG. 8G), the average maximal binding capacity ($X_{max}$) of NPC on dental surfaces was ~21 μmol/m$^2$ and the adsorption affinity constants ($K_a$) were ~215 L*mmol$^{-1}$. These values did not differ statistically between the various dental surfaces. This affinity of adsorption was found to be several orders of magnitude higher than the affinity of several bisphosphonates to hydroxyapatite, whereas the adsorption capacities were comparable to those of bisphosphonates to hydroxyapatite (Claessens et al., 2000, Langmuir, 16(3):1360-7; Al-Kattan et al., 2010, Adv Eng Mater, 12(7):B224-B233; Pascaud et al., 2012, Biomed Mater, 7(5):054108; Leu et al., 2006, Bone, 38(5):628-36; Sato et al., 1991, J Clin Invest, 88(6): 2095-105), which implies that may NPC adsorb faster but at similar maximal amounts. Specifically, the $K_a$ of bisphosphonates, which are known to have exceptionally high affinity to hydroxyapatite, is in the range of 1-13.8 L*mmol$^{-1}$ (Claessens et al., 2000, Langmuir, 16(3):1360-7; Al-Kattan et al., 2010, Adv Eng Mater, 12(7):B224-B233; Pascaud et al., 2012, Biomed Mater, 7(5):054108; Leu et al., 2006, Bone, 38(5):628-36; Sato et al., 1991, J Clin Invest, 88(6):2095-105), but is ~20-~60 times weaker than the affinity of NPC (affinities of ~221-~229 L*mmol$^{-1}$). However, other sources report higher (~720-3470 L*mmol$^{-1}$) affinities for several bisphosphonates, perhaps as a result of different or indirect measurement methods (Nancollas et al., 2006, Bone, 38(5):617-27; Henneman et al., 2008, J Biomed Mater Res A, 85(4):993-1000). The maximal adsorption capacity ($X_{max}$) of bisphosphonates is 2.17-2.31 μmol/m$^2$ (Claessens et al., 2000, Langmuir, 16(3):1360-7; Al-Kattan et al., 2010, Adv Eng Mater, 12(7):B224-B233; Pascaud et al., 2012, Biomed Mater, 7(5):054108), similar to the maximal adsorption of NPC to dental surfaces (19.5-23.4 μmol/m$^2$). Also, the affinities of NPC to HA, sHA, and gsHA ($K_a$=~215 L*mmol$^{-1}$, $X_{max}$=~21 μmol/m$^2$) (FIG. 8G) were greater than several types of nanoparticles functionalized with alendronate, a bisphosphonate. Alendronate-functionalized Au NPs exhibited enhanced $K_a$ (~4.5 μmol alendronate/m$^2$) to HA over unfunctionalized Au NPs, however the $K_a$ of Au NPs is only ~25% of the NPC described here (Ross et al., 2011, J Biomed Mater Res A, 99(1):58-66). Similarly, alendronate-functionalized nanoparticles bind at lower capacities to HA (Chen et al., 2009, Antimicrob Agents Chemother, 53(11):4898-902). While not wishing to be bound by any particular theory, the improved binding of NPC may be due to high density of charged amines (Gorbunoff et al., 1984, Anal Biochem, 136(2):440-5) of NPC coronas compared to functionalized nanoparticles.

p(DMAEMA) binding was also examined at acidic pH. Binding of p(DMAEMA) to HA is stronger at acidic pH (FIG. 8E) compared to physiological conditions due to increased protonation of amine residues. Thus, DMAEMA is suitable for targeting drugs to negatively charged dental surfaces at pathologic conditions which results in localized acidic pH (Xiao et al., 2012, PLoS Pathog, 8(4):e1002623). Similar to p(DMAEMA), binding of NPC to HA increased at low pH (FIG. 8E). However, when binding is performed at pH 10.5, conditions at which amines of p(DMAEMA) are deprotonated, ~70% of NPC bound to HA compared to binding observed at pH 7.2, whereas 0% of p(DMAEMA) bound at this alkaline pH (FIG. 8E), similar to data presented in FIG. 8A. This suggests that other factors may impact the binding of NPC to dental surfaces. These factors may include nanoparticle size and shape or density of amine residues on the nanoparticle surface (Gorbunoff et al., 1984, Anal Biochem, 136(2):440-5) which may result in different interactions with dental surfaces. Thus, an additional analysis of binding was performed as a function of nanoparticle zeta potential (FIG. 8F). NPC binding was correlated with zeta potential, which was altered by changing the pH of the nanoparticle solution (FIG. 14). A significant positive correlation between NPC binding and zeta potential was observed (FIG. 8F). While not wishing to be bound by any particular theory, greater binding, and higher zeta potentials of NPC at acidic pH (FIG. 8E-FIG. 8F), is likely due to increased protonation of amines of p(DMAEMA), which contributes to NPC interactions with negatively-charged groups of HA (Gorbunoff et al., 1984, Anal Biochem, 136(2):440-5).

Drug Loading and pH Triggered Farnesol Release p(DMAEMA)-b-p(DMAMEA-co-BMA-co-PAA) NPC were loaded with farnesol at up to 27% wt (FIG. 13A) which is ~26% higher than its minimum inhibitory concentration (MIC) (Jabra-Rizk et al., 2006, Antimicrob Agents Chemother, 50(4):1463-9; Koo et al., 2002, Antimicrob Agents Chemother, 46(5):1302-9). The concentration of farnesol within nanoparticles is ~440 times higher than its estimated solubility limit (~$1.7*10^{-3}$ mg/ml) in the absence of a carrier. Upon loading at 27.0 wt %, the size of NPC increased from 20.5 nm to 60.3 nm, whereas loading efficiencies were above ~90% throughout the range of loading concentrations (FIG. 13B). The spherical shape of NPC and size increases were confirmed by transmission electron microscopy (TEM) for unloaded controls and NPC loaded with farnesol at 18.4 wt % and 27.0 wt % (FIG. 9A). Similar effects on size due to drug loading were reported for diblock micelles formed of poly(lactic-co-glycolic acid)-b-poly(ethylene glycol) (PLGA-b-PEG), and polystyrene-b-poly(ethylene glycol) (PS-b-PEG) (Zhu, 2013, Biomaterials, 34(38): 10238-48), and p(DMAEMA)-p(BMA) (Benoit et al., 2010, Mol Pharm, 7(2):442-55). The increase in NPC diameter calculated from specific volumes of farnesol and NPC, if loaded at 18.5 wt % was ~16.8 nm, which is similar to the measured increase of ~16.5 nm in nanoparticle size at 18.5 wt % loading. In addition, larger diameters (45 nm) were reported for nanoparticles with similar p(DMAEMA) coronas but 2-fold larger p(DMAEMA-co-BMA-co-PAA) cores (Convertine et al., 2010, Biomacromolecules, 11(11):2904-11). Therefore, while not wishing to be bound by any particular theory, increases in nanoparticles size are likely due to assembly and hydrophobic interactions of farnesol with hydrophobic residues of NPC cores, which effectively increase the overall nanoparticle core volumes.

Farnesol release from NPC was assessed as a function of pH (FIG. 9B). Farnesol release was twice as fast at pH 4.5 compared to pH 7.2, which is quantified by the first order kinetic constants ($k_{pH=4.5}$=0.094 l/hr, $k_{pH=7.2}$=0.047 l/hr). In addition, farnesol release half-life was quantified and found to be $t_{1/2}$=7.3 hr and $t_{1/2}$=14.7 hr for release at pH 4.5 and pH 7.2, respectively. Faster release at acidic pH is likely due to reported pH-responsive behavior of NPC cores (Benoit et al., 2011, Biomacromolecules, 12(7):2708-14; Convertine et al., 2009, J Control Release, 133(3):221-9; Wang and Rempel, 2013, J Polym Sci Part A Polym Chem, 51(20):4440-50; Fan et al., 2012, Biomacromolecules, 13(12):4126-37; Manganiello et al., 2012, Biomaterials, 33(7):2301-9). Specifically, at low pH, the DMAEMA residues (pKa=7.2) are fully protonated as compared to 50% protonation at pH 7.2. Thus, the overall charge of the core results in electrostatic repulsion, which destabilized nanoparticle cores and triggers farnesol release (Benoit et al., 2011, Biomacromolecules, 12(7):2708-14; Convertine et al., 2009, J Control Release, 133(3):221-9). Similar effects of low pH were observed in nanoparticles with diethylaminoethyl methacrylate (DEAEMA) tertiary amine cores (Wang and Rempel, 2013, J Polym Sci Part A Polym Chem, 51(20):4440-50; Fan et al., 2012, Biomacromolecules, 13(12):4126-37; Manganiello et al., 2012, Biomaterials, 33(7):2301-9).

Farnesol release rate over time was modeled and the resulting predictions are shown in FIG. 9B (inset). The initial release rate at pH 4.5 is ~8% per hour as compared to ~4% hr at pH 7.2. Therefore at pH 4.5 nanoparticles will release an amount of drug equivalent to 1 MIC after ~½ hour as compared to ~1 hr at pH 7.2 (FIG. 9B inset). Also, at pH 4.5, farnesol release rate decreases over time, whereas at pH 7.2 the release rate is relatively stable. Moreover, the release rates equalize after ~12 hr. However, nearly all drug (75%) is released at pH 4.5, whereas complete release at pH 7.2 requires ~30 hr. Thus, at low pH consistent with biofilm microenvironments, farnesol release is rapid.

Anti-Bacterial and Anti-Biofilm Effect of Loaded NPC

Figures 9D, 9E:
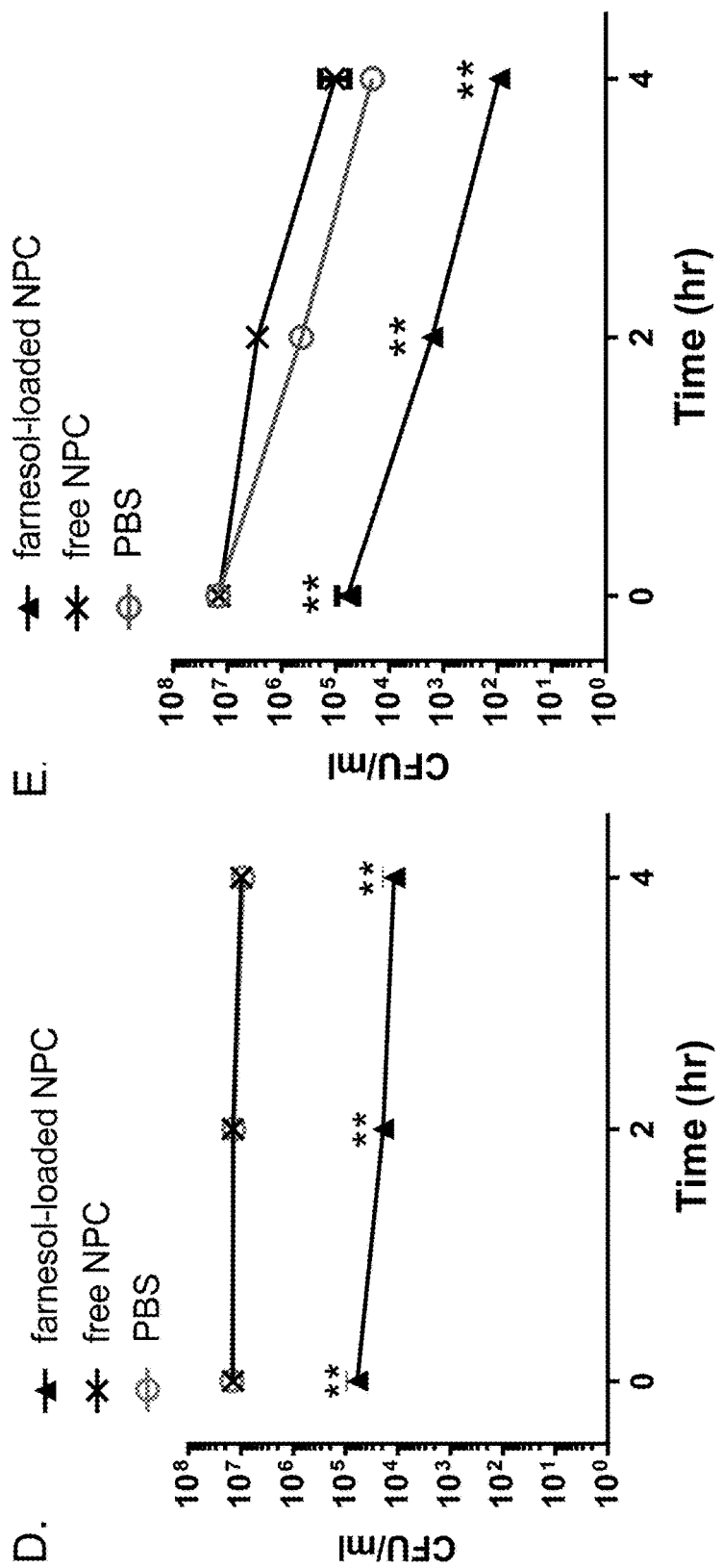

Antibacterial activity of drug-loaded NPC was assessed via 1 hour incubations of drug-loaded NPC with S. mutants (FIG. 9D-FIG. 9E). After treatment, bacteria were washed and transferred to PBS at either pH 7.2 or pH 4.5 to assess the long-term effects of drug loaded NPC (FIG. 9D-FIG. 9E). S. mutants viability decreased by ~3 logs (see $t_0$ in FIG. 9D-FIG. 9E) after exposure to drug-loaded NPC as compared to unloaded nanoparticles and to PBS controls. However no further decreases in CFU counts were observed 2 and 4 hours after bacteria was washed and transferred to pH 7.2 (FIG. 9D). While not wishing to be bound by any particular theory, the lack of temporal effects of farnesol may be attributed to substantial ~3 log decrease in bacterial viability after 1 hour of exposure to loaded NPC and that after treatment, NPC solution was removed and bacterial cells were washed. In comparison, after cells were transferred to pH 4.5, the rate of CFU decrease was steady over time (FIG. 9E), which implies that low pH impaired the viability of S. mutants, possibly resulting in increased susceptibility to low pH culture after treatment with farnesol.

Figure 10:
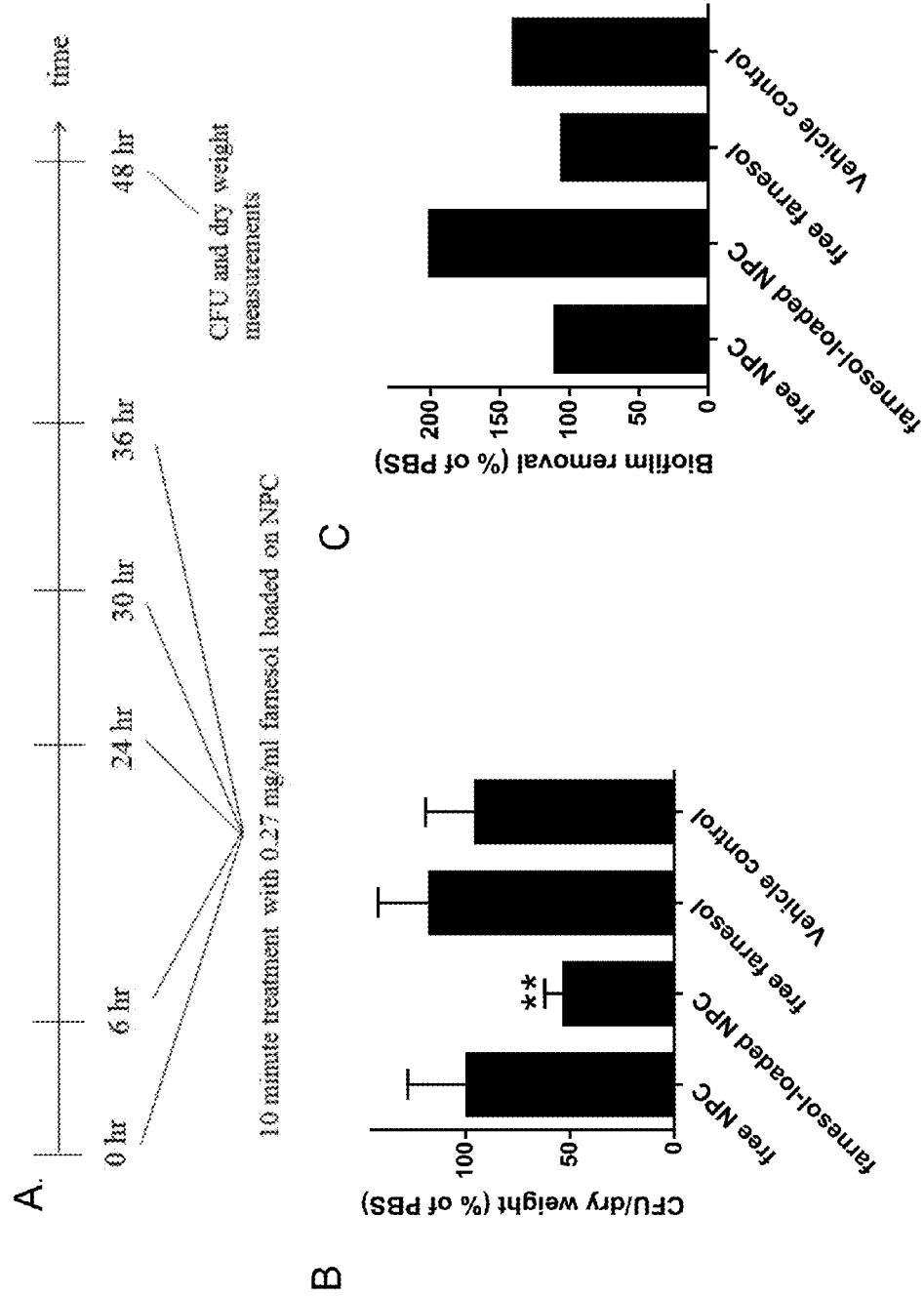
FIG. 10, comprising

Antibiofilm activity of farnesol was assessed using a clinically-relevant treatment regimen for S. mutants-based biofilms as shown in FIG. 10A. The amount of farnesol in either free farnesol (at 15% EtOH) or NPC-fanesol treatment solutions (0.27 mg/ml) was ~10×~20× higher that its MIC (<~0.028 mg/ml), and ~440× times higher than its solubility limit in aqueous media ($1.7*10^{-3}$ mg/ml). A significant ~50% decrease in CFU per dry weight of biofilm was observed for NPC-farnesol treated samples (FIG. 10B). In contrast, treatments with equivalent doses of free farnesol, or controls of free NPC or farnesol vehicle control (15% EtOH) showed no effect on CFU relative to PBS (FIG. 10B). Antibiofilm effects of NPC-farnesol were likely observed as a result of retention at the surfaces at risk and within biofilms and of extremely high concentrations of farnesol, while being optimally released locally by the NPC (FIG. 7C) as the pH becomes acidic within the *S. mutans* biofilms. Free farnesol was not able to prevent biofilm formation whereas farnesol delivered by NPC was sufficient to significantly decrease bacterial survival (FIG. 9D-FIG. 9E) and prevent biofilm formation (FIG. 10B). This suggests that along with the local release of farnesol from NPC triggered by the low pH of the biofilm microenvironment, either NPC binding to biofilms and/or dental surfaces, or NPC binding/interaction with bacterial membranes mediate the effect. For example NPC attachment to bacterial of biofilm surface, would result in increased effective concentration of fanesol in situ, therefore more substantial therapeutic effects (Koo et al., 2003, J Antimicrob Chemother, 52(5):782-9; Jabra-Rizk et al., 2006, Antimicrob Agents Chemother, 50(4):1463-9; Kaneko et al., 2011, J Antibiot (Tokyo), 64(8):547-9). Also, cationic nanoparticles are known for their interaction with biological membranes (Benoit et al., 2010, Mol Pharm, 7(2):442-55; Benoit et al., 2011, Biomacromolecules, 12(7):2708-14; Convertine et al., 2009, J Control Release, 133(3):221-9), which may result in farnesol incorporation into bacterial membranes and impaired membrane integrity (Koo et al., 2003, J Antimicrob Chemother, 52(5):782-9; Jabra-Rizk et al., 2006, Antimicrob Agents Chemother, 50(4):1463-9), or drug release within bacterial cells and inhibition of certain metabolic pathways (Kaneko et al., 2011, J Antibiot (Tokyo), 64(8):547-9).

Experiments were conducted where the treated biofilms were subjected to constant shear forces (ranging from 0 to 1.785 N/m$^2$) applied directly to the biofilm surface using a custom-built device. After application of shear stress, the amount of biofilm's dry-weight (biomass) that remained on the surface was measured. It was observed that NPC loaded with farnesol exhibited greater biofilm removal after shear stress, as compared to both free farnesol or free NPC (FIG. 10C).

p(DMAEMA)-b-p(DMAEMA-co-BMA-co-PAA) NPC strongly adsorb to dental surfaces with affinities ~20 times higher than the affinities of bisphosphonates to hydroxyapatite (Al-Kattan et al., 2010, Adv Eng Mater, 12(7):B224-B233). Nanoparticle affinity is likely due to positively-charged amine residues of the external p(DMAEMA) coronas that interact with the overall negative charge of dental surfaces, and biofilms, as similar adsorption behavior of NPC was observed to p(DMAEMA) alone, and p(DMAEMA)-b-p(BMA) nanoparticles. Farnesol, which has minimal aqueous solubility, can be loaded and delivered from nanoparticles at ~26.7-fold greater concentrations than its minimal inhibitory concentration (MIC) for common oral bacteria such as *Streptococcus mutants* (*S. mutans*) (Koo et al., 2002, Antimicrob Agents Chemother, 46(5):1302-9). Rapid pH-responsive farnesol release indicates that nanoparticle delivery may be beneficial for the relatively short treatment windows consistent with dental regimens and the low pH microenvironments of pathologic dental biofilms. In addition, excellent antibiofilm activity of loaded NPC was demonstrated. Thus, NPC have great potential to deliver antibiofilm drugs, increasing their efficacy due to localized, rapid, and triggered release to cariogenic biofilms.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for preventing biofilm formation, preventing biofilm accumulation, and disrupting biofilm, the composition comprising at least one nanoparticle carrier (NPC) having a shell and a core, wherein the core comprises a therapeutically effective amount of at least one therapeutic agent, wherein the NPC comprises poly(dimethylaminoethyl methacrylate)-b-poly(dimethylaminoethyl methacrylate-co-propylacrylic acid-co-butyl methacrylate) (pDMAEMA-b-p(DMAEMA-co-PAA-co-BMA)).

2. The composition of claim 1, wherein the composition comprises a pH-responsive element such that the NPC is disassembled when the NPC is in a locally acidic pH environment, thereby releasing the at least one therapeutic agent.

3. The composition of claim 1, wherein the NPC binds to a biofilm.

4. The composition of claim 1, wherein the composition binds to multiple surfaces at risk for biofilm formation and accumulation.

5. The composition of claim 1, wherein the at least one therapeutic agent comprises at least one agent selected from the group consisting of farnesol, apigenin, fluoride, chlorhexidine, and derivatives thereof.

6. The composition of claim 1, wherein the at least one therapeutic agent is linked to the core via a degradable tether.

7. The composition of claim 6, wherein the length of the degradable tether controls the rate of release of the therapeutic agent.

8. The composition of claim 1, wherein the NPC is incorporated into at least one of the group consisting of a liquid, foam, paste, gel, gum, membrane, dissolvable substrate, tablet, capsule, and lozenge.

9. A method for treating a biofilm comprising administering to a surface having a biofilm a composition comprising at least one NPC and at least one therapeutic agent within the at least one NPC, wherein the at least one NPC binds selectively to the surface and is selectively triggered to release the at least one therapeutic agent, thereby providing local delivery of the therapeutic agent when the at least one therapeutic agent is released from the at least one NPC, wherein the NPC comprises poly(dimethylaminoethyl methacrylate)-b-poly(dimethylaminoethyl methacrylate-co-propylacrylic acid-co-butyl methacrylate) (pDMAEMA-b-p (DMAEMA-co-PAA-co-BMA)).

10. The method of claim 9, wherein the at least one NPC is triggered to disassemble based upon a characteristic of the microenvironment of the surface, thereby releasing the at least one therapeutic agent.

11. The method of claim 10, wherein the at least one NPC is triggered to disassemble when the at least one NPC is in locally acidic pH environment.

12. The method of claim 9, wherein the at least one therapeutic agent comprises at least one agent selected from the group consisting of farnesol, apigenin, fluoride, chlorhexidine, and derivatives thereof.

13. The method of claim 9, wherein the at least one NPC comprises a degradable tether linking the at least one therapeutic agent to a portion of the NPC, wherein the rate of release of the at least one therapeutic agent is dependent on the length of the degradable tether.

14. The method of claim 9, wherein the surface is in a subject.

15. The method of claim 14, wherein the subject has a biofilm mediated condition.

16. The method of claim 15, wherein the condition is selected from the group consisting of dental plaques, dental caries, gingivitis, urinary tract infections, catheter infections, middle-ear infections, and infections of implanted biomaterials.

17. The method of claim 14, wherein the surface is a pellicle of the subject.

18. The method of claim 14, wherein the subject is a mammal.

19. The method of claim 18, wherein the mammal is selected from the group consisting of a human, a primate, a cow, a pig, a horse, a sheep, a cat, and a dog.

20. A method of treating an oral disease in a subject, comprising administering to a pellicle of the subject a composition comprising at least one NPC and at least one therapeutic agent within the at least one NPC, wherein the at least one NPC binds selectively to the surface and is selectively triggered to release the at least one therapeutic agent, thereby providing local delivery of the at least one therapeutic agent when the agent is released from the at least one NPC, wherein the NPC comprises poly(dimethylaminoethyl methacrylate)-b-poly(dimethylaminoethyl methacrylate-co-propylacrylic acid-co-butyl methacrylate) (pD-MAEMA-b-p(DMAEMA-co-PAA-co-BMA)).

21. The method of claim 20, wherein the at least one NPC is triggered to disassemble based upon a characteristic of the microenvironment of the surface, thereby releasing the at least one therapeutic agent.

22. The method of claim 21, wherein the at least one NPC is triggered to disassemble when the at least one NPC is in locally acidic pH environment.

23. The method of claim 20, wherein the at least one therapeutic agent comprises at least one agent selected from the group consisting of farnesol, apigenin, fluoride, and chlorhexidine.

24. The method of claim 20, wherein the at least one NPC comprises a degradable tether linking the at least one therapeutic agent to a portion of the at least one NPC.

25. The method of claim 20, wherein the oral disease is selected from the group consisting of dental plaques, dental caries, gingivitis, periodontitis, denture stomatitis and oral candidiasis.

26. The method of claim 20, wherein the subject is a mammal.

27. The method of claim 26, wherein the mammal is selected from the group consisting of a human, a primate, a cow, a pig, a horse, a sheep, a cat, and a dog.

28. A method of preventing an oral disease in a subject, comprising administering to a pellicle of the subject a composition comprising at least one NPC and at least one therapeutic agent within the at least one NPC, wherein the at least one NPC binds selectively to the pellicle and is selectively triggered to release the at least one therapeutic agent, thereby providing local delivery of the at least one therapeutic agent when the agent is released from the at least one NPC, wherein the NPC comprises poly(dimethylaminoethyl methacrylate)-b-poly(dimethylaminoethyl methacrylate-co-propylacrylic acid-co-butyl methacrylate) (pD-MAEMA-b-p(DMAEMA-co-PAA-co-BMA)).

29. The method of claim 28, wherein the at least one NPC is triggered to disassemble based upon a characteristic of the microenvironment of the pellicle, thereby releasing the at least one therapeutic agent.

30. The method of claim 29, wherein the at least one NPC is triggered to disassemble when the at least one NPC is in locally acidic pH environment.

31. The method of claim 30, wherein the at least one therapeutic agent comprises at least one agent selected from the group consisting of farnesol, apigenin, fluoride, and chlorhexidine.

32. The method of claim 28, wherein the at least one NPC comprises a degradable tether linking the at least one therapeutic agent to a portion of the at least one NPC.

33. The method of claim 28, wherein the oral disease is selected from the group consisting of dental plaques, dental caries, gingivitis, periodontitis, denture stomatitis and oral candidiasis.

34. The method of claim 28, wherein the subject is a mammal.

35. The method of claim 34, wherein the mammal is selected from the group consisting of a human, a primate, a cow, a pig, a horse, a sheep, a cat, and a dog.

* * * * *